(12) United States Patent
Wisdom et al.

(10) Patent No.: US 11,516,967 B1
(45) Date of Patent: Dec. 6, 2022

(54) HARVESTING PLANTS BASED ON DETERMINED CRITERIA

(71) Applicant: Automated Harvesting Solutions, LLC, Burlington, WA (US)

(72) Inventors: Anthony Wisdom, Burlington, WA (US); Ian Mintz, Burlington, WA (US)

(73) Assignee: Automated Harvesting Solutions, LLC, Burlington, WA (US)

( * ) Notice: Subject to any disclaimer, the term of this patent is extended or adjusted under 35 U.S.C. 154(b) by 0 days.

(21) Appl. No.: 17/839,180

(22) Filed: Jun. 13, 2022

Related U.S. Application Data

(63) Continuation of application No. 16/885,911, filed on May 28, 2020, now Pat. No. 11,363,757.

(51) Int. Cl.
| | |
|---|---|
| *A01D 46/00* | (2006.01) |
| *A01D 46/30* | (2006.01) |
| *G01S 19/39* | (2010.01) |
| *G01N 33/00* | (2006.01) |
| *G01D 5/12* | (2006.01) |

(Continued)

(52) U.S. Cl.
CPC .......... *A01D 46/30* (2013.01); *A01D 46/00* (2013.01); *G01C 22/00* (2013.01); *G01D 5/12* (2013.01); *G01N 33/0098* (2013.01); *G01S 19/39* (2013.01); *G06V 20/188* (2022.01); *G06V 20/56* (2022.01); *G06V 20/68* (2022.01)

(58) Field of Classification Search
CPC ...... A01D 46/30; A01D 46/00; G06V 20/188; G06V 20/56; G06V 20/68; G01C 22/00; G01D 5/12; G01N 33/0098; G01S 19/39
See application file for complete search history.

(56) References Cited

U.S. PATENT DOCUMENTS

| | | | |
|---|---|---|---|
| 3,552,397 A | 1/1971 | Greenough | |
| 4,407,305 A | 10/1983 | Patterson | |

(Continued)

FOREIGN PATENT DOCUMENTS

| | | |
|---|---|---|
| EP | 1894464 A2 | 2/2011 |
| JP | 2014003951 | 1/2014 |

(Continued)

OTHER PUBLICATIONS

Office Action for U.S. Appl. No. 16/886,023, dated Jul. 8, 2022.
Wisdom, "De-Leafing Apparatus for Removing Leaves of Harvestable Crops", 22 pgs.

(Continued)

*Primary Examiner* — Mathew Franklin Gordon
(74) *Attorney, Agent, or Firm* — Lee & Hayes, P.C.

(57) ABSTRACT

A harvester travels along a route within a field and selectively harvests edible crowns ready for harvesting. As the harvester travels along the route, a position of the harvester and/or the edible crowns may be determined using an encoder, imaging device(s), and/or navigational system(s). For example, image(s) captured by the imaging device(s) may be used to determine a location of the edible crowns and/or global positioning satellite (GPS) coordinates may indicate a location of the harvester within the field. These locations may be used for instructing harvesting components to harvest the edible crowns. For example, the harvester may include robotic arms having end effectors that harvest the edible crowns. Knowing the location of the edible crowns and/or the harvester therefore allows for the accurate placement of the end effectors for harvesting the edible crowns.

20 Claims, 23 Drawing Sheets

(51) Int. Cl.
   *G01C 22/00*    (2006.01)
   *G06V 20/56*    (2022.01)
   *G06V 20/10*    (2022.01)
   *G06V 20/68*    (2022.01)

(56) References Cited

U.S. PATENT DOCUMENTS

| | | | |
|---|---|---|---|
| 5,074,203 | A | 12/1991 | Hirtle et al. |
| 7,395,653 | B2 | 7/2008 | de Groot et al. |
| 7,765,780 | B2 | 8/2010 | Koselka et al. |
| 8,136,335 | B2 | 3/2012 | Dobson |
| 8,272,200 | B1 | 9/2012 | Ottaway |
| 10,238,031 | B2 | 3/2019 | D'Arrigo et al. |
| 10,464,217 | B1 | 11/2019 | Phan et al. |
| 2006/0213167 | A1 | 9/2006 | Koselka et al. |
| 2008/0066440 | A1 | 3/2008 | Barnett |
| 2011/0091625 | A1 | 4/2011 | Van Beek |
| 2017/0049051 | A1 | 2/2017 | Cleodolphi |
| 2017/0049054 | A1 | 2/2017 | Molenaar |
| 2018/0263188 | A1 | 9/2018 | Herman et al. |
| 2019/0021230 | A1 | 1/2019 | Bertino |
| 2019/0053427 | A1 | 2/2019 | Matway et al. |
| 2019/0053430 | A1 | 2/2019 | Molenaar |
| 2019/0261566 | A1 | 8/2019 | Robertson et al. |
| 2019/0297778 | A1 | 10/2019 | George et al. |
| 2020/0008355 | A1 | 1/2020 | Nir et al. |
| 2021/0149406 | A1 | 5/2021 | Javault et al. |
| 2021/0337734 | A1 | 11/2021 | Jeanty et al. |
| 2021/0368680 | A1 | 12/2021 | Wisdom et al. |
| 2021/0368685 | A1 | 12/2021 | Wisdom et al. |
| 2021/0368686 | A1 | 12/2021 | Wisdom et al. |
| 2021/0368687 | A1 | 12/2021 | Wisdom |
| 2021/0374894 | A1 | 12/2021 | Wisdom et al. |

FOREIGN PATENT DOCUMENTS

| | | |
|---|---|---|
| NL | 1042547 | 5/2019 |
| WO | WO2017135809 A1 | 8/2017 |

OTHER PUBLICATIONS

Office Action for U.S. Appl. No. 16/885,969, dated Jan. 7, 2022, Wisdom, "End-Effector With Rotary Actuator for Harvesting Crops", 15 Pages.

PCT Search Report and Written Opinion dated Aug. 23, 2021, 10 Pages.

HARVESTING PLANTS BASED ON DETERMINED CRITERIA

CROSS-REFERENCE TO RELATED APPLICATION

This patent application claims priority to U.S. Utility patent application Ser. No. 16/885,911, filed May 28, 2020, which is fully incorporated herein by reference.

BACKGROUND

Several vegetable Crops are normally harvested by hand. Cauliflower, broccoli, or other stemmed vegetables, for example, are usually harvested manually by a crew of workers. As part of this process, workers visually inspect each plant to determine whether the plant is ready for harvesting. Conventional techniques also involve multiple handling stages, which gives rise to bruising or damage. The process of examining, harvesting, and sorting individual plants is labor-intensive, inefficient, and wasteful.

Attempts have been made to automate or semi-automate harvesting. However, given the varying nature of the plants and/or field conditions at a time of harvesting (e.g., size, shape, mud, dust etc.), challenges still remain to observe a harvestable portion of the plant, gripping the plants, and/or separating edible portions from non-edible portions sufficient for automated or semi-automated harvest. Automated harvesting also may require additional manual processing, thus negating some benefits. Further technological improvements may increase harvest yields and efficiencies while reducing waste and manual labor.

BRIEF DESCRIPTION OF THE DRAWINGS

The detailed description is set forth with reference to the accompanying figures. In the figures, the left-most digit(s) of a reference number identifies the figure in which the reference number first appears. The use of the same reference numbers in different figures indicates similar or identical items or features. The systems and devices depicted in the accompanying figures are not to scale and components within the figures may be depicted not to scale with each other.

In FIG. 12A, the end effector is in the closed state.

In FIG. 12B, the end effector is in the open state.

In FIG. 13A, the flipper is in the first position for receiving the harvested edible crowns.

In FIG. 13B, the flipper is in the second position for transferring the harvested edible crowns.

In FIG. 21A, the end effector is in the closed state.

In FIG. 21B, the end effector is in the open state.

In FIG. 21C, the end effector is in the closed state.

In FIG. 21D, the end effector is in the open state.

In FIG. 21E, the end effector is in the closed state.

DETAILED DESCRIPTION

Figure 1:
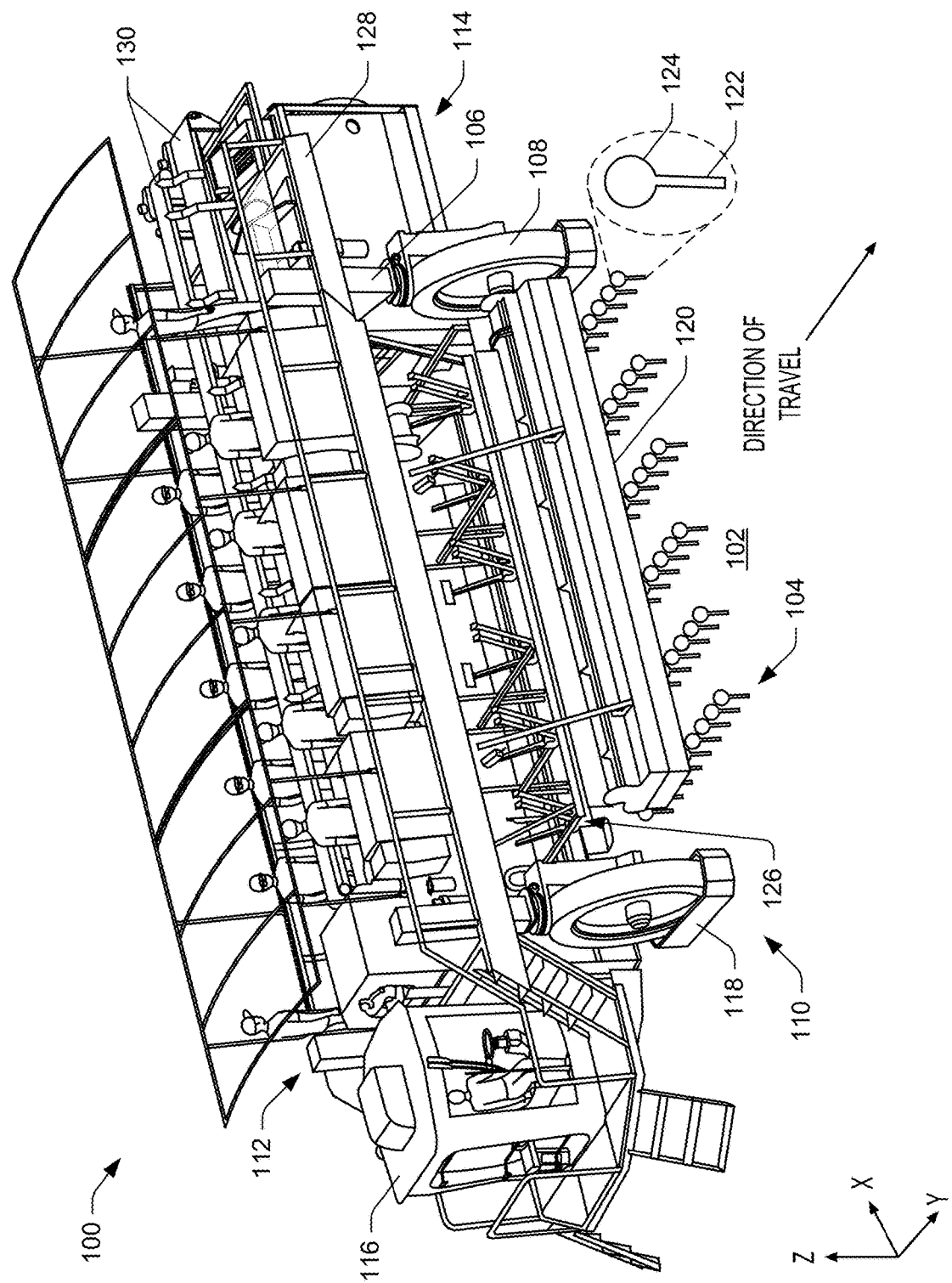
FIG. 1 illustrates a first perspective view of an example harvester for harvesting crops, such as broccoli, according to an embodiment of the present disclosure. In some instances, the harvester may include imaging components for imaging parts of broccoli plants for use in determining whether an edible crown of the broccoli plant is ready for harvesting (e.g., ripe). If ready, harvesting components may harvest (e.g., pick) the edible crown.

Described herein are, among other things, techniques, devices, and systems for determining characteristics of edible crowns using machine learning and determining whether the edible crowns are ready for harvesting. In some instances, a machine or harvester selectively and robotically harvests the edible crowns that are ready for harvesting. The harvester may include sensors, such as an imaging system, for detecting and analyzing characteristic(s) of edible crowns of the broccoli plants (e.g., head, flower, floret, crown, edible portion etc.) for use in controlling mechanical pickers that harvest the edible crowns. For example, the harvester may include robotic arms that may have end effectors that function to mechanically separate the edible crowns from a remainder of the broccoli plant (e.g., the stem, stalk, leaves, etc.). In some instances, the harvester may include any number of robotic arms for harvesting the edible crowns across multiple rows of broccoli plants. As the harvester maneuvers through a field of broccoli plants arranged in rows, the harvester may detect which of the edible crowns are ready for harvesting, remove (e.g., trim, strip, etc.) leaves from the stem and/or around/on the edible crown, separate the edible crown from the rest of the stem, and collect the edible crowns at one or more collection points. The techniques and systems described herein may provide improved efficiencies for harvesting edible crowns, reducing waste, and increasing yields.

In some instances, the harvester may represent a self-propelled automated platform or platform that is towed, pulled, pushed, or carried by a tractor, for example. The platform may provide a space or area occupied by one or more operators, workers, and/or one or more foreman. The harvester may include a body, or frame, having wheels or tracks which engage with the ground for traversing over landscapes or terrain (e.g., crops, fields, etc.). The frame may reside vertically above the broccoli plants such that the broccoli plants pass underneath the frame, between the wheels of the harvester, as the harvester moves about the field. In instances where the harvester is self-propelled, the harvester may include a driving mechanism (e.g., engines, motors, transmissions, gears, generators, etc.) that power the wheels for moving across the field.

A navigational system of the harvester may be utilized to navigate the harvester throughout the field. In some instances, the navigational system may include a global positioning satellite (GPS) system or other location-based tracking system for navigating the harvester throughout the field. In some instances, the navigational system may be used for controlling the harvester and guiding the harvester along a predetermined route or path for harvesting the edible crowns. For example, the predetermined route may include a serpentine path that traverses the rows of broccoli plants within the field. In some instances, the navigational system may communicatively couple to a steering device and/or the driving mechanism for providing instructions and maneuvering the harvester along the predetermined route or path.

In some instances, the harvester may include a de-leafing component that removes leaves of the broccoli plant. For example, broccoli plants typically have an abundance of leaves that grow from the broccoli stem and which reside beneath, alongside of, and even above the edible crown. These leaves may conceal the edible crowns and impact a quality of image(s) obtained of the edible crown. If the leaves were not substantially removed before imaging the crowns, the computing system may inaccurately determine, or be unable to determine, whether the edible crown is ready for harvesting. Accordingly, in some instances, the de-leafing component may be positioned in front of the imaging system, relative to the direction of travel of the harvester, to remove the leaves and isolate or expose the edible crown. Therein, the imaging system may image the edible crown for use by the computing system to determine whether the edible crown is ready for harvesting.

The harvester may be configured to harvest the edible crowns depending on the maturity of individual broccoli plants (or the individual edible crowns). For example, the harvester may selectively harvest the edible crowns based on whether the edible crowns are ripe for picking (e.g., mature, full-grown, etc.). To assist in this process, the harvester includes components for determining whether the edible crowns are ready to be harvested, and in such cases, includes components for harvesting the edible crowns and/or processing the edible crowns (e.g., packaging, cleaning, trimming, etc.). The components may be distributed or mounted across the platform and/or the frame of the harvester. In some instances, the entirety of the process for harvesting the edible crowns may be automated and/or workers may assist in harvesting the edible crowns. For example, the workers may clean and/or package the edible crowns once harvested.

In some instances, the harvester may include an imaging system for detecting harvestable edible crowns within the field. For example, the imaging system may image unharvested rows of broccoli plants within the field as the harvester maneuvers within the field. The imaging system may be positioned vertically above the broccoli plants and arranged to image the edible crowns from above. As the broccoli plants (or the edible crowns) come within a field of view of the imaging system, image(s) of the edible crowns may be captured. In some instances, the imaging system may continuously image the broccoli plants such that a series of images of the edible crowns are obtained. However, in some instances, a single image of individual edible crowns may be obtained.

As the harvester moves across the field the edible crowns of the rows of broccoli plants may come into view of the imaging system and the imaging system may image a succeeding or next edible crown for determining whether the next edible crown is ready for harvesting. In some instances, the imaging system may be at a fixed position on the harvester or the imaging system may be actuatable to position and/or aim at the edible crowns. In some instances, the imaging system may be angled in such a way to capture ensuing or successive edible crowns in a direction of travel of the harvester. In this manner, the harvester may continuously image the edible crowns as the harvester moves about the field.

The harvester may also include lighting element(s) that illuminate the broccoli plants, such as the edible crowns, for obtaining clear images and/or increased image quality. Illuminating the edible crowns may increase the identification of harvestable edible crowns, such as obtaining images depicting a color of the edible crowns and/or a size of the edible crowns (e.g., distinguishing the edible crown from other portions of the broccoli plant and/or the environment). The lighting element(s) may also permit the harvester to be operated in low-light, or no natural light conditions, such as dusk, dawn, and/or at night.

In some instances, the imaging system may include one or more cameras and/or one or more depth sensors for imaging the edible crowns. In some instances, the one or more cameras may include red-green-blue (RGB) cameras and the one or more depth sensors may include infrared (IR) sensors. As the harvester may be configured to harvest more than one row of broccoli plants simultaneously, or edible crowns across multiple rows of broccoli plants, the harvester may include imaging systems for the respective rows. By way of example, the harvester may be configured to simultaneously harvest twelve (or more) rows of broccoli plants, and in such instances, the harvester may include twelve (or more) imaging systems for detecting the harvestable edible crowns within the individual rows of broccoli plants. A first imaging system may image edible crowns within a first row, a second imaging system may image edible crowns within a second row, and so forth. However, in some instances, the imaging systems may image more than one row of broccoli plants, or across rows of broccoli plants. For example, an imaging system may include a first camera for imaging a first row of broccoli plants and a second camera for imaging a second row of broccoli plants. Additionally, or alternatively, a single camera of the imaging system may image a first row of the broccoli plants and a second row of the broccoli plants.

As discussed above, the harvester may be configured to harvest the edible crowns based on the characteristic(s) or properties of the broccoli plant (or the edible crown). For example, based on the imaging performed by the imaging system, a computing system of the harvester may analyze the image(s) for determining characteristic(s) of the individual broccoli plants, or parts thereof (e.g., the edible crown, stem, leaves, etc.). By way of example, using the image(s) captured by the imaging system, the computing system may analyze the image(s) to determine a size, color, condition, quality, health, and/or ripeness of the edible crown. The computing system may be configured to process, in parallel, image(s) captured by the multiple imaging system for determining characteristic(s) of the broccoli plants and whether to respectively harvest edible crowns within the rows of broccoli plants. In some instances, these characteristics may be compared against reference characteristics to determine whether the edible crowns are ready for harvesting.

In some instances, the computing system may determine, based on the characteristic(s), a probability (or score) that the edible crown is ready for harvesting. If the probability satisfies a certain confidence threshold, the edible crown may be deemed or determined ready for harvesting. Additionally, or alternatively, in some instances, to determine the probability, the computing system may utilize machine-learning (ML) model(s). For example, the ML model(s) may be trained from a database (e.g., historical data, such as image data, of past edible crowns that were harvested, or past edible crowns that were not harvested) to analyze the image(s) captured by the imaging system for identifying characteristic(s) of the edible crown, such as color, shape, size, etc. The ML model(s), upon identifying one or more of these characteristic(s), may assess the color, shape, size, etc. in comparison with information stored in the database to determine whether the edible crown is ready for harvesting.

Noted above, the database may be previously trained (e.g., via the ML model(s)) to indicate characteristic(s) of the edible crowns that are associated with edible crowns ready for harvesting. For example, the trained database may indicate a range of colors associated with edible crowns that are ready for harvesting, and upon the ML model(s) determining the color of the edible crown (e.g., average color), the ML model(s) may compare this color to the colors in the database for determining whether the edible crown is ready for harvesting. In some instances, these colors in the database may be considered reference colors to which the identified color by the ML model(s) is compared. However, in some instances, the computing system may additionally or alternatively use a trained database indicative of characteristic(s) of edible crowns that are not ready for harvesting to determine to not harvest edible crown(s).

As part of the ML model(s) analyzing the image(s), the ML model(s) may label characteristic(s) of the edible crown that indicate whether the characteristic is associated with an edible crown that is ready for harvesting. Therein, an output of the ML model(s) may indicate whether the edible crown is ready for harvesting. In some instances, the ML model(s) may determine the characteristics(s) for comparison to respective references for determining whether the edible crown is ready for harvesting. As such, the harvester (or a remotely coupled computing device) may store a database of information indicative of properties of the edible crown that are ready for harvesting.

However, the ML model(s) may use any number of characteristic(s) for determining whether to harvest the edible crown. For example, the ML model(s) may use or determine any number of characteristic(s) or properties of the imaged edible crowns for use in determining whether the edible crowns are ready for harvesting or not ready for harvesting (e.g., one, two, three, four, etc.). In such instances, the ML model(s) may weigh certain characteristics relative to others. For example, a color of the edible crown may be more indicative of the edible crown being ready for harvesting, as compared to a size of the edible crown. As such, after determining characteristic(s) of the imaged edible crown, the characteristic(s) may be compared against reference characteristics to determine whether the edible crown is ready for harvesting. The ML model(s) may output the probability that represents whether the edible crown is ready for harvesting, based on the analyzed characteristic(s).

Utilizing the imaging system, the computing system may therefore assess the maturity, or immaturity, of the edible crowns such that the computing system may differentiate between mature and immature edible crowns. Edible crowns that are mature may be considered harvestable, while edible crowns that are immature may not be deemed harvestable (or not mature for harvesting). For example, because broccoli plants mature at different rates, on a given day, some edible crowns may be ready to harvest while other edible crowns may not be ready to harvest. The edible crowns that are not ready for harvesting are left in the ground for harvesting at a later time. Processing the image(s) captured by the imaging system and using the ML model(s) may therefore be used to select which edible crowns are to be harvested. Knowing which edible crowns are harvestable permits the harvester to selectively harvest these edible crowns. As such, the computing system may cause these edible crowns to be harvested.

For example, and in some instances, the harvester may include automated mechanical components or robotic arms having end effectors, such as a gripper, for harvesting the edible crowns. The robotic arms may be located behind the imaging systems, in a direction of travel of the harvester, such that results of the imaging system may be used to determine whether to harvest the edible crowns. In these sense, the imaging systems may be located in front of robotic arms such that the harvester may first image the edible crowns, and then if ready for harvesting, may harvest the edible crowns using the robotic arms. This allows the computing system to instruct the robotic arms to harvest the edible crowns. Mounting or fixing the imaging systems in this manner also allows the harvester to continuously move across the field and continuously determine whether the edible crowns are ready for harvesting.

The robotic arms may function to pick the edible crowns and separate the edible crowns from other portions of the broccoli plant (e.g., stem). In some instances, the harvester may include any number of robotic arms having the end effectors for harvesting the edible crowns. For example, the harvester may include one or more robotic arms for each row of broccoli plants being harvested (or imaged). In some instances, the harvester may be configured to harvest multiple rows broccoli plants at the same time, using the one or more robotic arms. In this sense, the robotic arms may be configured to harvest individual edible crowns from broccoli plants of a particular row, or the harvester may include any number of robotic arms for harvesting the edible crowns from any number of rows. For example, in instances where the harvester is configured to harvest twelve rows of broccoli plants, the harvester may include a first robotic arm for harvesting the broccoli plants within a first row, a second robotic arm for harvesting the broccoli plants within a second row, and so forth. However, in some instances, the robotic arms may harvest across rows of broccoli plants. For example, a particular robotic arm may harvest edible crowns within the first row and the second row, or two robotic arms may harvest edible crowns across the first row and the second row.

Each robotic arm may include a mechanical device for picking the edible crowns and cutting the edible crown from the stem. For example, the end effector of the robotic arm may represent a gripper that is moveable between an open state and a closed state. The end effector may include limbs, members, or fingers that enclose around the edible crown in the closed state, and which are sized to receive the edible crown without bruising or otherwise damaging the edible crown. In some instances, actuators may open and close the fingers of the end effector, between the open state and the closed state. When open, the fingers may be spaced apart by distances that allows the end effector to descend over or upon the edible crown. The end effector, via fingers, converge upon and grasp the broccoli stem in the closed state. When closed, the end effector may include an interior space or cavity occupied by the edible crown.

The fingers may include shapes and sidewalls for receiving and supporting the edible crown once cut from the broccoli stem. The end effector may include a cutting mechanism (e.g., blade, saw, knife, etc.) for severing the edible crown from the broccoli stem. In some instances, the cutting mechanism may represent an actuatable rotary blade that rotationally cuts through the broccoli stem, or may represent a single guillotine blade and/or double guillotine blade that linearly cuts through the broccoli stem. After the edible crown is cut from the broccoli stem, the edible crown may remain cradled in the end effector, within the fingers, for transporting to other portions of the harvester for processing and/or collection. In some instances, the end effector may include two, four, or any number of fingers. Additionally, in some instances, once the cutting mechanism cuts through the broccoli stem, the cutting mechanism (i.e., the blade) may remain in position to support the edible crown in the end effector. For example, the cut broccoli stalk may rest on the blade to support the edible crown within an interior of the end effector.

When the computing system classifies, tags, or otherwise identifies an edible crown as being ready for harvesting, the robot arm may maneuver or position to the edible crown. In some instances, positioning the robotic arm may involve moving the end effector over (e.g., above) the edible crown. In some instances, the robotic arm may be configured to move the end effector along, or in, multiple planes. In some instances, the robotic arm and/or the end effector may be coupled to the positioning system (e.g., tracks rails, motors, etc.) that effectuates to position the end effector relative to the edible crown. The end effector may therefore have multiple degrees of freedom to accommodate for the varying characteristic(s) of the broccoli plants. For example, as broccoli plants often do not grow in straight lines and are also not always vertical, the end effector may be moved to be centered or positioned relative to the edible crown being harvested. The edible crowns may also not stand at a uniform height above the ground, making it impractical to cut the broccoli stems at a given height above the ground. The robotic arm may therefore include actuators that are configured to position the end effector for harvesting the edible crown.

In some instances, the harvester may utilize the imaging system for positioning the end effector. For example, in addition to using the imaging system to detect harvestable edible crowns, the image(s) may also be used to determine a central point of the broccoli plant (or of the edible crown). For example, the image(s) may be analyzed to determine a size of the edible crown (e.g., diameter, height, volume, etc.), and correspondingly the central point of the edible crown within coordinate space. This central point may be used, at least in part, for positioning the end effector.

In some instances, the computing system may determine a range coordinates associated with the edible crown. The range of coordinates (X and Y) may represent an area within coordinate space. This range of coordinates may correspond to the edible crown, and from this range, the central point of the edible crown along one or more axes may be determined. For example, the central point may be represented in X and Y coordinate space and may be used to position the end effector above the edible crown. Furthermore, as part of analyzing the image(s), the computing system may determine a depth (Z-direction) of the edible crown. This depth may be used when instructing the end effector to descend upon the edible crown (e.g., towards the ground).

In some instances, the central point may be determined for each harvestable edible crown and the central point may be utilized for aligning the end effector along multiple planes (or axes). For example, the central point may be a center of the edible crown (e.g., center of mass, center of area/volume, etc.). In some instances, the central point may first be used to position the end effector vertically above the edible crown, and then second, to lower the end effector towards the edible crown to converge upon the edible crown. In some instances, the end effector may be lowered to a certain position for cutting a certain amount of broccoli stalk. For example, depending on consumer preferences, the harvested edible crown may include different lengths of stalks attached thereto.

To illustrate, after determining a harvestable edible crown, the computing system may determine that the center point of the edible crown is located at $X_1$, $Y_1$, and $Z_1$ in coordinate space. The computing system may instruct the robotic arm (or other components) to move the end effector (or move the robotic arm) to align the end effector along a first horizontal axis/plane (e.g., X-axis/X-plane) of the edible crown corresponding to $X_1$. In this position, the end effector may be aligned with the center point of the edible crown in a first direction. Subsequently, or continuously, the computing system may instruct the robot arm to move the end effector to align the end effector along a second horizontal axis/plane (e.g., Y-axis/Y-plane) of the edible crown corresponding to $Y_1$. In this position, the end effector may be aligned with the center point of the edible crown in the first direction and a second direction. That is, once positioned above the edible crown, at $X_1$, $Y_1$, the end effector may be substantially concentric or aligned with the center of the edible crown along two axes, or planes (e.g., X-axis/X-plane and Y-axis/Y-plane).

Once positioned above the edible crown, the computing system may instruct the robot arm to descend the end effector, in the open state, upon the edible crown. In some instances, the end effector may descend by a distance (in the Z-direction) such that once the end effector is closed around the edible crown, the end effector (or the fingers of the end effector) grasps the broccoli stem at a position under the edible crown. In some instances, the end effector may descend a predetermined distance relative to the center point of the edible crown, or relative to the $Z_1$ coordinate of the edible crown. Once the end effector descends upon the edible crown, the fingers may be actuated by the robotic arm to enclose the edible crown.

Once grasped, the cutting mechanism may cut the edible crown from the broccoli stem. For example, the cutting mechanism may include a rotatable blade or blade that linearly cuts through the broccoli stem. In some instances, the cutting mechanism may cut the broccoli stem at a position below (e.g., towards the ground) where the fingers grasp the broccoli stem (e.g., outside the cavity of the end effector in which the edible crown resides). The cutting mechanism therefore severs the edible crown from the broccoli stem while the edible crown is retained within the end effector. Noted above, the amount of broccoli stalk (or stem) left attached to the harvested edible crown may be varied and/or programmable. When the broccoli stem of the encapsulated edible crown has been cut, the edible crown is retained within the end effector and transported for discharge to one or more collection points. For example, the actuators that are utilized to position the robotic arm (or the end effector) may be used to maneuver the robotic arm to a collection point whereby the end effector transitions to the open state and deposits the harvested edible crown.

In some instances, the end effector, and particularly the fingers, may be utilized to strip leaves from the broccoli stems. For example, once the end effector grasps the broccoli stem and before the cutting mechanism cuts the broccoli stem, the robotic arm may descend the end effector downward towards the ground (away from the edible crown). By descending the end effector downward, with the gripper in the closed state, or partially closed state, the fingers may scrape or traverse along the broccoli stem. In some instances, this movement may cause the end effector (or the fingers) to strip the leaves away from the edible crown to dispose of foliage adjacent the edible crown. For example, the fingers, such as sidewalls thereof, may deflect or displace the leaves (or other foliage) away from the edible crown and effectuate to break the leaves away from or strip the leaves from the broccoli stem. After descending a predetermined distance, the end effector may ascend upward before reaching a position whereby the cutting mechanism cuts the broccoli stem below the edible crown. In some instances, the end effector may additionally or alternatively strip the leaves while the fingers are still in the open state but moving towards the closed state.

As noted above, after being cut, the edible crown may be moved to one or more collection points. For example, the robotic arm may move the edible crown to a collection point for unloading the edible crown from the end effector. In some instances, the one or more collection points may represent a bin, or other container, configured to receive edible crowns. Additionally, or alternatively, the one or more collection points may be a conveyor belt for transporting the harvested edible crowns to other portions of the harvester. Regardless, at the one or more collection points, the end effector transitions to the open state and the fingers are opened to release the edible crowns.

In some instances, the use of the end effector, including the fingers and the cutting mechanism, may contribute to the efficiency of the harvester. For example, integrally forming the cutting mechanism within the end effector may reduce a number of components, and lead to an increase or accuracy in severing the edible crown from the broccoli stem. Fewer parts for the end effector, as compared to existing harvesters, may also reduce maintenance to keep the end effector in proper working condition.

As discussed above, the harvester may continuously move across the field and the robotic arms may continuously harvest the edible crowns while the harvester is in motion. In some instances, to account for the movement of the harvester, the robotic arms may be configured to move in relation, or relative, to the harvester. For example, the robotic arm may move in relation to the harvester and based on the speed of the harvester to account for the movement of the harvester across the field. This may, in some instances, include the robotic arm moving in a direction different from (e.g., opposite) a direction of travel of the harvester to remain centered above the edible crown. As the harvester travels along the rows, the robot arms may maintain the position of the end effector relative to the edible crown to compensate for the continuous movement of the harvester.

In some instances, the harvester may perform different types or multiple types of cuts based on characteristic(s) of the broccoli plant. For example, certain types of cuts may be performed based on a diameter (or largest cross-sectional dimensions) of the edible crown. For example, a first type of cut may be performed if the diameter of the edible crown is within a first range of sizes, such as 4.0 and 4.75 inches. The first type of cut may involve the harvester, via the end effector and the cutting mechanism, only cutting the edible crown from the broccoli stem. Alternatively, a second type of cut may be performed if the diameter of the edible crown is within a second range of sizes, such as 4.75 and 5.75 inches. The second type of cut may involve the harvester, via the end effector and the cutting mechanism, stripping the leaves around the edible crown and then cutting the edible crown from the broccoli stem. In some instances, the second type of cut may be performed for edible crowns having a diameter over 4.75 inches. As such, the harvester may perform different operations for harvesting the edible crown based on a diameter (or other characteristic(s)) of the edible crown.

Although the discussion herein relates to harvesting broccoli, or processes of harvesting broccoli, the harvester may be utilized to harvest other crops, such as other standing or stalk-based vegetable crops (e.g., cauliflower, asparagus, celery, lettuce, etc.). In such instances, the harvester or portions thereof may be modified to handle larger or differently shaped plants, and a ML model(s) may be trained on images of these other types of crops for selective harvesting. Accordingly, it is to be appreciated that the term "broccoli" may be interchanged with other types of crops (or plants) throughout this disclosure.

The present disclosure provides an overall understanding of the principles of the structure, function, device, and system disclosed herein. One or more examples of the present disclosure are illustrated in the accompanying drawings. Those of ordinary skill in the art will understand and appreciate that the devices, the systems, and/or the methods specifically described herein and illustrated in the accompanying drawings are non-limiting embodiments. The features illustrated or described in connection with one embodiment, or instance, may be combined with the features of other embodiments or instances. Such modifications and variations are intended to be included within the scope of the disclosure and appended claims.

FIG. 1 illustrates an example harvester 100 for harvesting broccoli. The harvester 100 may be configured to operate within a field 102 containing a plurality of broccoli plants 104 that are grown in rows. As the harvester 100 traverses or moves across the field 102, the harvester 100 functions to harvest the broccoli plants 104. As shown, and as discussed herein, the harvester 100 includes components to harvest the broccoli plants 104 across multiple rows.

The harvester 100 includes a frame 106 that supports components of the harvester 100 or to which components of the harvester 100 mount, couple, or are disposed. The frame 106 may, in some instances, comprise a body and provide a platform for supporting the components of the harvester 100, as will be discussed herein.

The harvester 100 includes wheels 108 for elevating the frame 106 above the field 102 and the broccoli plants 104, and for moving the harvester 100 about the field 102. In some instances, the wheels 108 may be disposed at each corner (or substantially at each corner) of the harvester 100 (or the frame 106). Additionally, or alternatively, the wheels 108 may be disposed on opposing ends or sides of the harvester 100. For example, in some instances, the harvester 100 may include a first side 110 and a second side 112, spaced apart from the first side 110 in the Y-direction. The first side 110 may include two of the wheels 108 that couple or mount to a first side of the frame 106 and the second side 112 may include two of the wheels 108 that couple or mount to a second side of the frame 106. However, in some instances, the harvester 100 may include less than or more than four wheels or the wheels 108 may be located on the harvester 100 differently than shown. For example, the wheels 108 may be spaced farther apart or may be spaced closer together. Additionally, or alternatively, the harvester 100 may include continuous tracks (e.g., rubber), or a track system, for driving the harvester 100.

The wheels 108 may be spaced apart or offset from one another such that the wheels 108 are positioned in between rows of the broccoli plants 104. For example, as shown, each of the rows of the broccoli plants 104 may be separated by a predetermined distance (e.g., in the X-direction). This predetermined distance may be determined or known during planting of the broccoli plants 104. By way of example, the predetermined distance may be eight inches, ten inches, twelve inches, or any other distance. Interposed between the rows, the broccoli plants 104 are not planted, and hence, driving the wheels 108 within this gap does not damage the broccoli plants 104 or reduce a harvestable yield of the broccoli plants 104. Therefore, the size of the wheels 108 and/or the distance at which the wheels 108 are spaced apart from one another may accommodate the size of the broccoli plants 104 as well as the spacing in between the rows of broccoli plants 104.

The wheels 108 may operably couple to a driving mechanism of the harvester 100, such as a motor or engine (e.g., combustion and/or electrical). Additionally, or alternatively, the harvester 100 may be solar-powered, battery powered, and/or a combination thereof. The motor and the coupling of the motor to the wheels (e.g., transmission, differential, gearbox, linkages, pneumatics, etc.) forms a drivetrain that powers the harvester 100 across the field 102. In some instances, the harvester 100 includes a centralized motor that powers all of the wheels 108. However, in some instances, each of the wheels 108 may include their own electrical motor that is powered by a generator 114 of the harvester 100. The wheels 108 may therefore be independently actuatable by a respective motor.

In some instances, the individual motors may be located on a hub of the individual wheels 108, and may receive power from the generator 114 for powering the wheels 108. The individual motors may power each of the wheels 108 at respective speeds. Additionally, the wheels 108 may be configured to be powered in one or more directions (e.g., clockwise and counterclockwise, forward and reverse, etc.)

for directing the harvester 100 forward and backwards. Independently powering each of the wheels 108 may also increase a maneuverability of the harvester (e.g., turning radius) to make minor adjustments in steering the harvester 100 within the field 102 and directing the harvester 100 along a predetermined route within the field 102.

Additionally, or alternatively, each of the wheels 108 may be steerable. In some instances, the wheels 108 may be rotated 180 or 360 degrees (about Z-axis). For example, in the case that the harvester 100 includes four wheels, each of the wheels 108 may be steerable (e.g., four-wheel steering). The independent steering of the wheels 108, as well as independently powering each of the wheels 108, allows the harvester 100 to turn or position across the field 102 in real-time and make minor adjustments to positioning. This sharp turning increases a maneuverability of the harvester 100.

In some instances, the harvester 100 may be controlled or operated via a cabin or cockpit 116. The cockpit 116 includes an operator who operates and controls the harvester 100. For example, within the cockpit 116, the operator may steer the harvester 100 or may control a speed and/or direction of the harvester 100 within the field 102. The operator may also control an amount of power supplied to each of the wheels 108 for steering the harvester 100. Within the cockpit 116, the operator may also utilize various instruments, gadgets, panels, and so forth for controlling the operation of the harvester 100. For example, a panel within the cockpit 116 may illustrate a route for harvesting the broccoli plants 104, an amount of the broccoli plants 104 that are being harvested, a status of the harvester 100, and so forth.

As will be discussed herein, the harvester 100 may travel in more than one direction for harvesting the broccoli plants 104. For example, the wheels 108 may rotate clockwise to propel the harvester 100 in a first direction of travel (e.g., as shown in FIG. 1), and subsequently, the wheels 108 may rotate counterclockwise to propel the harvester in a second, opposite direction. Alternatively, the wheels 108 may be powered in an opposite direction without rotating the wheels 108. To accommodate for this multi-directional movement, a seat within the cockpit 116 may be adjustable to swivel and the operator may face a respective direction of travel. In such instances, the cockpit 116 may include more than one set of panels, gadgets, instruments, and/or a steering wheel for controlling the harvester 100.

FIG. 1 further illustrates, that in some instances, skirts 118 may be placed around the wheels 108. The skirts 118, in some instances, may prevent build-up of dirt, mud, or other debris on the wheels 108. For example, the skirts 118 may come into close proximity with a sidewall and/or outer periphery of the wheel 108 (or a tire thereof) to scrape or deflect mud build-up. As discussed herein, in some instances, the wheels 108 or portions of the harvester 100 may include an encoder for tracking a distance the harvester 100 travels. This distance may be used to determine a position of the harvester 100 within the field 102 and/or a position of a harvestable edible crown within the field 102. However, the build-up of mud or other debris may impact an accuracy in determining a distance traveled by the harvester 100 (e.g., slippage, diameter of the wheel 108, etc.). As such, the skirts 118 may function to reduce this build-up, which may be used to accurately determine a position of the harvester 100 and/or the edible crowns ready for harvesting. However, as also discussed herein, other positioning systems (e.g., Global Positioning Satellite (GPS)) may be used for tracking and/or determining a location of the harvester 100 within the field 102.

The harvester 100 may include an assembly or a hood 120 that extends from the frame 106. Further details of the hood 120 are discussed herein. Generally, the hood 120 functions to image the broccoli plants 104 and if the broccoli plants 104 are ready for harvesting (e.g., ripe), components of the harvester 100 pick or harvest the individual broccoli plants 104. The hood 120 is shown extending from the frame 106, or being supported by the frame 106, and disposed above a ground surface.

In some instances, the hood 120 may couple to the frame 106, or other portions of the harvester 100, using pneumatic cylinders to raise and lower the hood 120 relative to the field 102 and/or the broccoli plants 104. For example, when not in use, the hood 120 may be raised (Z-direction) so as to be in closer proximity to the frame 106 than as shown in FIG. 1, elevated above the field 102. However, in some instances, the hood 120 may rigidly couple to the frame 106.

In some instances, the hood 120 may include a rectangular shape. The hood 120 is shown being disposed between the wheels 108 of the harvester 100 on the first side 110. A gap distance may be disposed between the wheels 108 and ends of the hood 120 to allow the wheels 108 to rotate (e.g., about the Z-axis) without contacting or abutting the hood 120.

As shown, the broccoli plants 104 may pass underneath the hood 120 as the harvester 100 moves in the direction of travel. As shown in FIG. 1, six rows of the broccoli plants 104 are configured to pass underneath the hood 120 at a given time. The harvester 100 may therefore be configured to harvest six rows of the broccoli plants 104 simultaneously or at the same time. However, the harvester 100 may be scaled to harvest more than or less than six rows of the broccoli plants 104 at a single time or instance. For example, the harvester 100 may include components for harvesting twelve rows of broccoli plants 104 at the same time. In such instances, the harvester 100 may include components and/or features to account for the increased harvesting, such as a lengthened frame, one or more additional wheels, and so forth.

Furthermore, although FIG. 1 illustrates a particular arrangement of the rows of the broccoli plants 104, the harvester 100 may be configured to harvest rows of the broccoli plants 104 that have different characteristics. For example, the broccoli plants 104 may not be planted in a straight line (e.g., zig-zag, curved, etc.), the rows of the broccoli plants 104 may be spaced closer together, the rows of the broccoli plants 104 may be spaced farther apart, the rows of the broccoli plants 104 may not be evenly spaced apart, the individual broccoli plants 104 may not be evenly spaced apart from one another within the same row, or in some instances, multiple rows of the broccoli plants 104 may be planted in close proximity to one another and spaced apart by a greater distance from other rows. For example, two rows of the broccoli plants 104 may be planted in close proximity, with minimal spacing therebetween, and these two rows may be spaced apart from an additional two rows. To accommodate for these variables and changing characteristics, as will be discussed herein, the harvester 100 may be configured to harvest a multitude of the broccoli plants 104 according to their arrangement and planting within the field 102.

The hood 120 is shown being disposed vertically above the broccoli plants 104 (Z-direction) for imaging the broccoli plants 104 as the broccoli plants 104 pass underneath the hood 120 and as the harvester 100 moves in the direction of travel. Generally, the broccoli plants 104 include a stalk 122 growing upwards from the ground and buds that grow on an end thereof, above the ground. The buds form an edible crown 124 that is harvested for consumption. The edible crown 124 may correspond to a portion of the broccoli plants 104 that are harvested for consumption. In some instances, the edible crown 124 may be referred to as a head of the broccoli plant 104, a floret of the broccoli plant 104, a flower of the broccoli plant, or an edible portion of the broccoli plant 104.

The edible crown 124 of the individual broccoli plants 104 may be imaged and this imaging, or the image(s) generated by imaging device(s) and/or system(s) of the harvester 100, may be utilized to determine whether to harvest the broccoli plants 104. For example, image analysis and/or ML model(s) may be used to determine whether the broccoli plants 104 are ready for harvesting (e.g., ripe, mature, etc.). If so, components of the harvester 100 may harvest the broccoli plants 104 (e.g., the edible crowns 124). For example, and in some instances, the harvester 100 may include robotic arms having actuatable end effectors and/or cutting mechanisms that harvest the broccoli plants 104.

By way of example, and in instances where the harvester 100 is configured to harvest six rows of the broccoli plants 104 simultaneously, the harvester 100 may include six imaging devices (e.g., cameras and/or IR sensors) and six robotic arms having the end effectors and/or cutting mechanisms. The six imaging devices may image a respective row of the broccoli plants 104, while the six end effectors of the six robotic arms may pick the broccoli plants 104, respectively, and the six cutting mechanisms of the six end effectors may cut (harvest) respective broccoli plants 104. The robotic arms may be independently actuatable and controlled for harvesting the edible crowns 124 within the respective rows of broccoli plants 104. However, in some is instances, the imaging devices may image the broccoli plants 104 across one or more rows and/or or the end effectors may pick the edible crowns 124 across one or more row of the broccoli plants 104.

In some instances, the imaging devices may be secured within the hood 120, or on a bottom surface of the hood 120. In some instances, the imaging devices may be stationary or may be movable or actuatable in one or more directions (e.g., X-direction, Y-direction, Z-direction) and/or one or more degrees of rotation (e.g., tilt, pan, yaw) for capturing the image(s) of the broccoli plants 104.

As noted above, robotic arms of the harvester 100 may harvest the edible crowns 124 and/or include components for harvesting the edible crowns 124. In some instances, the robotic arms may include actuators, a suspension system, or members that are configured to position the end effectors relative to the broccoli plants 104. For example, FIG. 1 illustrates one or more robotic arms 126 that extend from the frame 106, downward (Z-direction), and which couple to respective end effectors. The robotic arms 126, additionally or alternatively, may extend from other portions of the harvester 100, such as the hood 120. In some instances, a first end of the robotic arms 126 may couple to the frame 106 (or the hood 120), while a second end of the robotic arms 126 may couple to the end effector for positioning the end effector relative to the individual broccoli plants 104 that are ready for harvesting. In this sense, the robotic arms 126 may articulate or position to locate the end effectors.

The end effectors are configured to harvest the broccoli plants 104, and specifically, the edible crown 124 of the broccoli plants 104. The edible crown 124 may be grasped by the end effector, cut from the stalk 122, and transferred to a collection location on the harvester 100. For example, in some instances, the end effectors may transfer the harvested edible crowns 124 to a conveyor belt or other transfer mechanism, (e.g., flipper, chute, escalator, etc.) that transfers the harvested edible crowns 124 to other portions of the harvester 100.

In some instances, the harvester 100 may include more than one hood 120, the harvester 100 may be designed to travel in multiple directions. For example, the second side 112 of the harvester 100 may include a second hood that includes similar components as the hood 120 and/or the second side 112 of the harvester 100 may include similar components as the first side 110. Including a second hood may increase a harvesting yield of the broccoli plants 104, increase a universalness of the harvester 100, and/or increase a rate of harvesting. For example, the second hood on the second side 112 may be utilized when the harvester 100 travels in a second direction, opposite the direction of travel as shown in FIG. 1. For instance, upon the harvester 100 reaching the end of the field 102 or the rows of the broccoli plants 104, the harvester 100 may utilize the second hood for imagining the broccoli plants 104 in lieu of the hood 120. This may avoid the harvester 100 having to perform wide turns at the end of the field 102. Instead, the harvester 100 may steer the wheels 108 to additional rows (e.g., by driving the harvester 100 in the X-direction of FIG. 1), without having to perform wide "U-turns" and then travel in a direction opposite the direction of travel. In such instances, the second hood may be used to image broccoli plants 104 within additional rows and the robotic arms 126 may pick and harvest these broccoli plants 104. The harvester 100 may therefore travel in multiple directions for harvesting the broccoli plants 104, where the harvester 100 may include the robotic arms 126 that are configured to operate in conjunction with the imaging performed by the harvester 100, whether by the hood 120 and/or an additional hood.

The harvester 100 is shown including a platform 128 on which personnel stand. The personnel may perform further processing on the harvested edible crowns, such as cleaning, removing leaves, sorting (e.g., size, color, shape, maturity, etc.), discarding, repurposing, and so forth. For example, after the edible crowns are harvested, transfer mechanisms (e.g., conveyor belt, ladder, escalator, lift, etc.) may transfer the edible crowns to the platform 128. In some instances, the transfer mechanisms may transfer the edible crowns to conveyor belts 130 on the platform 128. For example, FIG. 1 illustrates that the platform 128 may include two conveyor belts 130. A first of the conveyor belts 130 may be operated by a first portion of the personnel, while a second of the conveyor belts 130 may be operated by a second portion of the personnel. As the conveyor belts 130 operate, edible crowns may pass along the conveyor belts 130 and the personnel may inspect the edible crowns. Additionally, or alternatively, the personnel may box or package the edible crowns for shipment or distribution.

The frame 106, or the platform 128, may further include guardrails for safety, a canopy to provide shade and/or shelter for the personnel, bins or cabinets for storing supplies (e.g., boxes, gloves, etc.), and/or ladders for allowing the platform 128 to be entered and exited.

The harvester 100 is therefore configured to operate while traversing across the field 102 without stopping. For example, as the wheels 108 power and/or steer the harvester 100, the broccoli plants 104 are imaged by the imaging devices for use in determining whether to harvest the edible crowns 124. Subsequently, the robotic arms 126 may pick and harvest the edible crowns 124 that are ready. The harvester 100 may therefore continuously image the edible crowns 124 and pick the edible crowns 124 that are ready for harvesting, all while the harvester 100 moves about this field 102. Such continuous movement (e.g., half a mile per hour, one mile per hour, two miles per hour, etc.) may increase yields and reduce harvesting times. Moreover, the harvester 100 may be configured to travel at respective speeds based on a density of harvestable edible crowns or the number of rows the harvester 100 is configured to harvest.

Furthermore, although the discussion herein relates to harvesting edible crowns 124 of the broccoli plants 104, the harvester 100 may be configured or utilized to harvest other crops, such as lettuce, cauliflower, asparagus, brussels sprouts, and so forth. In such instances, the harvester 100 may be equipped with suitable equipment, imaging devices, robotic arms (pickers), end effectors, and so forth.

In some instances, although the harvester 100 is discussed herein as being a self-propelled machine, the harvester 100 may be configured to be towed, pulled, or carried by a tractor, for example. In such instances, the components of the harvester 100 may be powered and/or driven by components of the tractor. For example, components of the harvester 100 may be driven by hydraulic motors powered by a hydraulic pump driven from a power take off (PTO) of the tractor. Additionally, or alternatively, electrical components within the harvester 100 may be powered from an electrical system of the tractor, or via onboard generator of the harvester 100.

Figure 2:
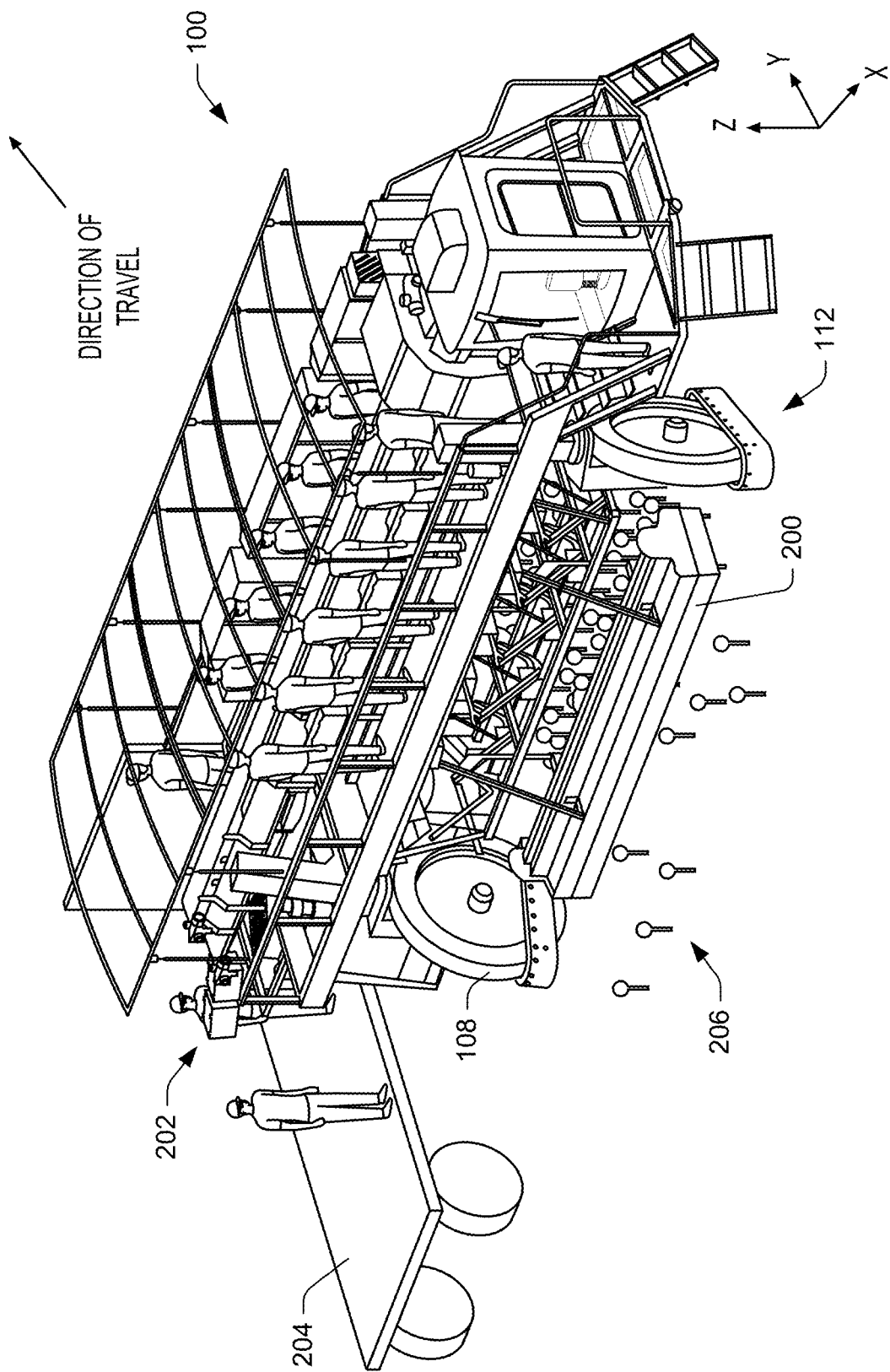
FIG. 2 illustrates a second perspective view of the harvester of FIG. 1, according to an embodiment of the present disclosure.

FIG. 2 illustrates an additional view of the harvester 100. For example, FIG. 1 illustrated the first side 110 of the harvester 100, moving in the direction of travel, while FIG. 2 illustrates the second side 112 of the harvester 100 while the harvester 100 is moving in the direction of travel. In this sense, the view illustrated in FIG. 2 may illustrate a back or trailing side, relative to FIG. 1, as the harvester 100 moves in the direction of travel.

As discussed above, the harvester 100 may include the wheels 108 located on the second side 112 and/or an additional hood 200. For example, as the harvester 100 travels in an opposite direction of travel (opposite to the direction of travel shown in FIGS. 1 and 2), the additional hood 200 may be used for harvesting the broccoli plants 104. For example, when the harvester 100 is moving in the direction of travel as shown in FIG. 2, the additional hood 200 may not be in use for imaging and/or otherwise harvesting the broccoli plants 104. In some instances, the additional hood 200 may be raised to an elevated position when not in use using pneumatic cylinders and/or arms. In some instances, as the harvester 100 travels in the indicated direction of travel (Y-direction), the additional hood 200 may be on a trailing side, opposite a leading side, where the hood 120 is located. In some instances, the additional hood 200 on the trailing side may be used in conjunction with the hood 120 on the leading side for redundancy purposes (e.g., for imaging edible crowns 124 and/or harvesting edible crowns 124 that might have been missed by the hood 120) or to image those edible crowns 124 that were not harvested and/or which were not ready for harvesting.

FIG. 2 also illustrates that as the harvester 100 picks the edible crowns 124 from the broccoli plants 104, and after the personnel processes or boxes the edible crowns 124, packages 202 may be transferred to an awaiting vehicle 204 (or trailer). In some instances, the conveyor belts 130 may carry or transfer the packages to personnel on or operating the vehicle 204. The personnel may stack the packages on a bed of the vehicle 204 for shipment.

In some instances, the packages 202 may be transferred to the vehicle 204 while the harvester 100 is moving, or the harvester 100 may park to offload the packages 202. However, transferring the packages 202 to the vehicle 204 while the harvester 100 is harvesting the edible crowns 124 may permit uninterrupted harvesting of the edible crowns 124.

As shown in FIG. 2, some of the broccoli plants 104 may not be harvested. For example, as the imaging devices image the broccoli plants 104, some of the edible crowns may not be ready for harvesting. By way of example, the edible crowns 124 may be of insufficient size, color, shape, density, or maturity. If the edible crowns 124 are not ready for harvesting (e.g., not mature, not ripe, etc.), the harvester 100 may not harvest these edible crowns and as such, unharvested broccoli plants 206 (of the harvested broccoli plants 104) may remain planted in the field 102. In other words, the robotic arms 126 may not be instructed to pick certain edible crowns of the broccoli plants 104 (e.g., those edible crowns corresponding to the unharvested broccoli plants 206). However, the robotic arms 126 are instructed to harvest those edible crowns of the broccoli plants 104 that are ready for harvesting.

The unharvested broccoli plants 206 may therefore remain planted for harvesting at a later instance. In some instances, the harvester 100 may record a location of the unharvested broccoli plants 206. This recorded location may be used at a later instance to locate the unharvested broccoli plants 206 within the field 102. In other instances, the harvester 100 may record characteristic(s) of the unharvested broccoli plants 206 that are not harvested (e.g., size, color, shape, etc.) and may project, based on these characteristic(s), when the edible crowns of the unharvested broccoli plants 206 will be ready for harvesting. Such determination may be used at a later instance for harvesting the unharvested broccoli plants 206. Additionally, or alternatively, images of the unharvested broccoli plants 206 may be used to train (or re-train) ML model(s). For example, knowing characteristic(s) of the unharvested broccoli plants 206 may increase an accuracy of the ML model(s) determining or recognizing those broccoli plants that are ready for harvesting and/or not ready for harvesting.

Additionally, or alternatively, in some instances, the additional hood 200 may determine, among the broccoli plants 104, the unharvested broccoli plants 206. For example, image(s) captured by the imaging devices of the additional hood 200 may be used to determine a location of the unharvested broccoli plants 206 and/or characteristics of the unharvested broccoli plants 206, for use in determining when the unharvested broccoli plants 206 will be ready for harvesting.

Figure 3:
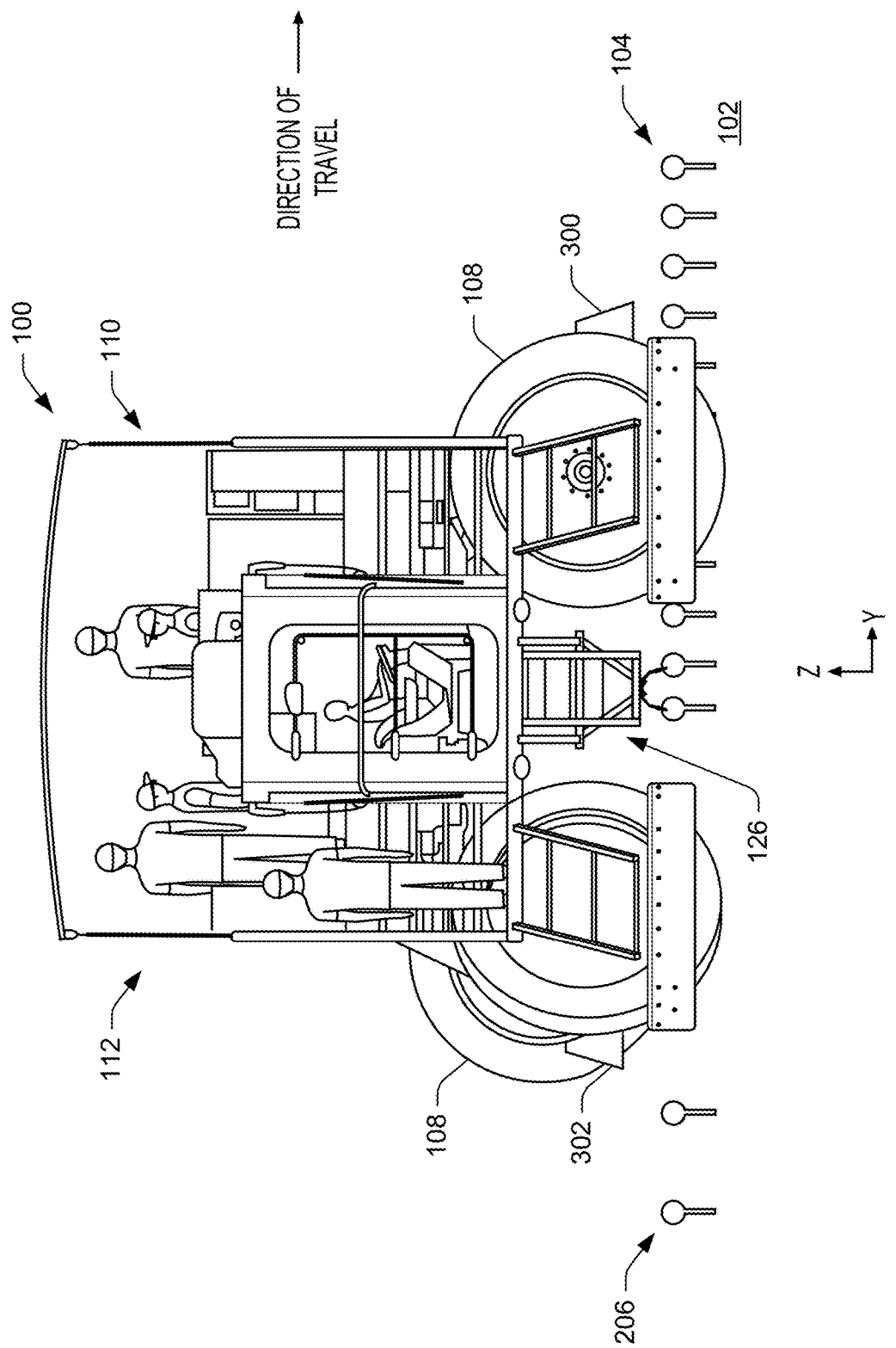
FIG. 3 illustrates a first side view of the harvester of FIG. 1, according to embodiment of the present disclosure.

FIG. 3 illustrates a side view of the harvester 100. As shown, the harvester 100 travels in the direction of travel for harvesting certain edible crowns 124 of the broccoli plants 104.

As discussed previously, the harvester 100 may include two hoods for imaging the edible crowns 124. For example, the harvester 100 may utilize a first hood 300 (e.g., the hood 120) as the harvester 100 travels in the direction of travel for imaging the edible crowns 124. A second hood 302 (e.g., the additional hood 200) may be utilized by the harvester 100 when traveling in a direction opposite to the direction of travel. In this sense, the harvester 100 may not include a designated "front" or "back" but may travel in multiple forward directions.

Between the first hood 300 and the second hood 302, or between the wheels 108 on the first side 110 and the wheels 108 on the second side 112 may be an internal space occupied by the robotic arms 126. The robotic arms 126, as discussed above, may descend from the frame 106 or other portions of the harvester 100 for harvesting the edible crowns 124 as the broccoli plants 104 pass under the first hood 300 and are flagged for harvesting.

The wheels 108 of the harvester 100 are further shown being turned at various angles or orientations to navigate the harvester 100 throughout the field 102.

Figure 4:
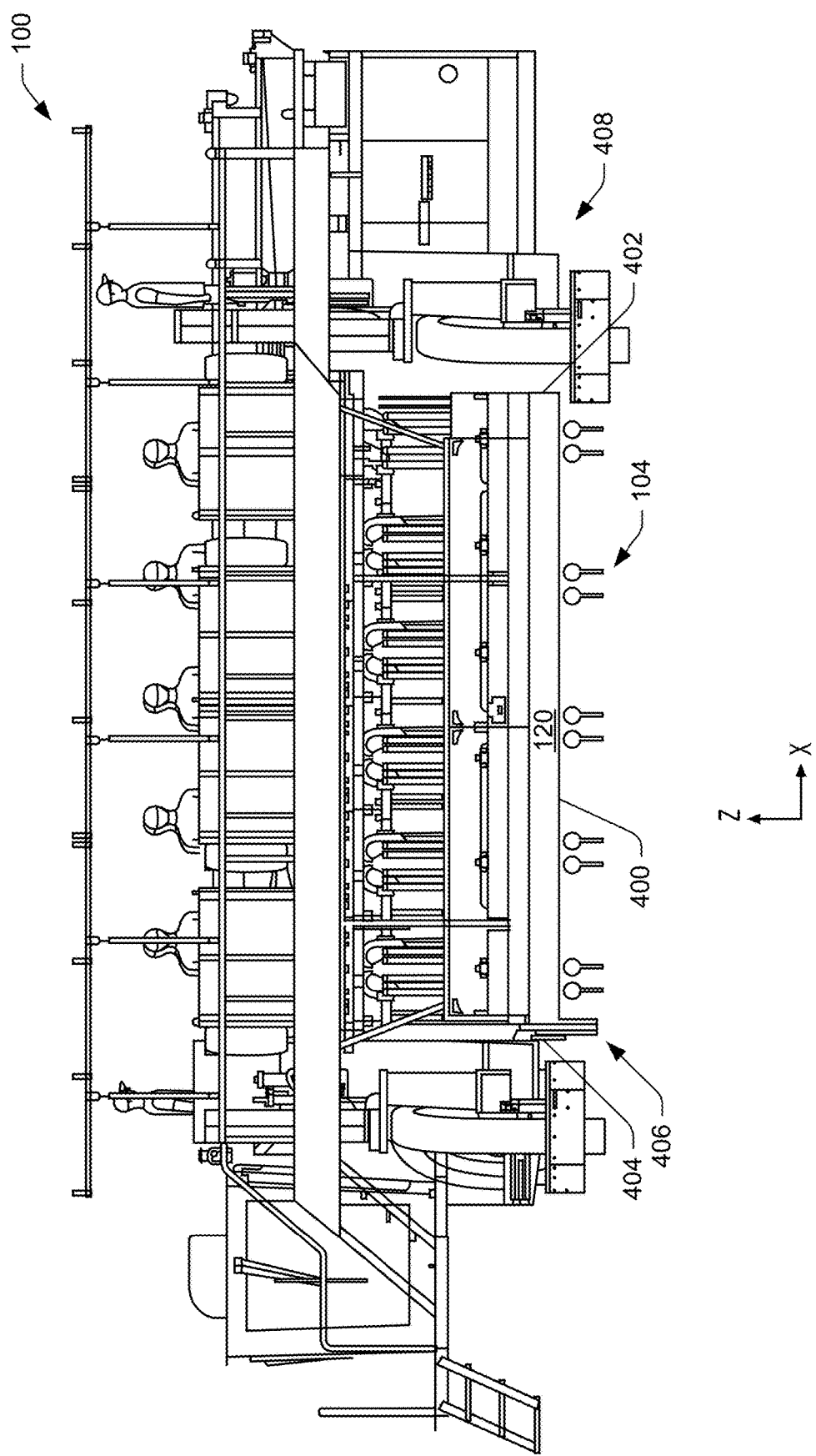
FIG. 4 illustrates a second side view of the harvester of FIG. 1, according to an embodiment of the present disclosure.

FIG. 4 illustrates a side view of the harvester 100, such as the first side 110. The hood 120 is shown being disposed vertically above the broccoli plants 104 (e.g., Z-direction) such that the imaging devices may image the edible crowns 124 for use in determining whether the edible crowns 124 are ready for harvesting. Discussed above in relation to FIG. 3, positioned behind the hood 120 (Y-direction) may be the robotic arms 126 having the end effectors that harvest the edible crowns 124 of the broccoli plants 104. After the end effectors harvest the edible crowns 124, those edible crowns may be transferred to the platform 128 for processing (e.g., packaging) by the personnel.

FIG. 4 illustrates that the hood 120 is disposed vertically above the broccoli plants 104, with a certain distance interposed between a top of the broccoli plants 104 and a bottom 400 of the hood 120. In some instance, the hood 120 may be disposed a predetermined distance above the ground, or above the top of the broccoli plants 104 (or of the edible crowns 124). In some instances, the harvester 100 may optionally include a sensor for determining a distance between the bottom 400 of the hood 120 and the ground (or a distance between the bottom 400 and the top of the edible crowns 124), and correspondingly, causing a height of the hood 120 to be adjusted (Z-direction).

As illustrated, the hood 120 may include a first end 402 and a second end 404 disposed between the wheels 108 on the first side 110. In some instances, the harvester 100 may include support wheel 406 at the second end 404 for supporting a weight of the hood 120 and/or adjusting an elevation of the hood 120 above the ground. Additionally, or alternatively, the harvester 100 may include a support wheel at the first end 402 of the hood 120. As the harvester 100 moves across the field 102, the support wheel 406 may traverse across the ground for adjusting the hood 120 upward and/or downward (Z-direction). For example, when the support wheel 406 experiences an uphill movement, a linkage connected with the hood 120 may push the hood 120 upwards, away from the ground. This may prevent the hood 120 running into or hitting the edible crowns 124. Alternatively, when the support wheel 406 experiences a downhill movement, the linkage connected to the hood 120 may pull the hood 120, closer to the ground and towards the edible crowns 124. Positioning the hood 120 closer to the ground may result in the imaging devices being closer to the broccoli plants 104, which may increase an image quality of the edible crowns 124.

FIG. 4 also illustrates a different arrangement of the broccoli plants 104. As shown, and in some instances, the broccoli plants 104 may be planted in rows of two, which are spaced apart from an adjacent two rows of the broccoli plants 104. In some instances, an imaging device may include a first camera for imaging a first of the two rows of broccoli plants 104, while a second camera of the imaging device may image a second of the two rows of broccoli plants 104. Each of the rows, may include a respective robotic arm (including the end effector and/or cutting mechanism), or the harvester 100 may include a single robotic arm for harvesting the two rows of the broccoli plants 104.

Additionally, FIG. 4 illustrates forks that extend from the frame 106 for supporting and coupling to the individual wheels 108. Motors 408 may be coupled to the axle of the wheel 108 for powering the harvester 100 across the field 102.

Figure 5:
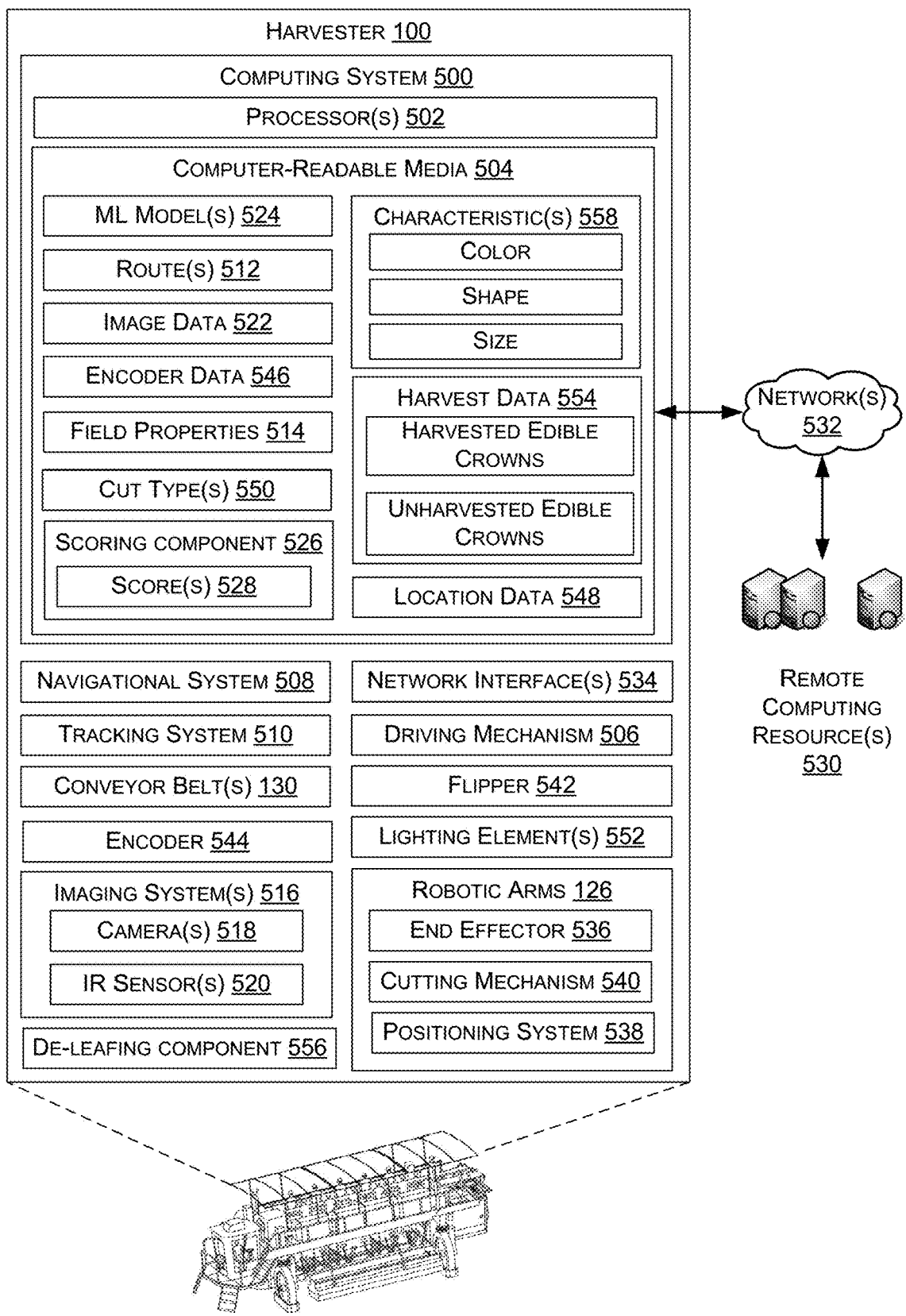
FIG. 5 illustrates example components of the harvester of FIG. 1, according to an embodiment of the present disclosure.

FIG. 5 illustrates selected components of the harvester 100. The components listed and discussed are merely exemplary and it is to be understood that the harvester 100 may include additional and/or different components for carrying out the operations described herein and for harvesting edible crowns.

The harvester 100 may include a computing system 500 that functions to carry out perform the described operations, as well as controlling components of the harvester 100. The computing system 500 is shown including processor(s) 502 and computer-readable media 504. The processor(s) 502 may perform various operations described herein. As shown, the computer-readable media 504 may store or otherwise have access to various information, including instructions that, when executed, cause the processor(s) 502 to perform the operations described herein. The processor(s) 502 also communicatively couple to components of the harvester 100 for receiving data and transmitting instruction, as well as causing data to be stored within the computer-readable media 504.

As discussed above, the harvester 100 may include components for maneuvering about the field 102, such as a driving mechanism 506, a navigational system 508, and/or a tracking system 510. In some instances, the driving mechanism 506 may include components for powering the harvester 100, such as motors and/or engines (combustion or electric), batteries, solar panels, components for driving the harvester 100, such as wheels (e.g., the wheels 108) or continuous tracks, components for distributing and/or transfer the power throughout the harvester 100 (e.g., transfer cases, differentials, gear boxes, electrical boxes/cables/lines), and components for directing the harvester 100, such as steering devices. As discussed above, each of the wheels 108 may be independently powered and/or steered. The driving mechanism 506 may also include the generator 114, which may power the wheels 108 and/or other components of the harvester 100.

The navigational system 508 may include components for navigating the harvester 100 within the field 102. For example, the navigational system 508 may include a global position system (GPS) that is utilized to navigate the harvester 100 along routes or certain paths throughout the field 102. The navigational system 508 may, in some instances, be utilized by the operator of the harvester 100 for steering the harvester 100. In some instances, the navigational system 508 may control or transmit instructions to the driving mechanism 506, or components thereof. The instructions transmitted to the driving mechanism 506 may indicate an amount of power to supply to each wheel, a bearing, heading, or where to direct the harvester 100. In this sense, the navigational system 508 may navigate the harvester 100 throughout the field 102 using the driving mechanism 506. Such processes may also be carried out by the computing system 500 for instructing the driving mechanism 506 as to where to maneuver the harvester 100. Other navigational instruments may additionally, or alternatively, be used for directing the harvester 100 within the field 102.

The tracking system 510, meanwhile, may track a location or position of the harvester 100 within the field 102. For example, as the harvester 100 moves, the tracking system 510 may record or store locations of the harvester 100. These locations may be used to navigate the harvester 100 within the field 102, such as along a predetermined route for harvesting the broccoli plants 104. In some instances, the navigational system 508 may utilize the tracking system 510, or data generated by the tracking system 510 (e.g., the locations, GPS coordinates, etc.) for navigating the harvester 100 within the field 102. For example, based on tracking the harvester 100, the navigational system 508 may steer to direct the harvester 100 to certain positions or points within the field 102 using the driving mechanism 506.

As shown, the computer-readable media 504 may store or otherwise have access to route(s) 512 and field properties 514. In some instances, the route(s) 512 may represent a route or path the harvester 100 is to travel along within the field 102. The route(s) 512 may, in some instances, correspond to or be associated with the rows of the broccoli plants 104. The harvester 100 is configured to travel along the route(s) 512, and as the harvester 100 travel(s) along the route(s) 512, the harvester 100 may function to harvest the broccoli plants 104. In some instances, the harvester 100 may travel along the route(s) 512 without aid from the operator (e.g., via the driving mechanism 506, the navigational system 508, and/or the tracking system 510). In some instances, the route(s) 512 may be predetermined routes based on information known about the field 102 and/or the location of the rows of the broccoli plants 104 within the field 102. In other instances, the route(s) 512 may be determined through onboard sensor(s) of the harvester 100 for steering or otherwise directing the harvester 100. In some instances, the route(s) 512 may be determined such that the harvester 100 may harvest a certain number of rows simultaneously.

In some instances, the route(s) 512 may be determined using the field properties 514. The field properties 514, in some instances, may represent or correspond to a location of the field 102 (amongst other fields), an amount of rows in the field 102, an amount of planted broccoli plants 104 within the field 102, a size of the field 102, an area of the field 102, dimensions of the field 102 (e.g., shape), and so forth. Knowing the field properties 514, or properties of the field 102, may be used to determine the route(s) 512 along which the harvester 100 is to travel to harvest the broccoli plants 104.

The harvester 100 includes imaging system(s) 516 (or devices). The imaging system(s) 516, as introduced above, images or captures image(s) of the edible crowns 124 or the broccoli plants 104. In some instances, the harvester 100 may include a corresponding number of imaging system(s) 516 as the number of rows the harvester 100 is configured to harvest. For example, if the harvester 100 is designed or configured to harvest six rows of broccoli plants 104 simultaneously, the harvester 100 may include six imaging systems 516. Additionally, or alternatively, the imaging system(s) 516 may image edible crowns across multiple rows of broccoli plants 104.

The imaging system(s) 516 may include camera(s) 518 and/or infrared (IR) sensor(s) 520. In some instances, the camera(s) 518 may include red-green-blue (RGB) cameras for capturing colored images of the edible crowns. Additionally, or alternatively, the camera(s) 518 may be high dynamic range (HDR) cameras, one or more of light-sensitive cameras, range sensors, or other types of imagers. In some instances, images captured by the camera(s) 518 may be utilized for determining color, size, shape, and/or other characteristic(s) of the edible crowns that are useful in determining whether the edible crowns are ready for harvesting. The IR sensor(s) 520 may capture depth information, which in some instances, may be used to additionally, or alternatively, determine whether the edible crowns are ready for harvesting. In some instances, the depth information, depth images, or a depth map generated by the IR sensor(s) 520 may be utilized to determine color, size, shape, and/or other characteristics of the edible crowns that are useful in determining whether the edible crowns are ready for harvesting. In some instances, this depth information may be utilized in combination with the image(s) captured by the camera(s) 518. As such, the computing system 500 may use the camera(s) 518 and/or the IR sensor(s) 520 for use in determining whether the edible crowns are ready for harvesting.

In some instances, the imaging system(s) 516 may include multiple camera(s) and/or multiple IR sensors for imaging the edible crowns (or a single edible crown) from multiple angles, orientations, and/or positions. These image(s) may then be analyzed to determine whether the edible crowns are ready for harvesting. In some instances, however, the imaging system(s) 516 may capture a single image of the edible crowns. Regardless of the number of image(s), the number of camera(s), and/or the number of IR sensor(s) 520 utilized to image the edible crowns, the image(s) are then processed by components of the computing system 500 for determining whether the edible crowns are ready for harvesting. In some instances, the imaging system(s) 516 may capture videos, and the computing system 500 may analyze frames of the videos to determine whether the edible crowns are ready for harvesting.

The computer-readable media 504 is shown storing image data 522, which may correspond to the image(s) captured by the camera(s) 518 and/or the IR sensor(s) 520. Once the imaging system(s) 516 image the edible crowns, this information (i.e., the image(s) and/or the depth information) may be stored in the computer-readable media 504 for use in determining whether the edible crowns are ready for harvesting. The computing system 500 may therein analyze the image data 522 of a particular edible crown to determine whether the particular edible crown is ready for harvesting. As such, the image data 522 may be stored in association with particular edible crowns such that the computing system 500 may track and record the edible crowns along the route(s) 512, as well as which image data 522 corresponds to which edible crown along the route(s) 512 (e.g., to be able to distinguish image data of one edible crown from another).

In some instances, the computing system 500 may utilize one or more machine-learning (ML) model(s) 524 for determining whether to harvest the edible crowns 124. The ML model(s) 524 may analyze the image data 522, or other information, for use in determining whether the edible crowns are ready for harvesting. In some instances, the computing system 500 may include a scoring component 526 that determines or generates scores 528 for the edible crowns that are imaged by the harvester 100. In some instances, individual scores 528 may be determined by accessing data associated with an individual edible crown, such as the image data 522, providing the data as input to the ML model(s) 524, and generating, as output from the ML model(s) 524, the score 528 that is associated with the individual edible crown.

The score 528 may relate to a probability or likelihood that an edible crown is ready for harvesting or not ready for harvesting. In other words, the scores 528 determined by the scoring component 526 (e.g., output by the ML model(s) 524) may be machine-learned scores. Machine learning generally involves processing a set of examples (called "training data") in order to train a machine learning model(s). A machine learning model(s), once trained, is a learned mechanism that can receive new data as input and estimate or predict a result as output. For example, a trained machine learning model may comprise a classifier that is tasked with classifying unknown input (e.g., an unknown image) as one of multiple class labels (e.g., labeling the image as a cat or a dog). In some cases, a trained machine learning model is configured to implement a multi-label classification task (e.g., labeling images as "cat," "dog," "duck," "penguin," and so on). Additionally, or alternatively, a trained machine learning model may be trained to infer a probability, or a set of probabilities, for a classification task based on unknown data received as input.

In the context of the present disclosure, the unknown input may be the image data 522 that is associated with a particular edible crown, and the ML model(s) 524 may be tasked with outputting the score 528 that indicates, or otherwise relates to, a probability of the edible crown being ready for harvesting (or not ready for harvesting). For instance, the score 528 may relate to a probability of an edible crown being ready for harvesting or not ready for harvesting. The score 528 that is output by the ML model(s) 524 may relate to either of these probabilities in order to guide the harvesting processes. If the score 528 that is output by the ML model(s) 524 relates to a likelihood that the edible crown is ready for harvesting, this may indicate that the edible crown is ready for harvesting.

The training data that is used to train ML model(s) 524 may include various types of data. In general, training data for machine learning may include two components, features and labels. However, in some instances, the training data used to train the ML model(s) 524 may be unlabeled. Accordingly, the ML model(s) 524 may be trainable using any suitable learning technique, such as supervised learning, unsupervised learning, semi-supervised learning, reinforcement learning, and so on. The features included in the training data can be represented by a set of features, such as in the form of an n-dimensional feature vector of quantifiable information about an attribute of the training data. The following is a list of example features that can be included in the training data for training the ML model(s) 524 described herein. However, it is to be appreciated that the following list of features is non-exhaustive, and features used in training may include additional features not described herein, and, in some cases, some, but not all, of the features listed herein. Example features included in the training data may include, without limitation, a width of the edible crown, a width of the broccoli plant, a length of the edible crown, a length of the broccoli plant, a height of the edible crown, a height of the broccoli plant, a largest-cross-sectional dimension of the edible crown, a largest cross-sectional dimension of the broccoli plant, a color of the edible crown (including hue, shade, tint, etc.), a shape of the edible crown, an amount of leaves on the broccoli plant, a row or particular area within the field 102 at which the edible crown is located, an amount of buds of the edible crown, a density of the edible crown, a volume of the edible crown, a strain or species of the broccoli plant, a number of previously harvested edible crowns at the specific or regional location as the edible crown, a frequency of other edible crowns harvested around the edible crown (in the same row or additional rows), and so forth. In some instances, the features included within the training data may be associated with harvested edible crowns (or plants) and/or unharvested edible crowns (or plants).

In some instances, as part of the training process, weights may be applied to a set of features included in the training data, as derived from the historical data. In some instances, the weights that are set during the training process may apply to parameters that are internal to the ML model(s) 524 (e.g., weights for neurons in a hidden-layer of a neural network). These internal parameters of the ML model(s) 524 may or may not map one-to-one with individual input features of the set of features. The weights may indicate the influence that any given feature, parameter, or characteristic has on the score 528 that is output by the scoring component 526 using the ML model(s) 524.

The ML model(s) 524 may represent a single model or an ensemble of base-level machine learning models, and may be implemented as any type of machine learning model. For example, suitable machine learning models for use with the techniques and systems described herein include, without limitation, neural networks, tree-based models, support vector machines (SVMs), kernel methods, random forests, splines (e.g., multivariate adaptive regression splines), hidden Markov model (HMMs), Kalman filters (or enhanced Kalman filters), Bayesian networks (or Bayesian belief networks), expectation maximization, genetic algorithms, linear regression algorithms, nonlinear regression algorithms, logistic regression-based classification models, or an ensemble thereof. An "ensemble" can comprise a collection of machine learning models whose outputs (predictions) are combined, such as by using weighted averaging or voting. The individual machine learning models of an ensemble can differ in their expertise, and the ensemble can operate as a committee of individual machine learning models that is collectively "smarter" than any individual machine learning model of the ensemble.

The ML model(s) 524 may learn to identify complex relationships between characteristic(s) of the edible crowns. For example, the ML model(s) 524 may learn to associate certain characteristics of the edible crown with one another to indicate whether the edible crown is ready for harvesting. The ML model(s) 524 herein allow for generating the scores 528 that more accurately predict whether edible crowns are ready for harvesting, leading to increased yields and fewer instances of harvesting edible crowns prior to maturity. In some instances, the ML model(s) 524 may learn to predict which edible crowns are likely ready for harvesting, and which edible crowns are unlikely ready for harvesting by attributing corresponding scores 528 to the individual edible crowns. In this manner, edible crowns with low scores (e.g., below threshold) may not be ready for harvesting, while edible crowns with high scores (e.g., above threshold) may be ready for harvesting. Although the use of a threshold is described as one example way of providing labeling (i.e., ready for harvesting or not ready for harvesting), other techniques are contemplated, such as clustering algorithms, or other statistical approaches that use the trust scores for use in determining whether edible crowns are ready for harvesting.

The ML model(s) 524 is/are retrainable with new data in order to adapt the ML model(s) 524 to understand harvestable edible crowns, as the characteristic(s) of the edible crowns 124 change, or new correlations become available. In some instances, the ML model(s) 524 may be retrained using image data from harvested edible crowns and/or unharvested edible crowns. That is, the ML model(s) may be trained from characteristic(s) of edible crowns that were ready for harvesting and/or edible crowns that were not ready for harvesting, so as to be able to determine which edible crowns are ready for harvesting and/or which edible crowns are not ready for harvesting.

In some instances, the harvester 100 may communicatively couple to remote computing resource(s) 530. In some instances, the remote computing resource(s) 530 may train the ML model(s) 524 and may then transmit the ML model(s) 524 to the harvester 100. In some instances, the remote computing resource(s) 530 may train the ML model(s) 524 and/or may store data utilized to train the ML model(s) 524. For example, over time, one can appreciate that a large collection of historical data tied to harvestable edible crowns may be available to the remote computing resource(s) 530. The remote computing resource(s) 530 may train the ML model(s) 524 using a portion of the historical data as training data. For instance, a portion of the historical data may be labeled to indicate characteristic(s) of edible crowns that are ready for harvesting, or which were harvested (and/or not harvested) in the past. A ML model(s) trained on this data is able to predict harvestable edible crowns by outputting machine-learned scores (e.g., the scores 528) that represent a confidence and/or trust that the edible crowns imaged by the imaging system(s) 516 are ready for harvesting. As such, these machine-learned scores are usable by the computing system 500 for determining whether the imaged edible crown is ready for harvesting.

After the ML model(s) 524 have been trained, in such instances, the remote computing resource(s) 530 may transmit the ML model(s) 524 to the harvester 100 for use in determining harvestable edible crowns. This may allow the harvester 100 to determine whether the edible crowns are ready for harvesting in real-time. However, in some instances, the remote computing resource(s) 530 may determine the harvestable edible crowns, using information received from the harvester 100 (e.g., the image data 522), and then transmit indications back to the harvester 100 as to which edible crowns to harvest.

The harvester 100 may communicate with the remote computing resource(s) 530 over one or more network(s) 532 and using one or more network interface(s) 534. The network(s) 532 may represent and/or include, without limitation, the Internet, other types of data and/or voice networks, a wireless infrastructure (e.g., radio frequencies (RF), cellular, satellite, etc.), and/or other connection technologies. The harvester 100 may, in some instances be part of a network-accessible computing platform that is maintained and accessible via the network(s) 532. Network-accessible computing platforms such as this may be referred to using terms such as "on-demand computing", "software as a service (SaaS)", "platform computing", "network-accessible platform", "cloud services", "data centers", and so forth.

As shown, the computer-readable media 504 may further store or have access to characteristic(s) 558. These characteristic(s) 558 may, in some instances, be determined via the ML model(s) 524 and represent characteristics of the edible crowns that are imaged by the imaging system(s) 516. For example, upon analyzing the image data 522 (e.g., via the ML model(s) 524), the characteristic(s) 558 of the broccoli plants 104 (or of the edible crowns 124) may be determined. By way of example, and as shown, these characteristic(s) 558 may include a color of the edible crown 124, a shape of the edible crown 124, and/or a size of the edible crown 124. However, it is to be understood that the edible crowns 124 and/or the broccoli plants 104 may include other characteristics that are used for determining whether the edible crowns 124 are ready for harvesting (or not ready for harvesting). Thus, after analyzing the image data 522, the characteristic(s) 558 may be determined, which in turn, may be used for determining whether to harvest the edible crowns 124. These characteristic(s) 558 may also be used to train and/or retain the ML model(s) 524.

In some instances, certain characteristics may be indicative of whether the edible crown 124 is ready for harvesting, such as color, shape, and/or size. After analyzing the image data 522 to determine these characteristic(s) 558, the characteristic(s) 558 may be compared to reference characteristics, such as a reference size, a reference color, and/or a reference shape. These references may be determined from training the ML model(s) 524 based on the historical data, and may be references for comparison to the particular edible crown 124 being imaged (e.g., the characteristic(s) 558). The ML model(s) 524 may perform the comparison. The references may be indicative of edible crowns 124 that are ready for harvesting and by comparing the characteristic(s) 558 to the reference characteristics, the computing system 500 may determine whether the edible crowns 124 are ready for harvesting.

In some instances, the scoring component 526 (using the ML model(s) 524) may determine the characteristic(s) 558 and/or analyze the characteristic(s) 558 for use in generating the score(s) 528 and/or determining whether the edible crowns 124 are ready for harvesting. For example, the scoring component 526 may generate the score(s) 528 and compare the score(s) 528 to a threshold or predetermined level to determine whether the score 528 satisfies the threshold. If so, the edible crown 124 may be deemed ready for harvesting.

Upon determining that the edible crowns 124 are ready for harvesting, the robotic arms 126 may navigate to and position above the edible crowns 124 selected or otherwise flagged for harvesting. The harvester 100 may include a corresponding number of the robotic arms 126 as a number of rows of the broccoli plants 104 that the harvester 100 is configured to harvest. In other instances, the harvester 100 may include robotic arms 126 that harvest edible crowns 124 across multiple rows. The robotic arms 126 may be controlled, or instructed, by the computing system 500 or components thereof (e.g., the processor(s) 502). For example, after determining that the edible crown 124 is ready for harvesting, the processor(s) 502 may instruct the robotic arm 126 to harvest the edible crown 124. The harvester 100, or the computing system 500, may be configured to instruct, simultaneously, the robotic arms 126 to harvesting corresponding edible crowns 124 across rows of broccoli plants 104.

As part of instructing the robotic arms 126, the computing system 500 may also generate data and/or determine a location of the edible crowns 124 relative to the robotic arms 126 (e.g., a position of the robotic arms 126). In some instances, this location may represent coordinate positions in coordinate space (X, Y, Z) for which the robotic arm 126 is to navigate to in order to harvest the edible crown 124. In some instances, the computing system 500 may determine the location of the edible crowns 124 to be harvested based on analyzing the image data 522. For example, as part of analyzing the image data 522, and knowing a location of the imaging system(s) 516 and the robotic arms 126 on the harvester 100, the computing system 500 may determine a location of the edible crown 124 within the field 102.

In some instances, the location of the edible crown 124 may be a central position (or point) of the edible crown 124, or a central position of the broccoli plant 104. In some instances, the central position of the edible crown 124 may be centered over the edible crown 124 (e.g., X and Y positions). The central position may also define a midpoint between a top of the edible crown 124 and a point at which the stalk 122 of the broccoli plant 104 is to be cut (e.g., just below a base of the edible crown 124). Interposed between these two points, may be an additional coordinate of the edible crown 124, or the central point (e.g., Z-position). This point, in the vertical direction, allows the robotic arm 126 to descend unto or onto the edible crown 124 by a certain distance for grasping the edible crown 124. For example, as discussed above, the robotic arms 126 include end effectors 536 that function to grip or grasp the edible crowns 124 that are ready for harvesting.

In some instances, the robotic arms 126 may include or be coupled to a positioning system 538 for positioning the end effector 536 relative to the edible crown 124. In some instances, the positioning system 538 may represent track(s), arms, linkages, members, or rail(s) upon which the robotic arms 126 may move to position the end effector 536. For example, the robotic arm 126 may slide along the tracks and/or rails for positioning the end effector 536. The positioning system 538 may translate in one or more directions for maneuvering the end effector 536 relative to the edible crown 124. Additionally, or alternatively, the robotic arms 126 and/or the positioning system 538 may include actuators, turntables, telescoping assemblies, lifts, and so forth for navigating the end effector 536 to the edible crown 124. In such instances, the computing system 500 may control actuators of the robotic arms 126 and/or of the positioning system 538 for moving the end effector 536.

The robotic arms 126 may also include a cutting mechanism 540 for harvesting the edible crown 124, or for separating the edible crown 124 from the rest of the broccoli plant 104 (e.g., the stalk 122). The cutting mechanism 540, in some instances, may be disposed on a portion of the end effector 536, and may include one or more stationary blades and/or one or more actuatable blades actuatable by a motor of actuator of the cutting mechanism 540 (and/or the robotic arm 126 or the end effector 536).

After the edible crown 124 is harvested, that is, separated from the stalk 122, the robotic arm 126 may transfer the edible crown 124 to one or more collection sites. In some instances, the positioning system 538 may function to maneuver the robotic arm 126 to the collection sites.

In some instances, after being harvested, the robotic arm 126 may transfer the edible crown 124 to a flipper 542, which may transfer the edible crown 124 to other portions of the harvester 100 for further processing. For example, the flipper 542 may include a basket, cradle, or holder for receiving the edible crown 124. The flipper 542 may then actuate to "flip" the edible crown 124 onto the conveyor belt(s) 130. Upon being transferred to the conveyor belt(s) 130, the edible crown 124 may be carried to the platform 128 of the harvester 100 for further processing.

In some instances, the harvester 100 may include an encoder 544 for tracking or determining a location of the harvester 100 within the field 102, or along the route 512. In some instances, the encoder 544 may be positioned adjected to a hub of one or more of the wheels 108 and may track, or record, a rotational movement of the wheel 108. This rotational movement may be stored as encoder data 546 within the computer-readable media 504. For example, knowing the rotational movement or distance traveled by the wheel 108, may assist in knowing the location of the harvester 100 within the field 102. This location may be used for instructing the navigational system 508 to travel to a particular point within the field 102, and/or may be used for determining the position coordinates of the edible crowns 124 for harvesting. For example, knowing the location of the edible crown 124 relative to the robotic arm 126 (or the end effector 536) may not account for a position of the harvester 100 within the field 102. That is, in some instances, the position coordinates of the edible crown 124 to be harvested may be determined using both the image data 522 (e.g., to determine a position of the edible crown 124), as well as location data 548 of the harvester 100 (e.g., to determine a position of the harvester 100). In some instances, this location data 548 may be determined via the encoder 544 (from the encoder data 546) and/or the navigational system 508 and/or tracking system 510 (e.g., GPS, triangulation, etc.).

The encoder 544 may also be used for tracking or determining a location of the edible crowns 124 within the field 102. For example, the encoder 544 may track rotational movement of at least one wheel 108 of the harvester 100 to determine distance traveled by the harvester 100 in a forward direction of travel, relative to a reference point. In some instances, the encoder data 546 generated by the encoder 544 may be used to determine position coordinates of the edible crowns 124 that are designated for harvesting. Additionally, or alternatively, the navigational system 508 may include a GPS component and the position of the harvester 100 within the field 102 may be determined using the GPS component. In such instances, the location (the location data 548) may be determined via the GPS component.

In some instances, the harvester 100 may be configured to perform different cut type(s) 550 based on characteristic(s) of the edible crowns 124 and/or the broccoli plants 104. These characteristic(s) (e.g., the characteristic(s) 558) may indicate how far down the stalk the cutting mechanism 540 is to cut and/or whether the end effector 536 (or other portions of the robotic arms 126) are to trim/strip leaves from the stalk 122. For example, larger sized broccoli plants 104 may include leaves that extend upwards and around/into the edible crown 124. These leaves are often undesirable when harvesting as they may cause an increase in processing and/or cleaning times. In some instances, based on analyzing the image data 522, the computing system 500 may determine a size of the edible crown 124 (or the broccoli plant 104) for determining which type of cut to perform. For example, if the edible crown 124 is ready for harvesting, but a greatest cross-sectional dimension is less than a threshold (e.g., 4.75 inches), the computing system 500 may determine to perform a first type of cut, among the cut type(s) 550. The computing system 500 may then instruct the robotic arm 126, or the cutting mechanism 540 to perform the first type of cut. Alternatively, if the greatest cross-sectional dimension is greater than the threshold, the computing system 500 may determine to perform a second type of cut among the cut type(s) 550. The computing system 500 may then instruct the robotic arm 126, or the cutting mechanism 540 to perform the second type of cut. In some instances, the second type of cut may involve stripping leaves around the edible crown 124 using the end effector 536. Alternatively, certain consumers may desire longer stalks 122 attached to the edible crown 124. In such instances, the cutting mechanism 540 may be configured to cut varying lengths of stalk 122 below the edible crown 124.

The harvester 100 may also include lighting element(s) 552. In some instances, the lighting element(s) 552 may illuminate the edible crowns 124 underneath the hood 120 for obtaining quality image(s) of the edible crowns 124. The lighting element(s) 552 may also illuminate the edible crowns 124 in instances where the harvester 100 operates at night or low lighting conditions (e.g., overcast). The lighting element(s) 552, in some instances, may comprise white light LEDs and/or colored LEDS. The lighting element(s) 552 may also include organic light emitting diodes (OLEDs), and/or other lights that adequately illuminate the edible crowns 124.

The computer-readable media 504 may further store harvest data 554, which may include harvested edible crowns and unharvested edible crowns. The harvested edible crowns may correspond to those edible crowns 124 that were harvested, while the unharvested edible crowns may correspond to those edible crowns 124 that were not harvested and which remain planted in the field 102 (e.g., unharvested edible crowns 206). In some instances, the harvest data 554 may indicate a location of the harvested edible crowns as well as a location of the unharvested edible crowns. Such locations may be used for analyzing field properties and/or characteristics, for use in future instances when harvesting. This information may also be used to train the ML model(s) 524. Additionally, the information may be used to determine which portions of the field 102 have a high yield, which portions have a low yield, which portions of the field 102 were harvested, and/or which portions of the field 102 were not harvested. These trends may be analyzing for adjusting harvesting schedules and/or other harvesting processes (e.g., watering, fertilizing, etc.). Additionally, noted above, the harvest data 554 may identify characteristics of the harvested edible crowns and unharvested edible crowns. This information may be used to retain the ML model(s) 524 and/or may be used to determine when the unharvested edible crown will be ready for harvesting. Therein, at future instances, the harvester 100 or personnel may selectively broccoli harvest the edible crowns at they become ready.

The harvester 100 may also include a de-leafing component 556 that removes leaves from the broccoli plant 104. In some instances, the de-leafing component may be located in front of the imaging system(s) 516, relative to the direction of travel of the harvester 100, to remove the leaves and isolate the edible crown 124 for obtaining clear image(s). In some instances, the de-leafing component 556 may be a separate component, machine, or device than the harvester 100. The imaging system(s) 516 may image the edible crown 124 for use by the computing system 500 to determine whether the edible crown 124 is ready for harvesting. In some instances, the de-leafing component 556 may include rotating blade(s) that may resemble rotary knives or swinging flail knives. In some instances, the rotating blades are spaced apart by a distance such that the rotating blades pass along a row of the broccoli plants 104 to cut away the outer leaves of the broccoli plant 104 and leave the broccoli plants 104 unharmed and revealing the edible crown 124.

As used herein, the computer-readable media 504 may be implemented as computer-readable storage media ("CRSM"), which may be any available physical media accessible by the processor(s) 502 to execute instructions stored on memory. The memory (or non-transitory computer-readable media) may include volatile and nonvolatile memory, removable and non-removable media implemented in any method or technology for storage of information, such as computer-readable instructions, data structures, program modules, or other data. Such memory includes, but is not limited to, random access memory ("RAM"), read-only memory ("ROM"), erasable programmable read-only memory ("EEPROM"), flash memory or other memory technology, CD-ROM, digital versatile disks (DVD) or other optical storage, magnetic cassettes, magnetic tape, magnetic disk storage or other magnetic storage devices, RAID storage systems, or any other medium which can be used to store the desired information and which can be accessed by a computing device and the processor(s) 502.

Figure 6A:
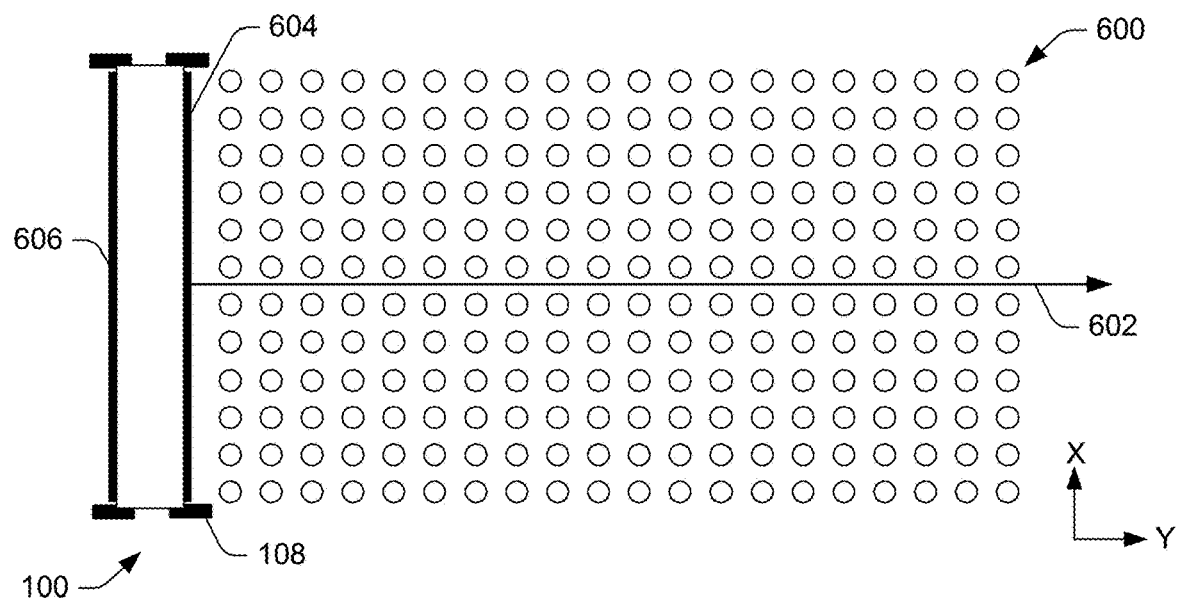
FIG. 6A illustrates a diagram showing an example route of the harvester of FIG. 1 within a field for harvesting edible crowns, according to an embodiment of the present disclosure.
Figure 6B:
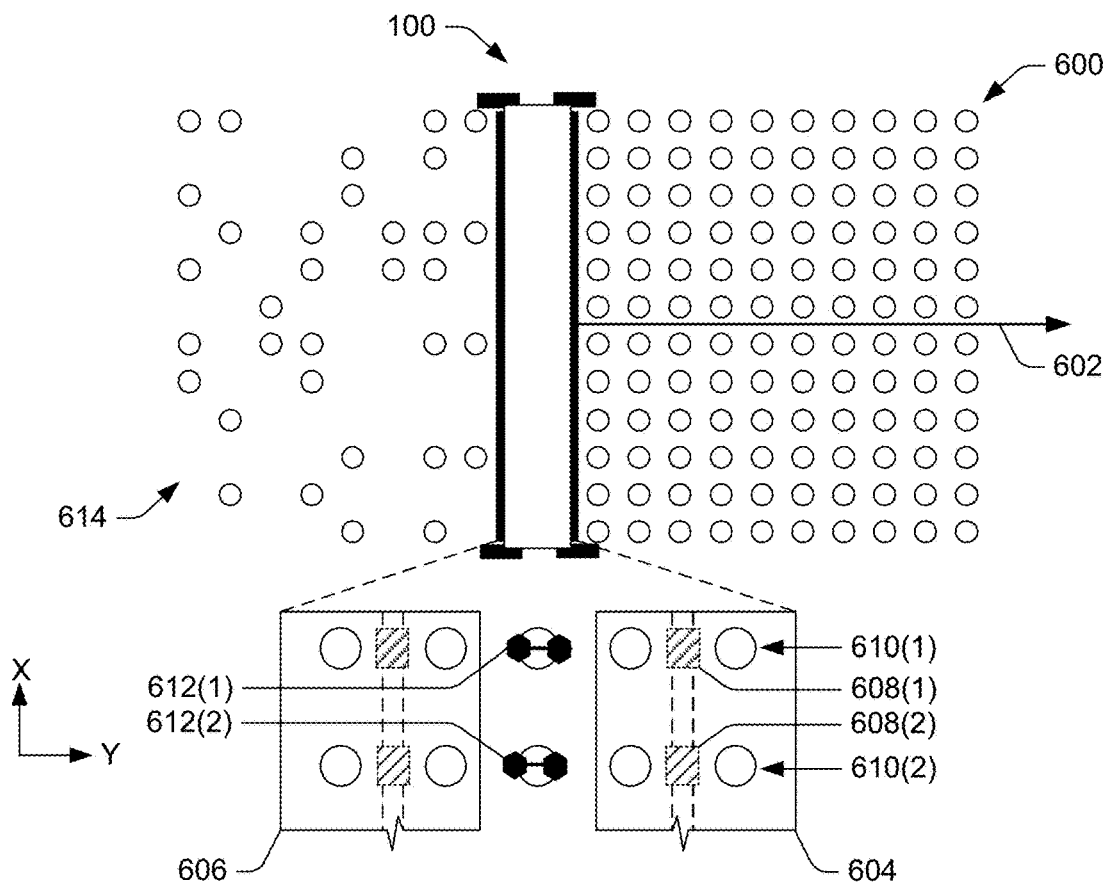
FIG. 6B illustrates the harvester moving along the route of FIG. 6A for harvesting edible crowns, according to an embodiment of the present disclosure. The harvester may image the edible crowns, determine whether the edible crowns are ready for harvesting, and if so, may harvest the edible crowns.

FIGS. 6A and 6B illustrate the harvester 100 traveling within a field 600 to harvest edible crowns. As shown, the field 600 may include twelve rows of broccoli plants, and the harvester 100 may be configured to image and harvest edible crowns across the twelve rows of broccoli plants. The wheels 108 of the harvester 100 are shown spanning across the twelve rows of broccoli plants.

The harvester 100 travels along a route 602 within the field 600. The harvester 100 may, in some instances, include a first hood 604 for imaging edible crowns along the route, and as the harvester 100 travels in a direction of travel (Y-direction, and as shown by the arrow). The first hood 604 may include similar components as the hood 120 (e.g., the imaging system(s) 516, etc.). Additionally, in some instances, the harvester 100 may include a second hood 606, which may include similar components as the additional hood 200.

As the harvester 100 travels along the route 602, the harvester 100 images the edible crowns and determines whether to harvest individual edible crowns. For example, as shown in FIG. 6B, the harvester 100 includes a first imaging system 608(1) for imaging edible crowns within a first row 610(1) and a second imaging system 608(2) for imaging edible crowns within a second row 610(2). Once the edible crowns pass under (or come within a field of view of the first imaging system 608(1) and the second imaging system 608(2)) the first hood 604, the first imaging system 608(1) and the second imaging system 608(2) may image the edible crowns of the first row 610(1) and the second row 610(2), respectively.

The image(s) captured by the first imaging system 608(1) and the second imaging system 608(2) may be analyzed by the computing system 500 for determining whether the edible crowns are ready for harvesting. If so, robotic arms and end effectors may harvest the edible crowns. For example, as shown in FIG. 6B, after being imaged by the first imaging system 608(1) and the second imaging system 608(2), the harvester 100 may include a first robotic arm 612(1) and a second robotic arm 612(2) for harvesting the edible crowns. The first robotic arm 612(1) and/or the second robotic arm 612(2) may be similar to and/or include similar components as the robotic arm 126. In some instances, the first robotic arm 612(1) and the second robotic arm 612(2) may be disposed between the first hood 604 and the second hood 606. Although the first robotic arm 612(1) and the second robotic arm 612(2) are shown including end effectors (e.g., the end effectors 536) having two fingers for grasping the edible crown, the first robotic arm 612(1) and the second robotic arm 612(2) (or the end effectors) may include more than or less than four fingers. The fingers are sized and configured to descend over a top of the edible crown and converge around the edible crown for harvesting.

In some instances, the first robotic arm 612(1) may be associated with the first row 610(1) and for harvesting edible crowns within the first row 610(1), after being imaged by the first imaging system 608(1). The second robotic arm 612(2) may be associated with the second row 610(2) and for harvesting edible crowns within the second row 610(2), after being imaged by the second imaging system 608(2). The first robotic arm 612(1) and the second robotic arm 612(2) may include respective end effectors, cutting mechanisms, actuators, and so forth, for harvesting the edible crowns.

As shown in FIG. 6B, some of the edible crowns within the field 600 may not be ready for harvesting. Consequentially, after being imaged (e.g., by the imaging systems of the harvester 100) these edible crowns may not be harvested by the harvester 100. For example, FIG. 6B illustrates that on a trailing side of the harvester 100, broccoli plants 614 may remain planted for further growing. These broccoli plants 614 may then be harvested at later instances when ripe.

Accordingly, FIGS. 6A and 6B illustrate that as the harvester 100 travels throughout the field 600, the computing system 500 may function to determine which edible crowns to harvest and which edible crowns are to remain planted.

Figure 7:
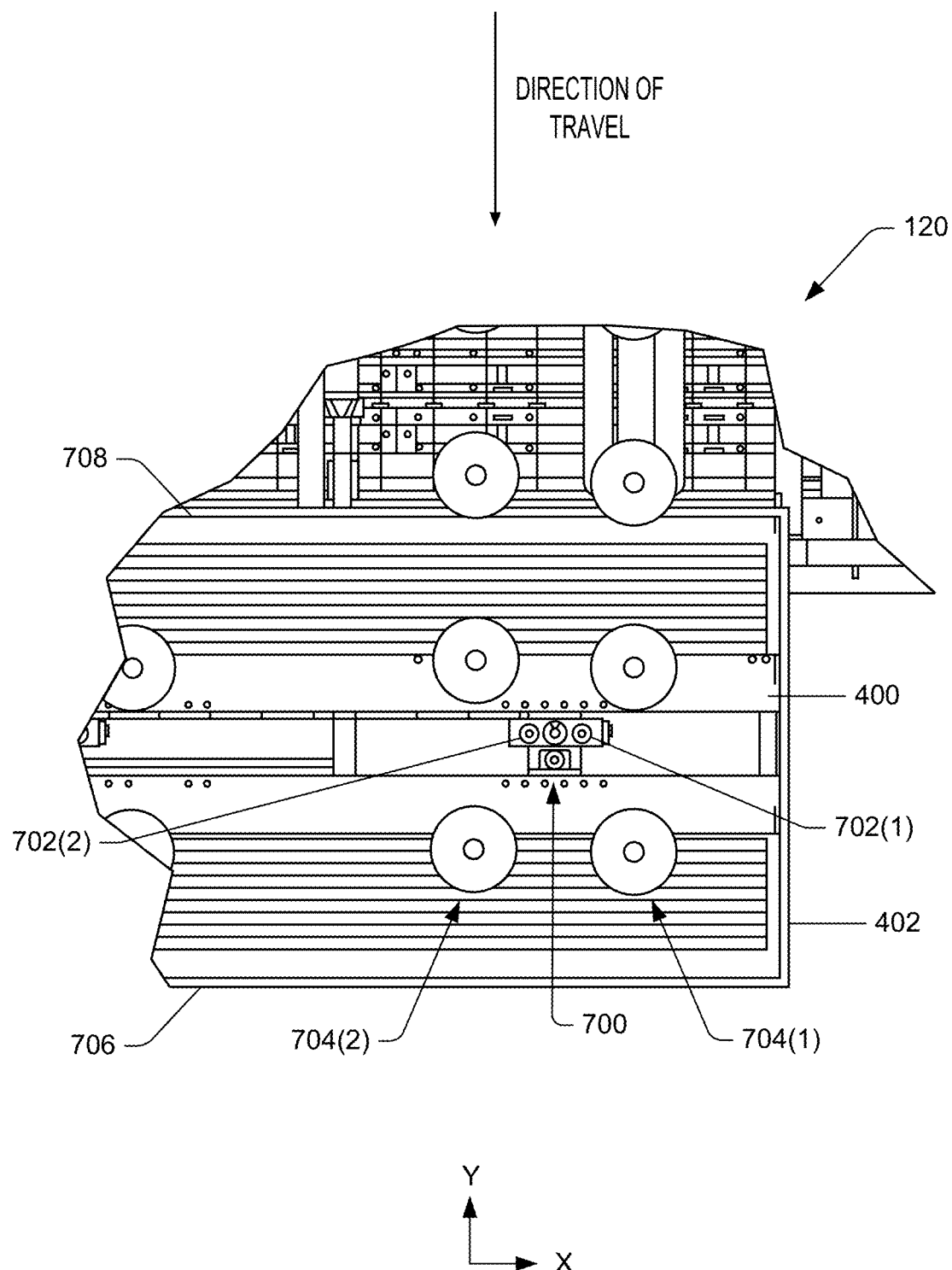
FIG. 7 illustrates an example imaging system of the harvester of FIG. 1 for use in determining whether the edible crowns are ready for harvesting, according to an embodiment of the present disclosure.

FIG. 7 illustrates the bottom 400 of the hood 120, showing an imaging system 700 for capturing images of one or more edible crowns within one or more rows of the broccoli plants 104. The imaging system 700 may represent, be similar to, and/or include similar components as the imaging system 516.

In some instances, and as shown in FIG. 7, two rows of broccoli plants may be planted in close proximity to one another, spaced apart from other row of broccoli plants (X-direction). In some instances, the imaging system 700 may include a first camera/IR sensor 702(1) for capturing images of a first row 704(1) of the broccoli plants and a second camera/IR sensor 702(2) for capturing images of a second row of the broccoli plants 104. The first camera/IR sensor 702(1) may image first edible crowns (or the broccoli plants) within the first row 704(1), while the second camera/IR sensor 702(2) may image second edible crowns within the second row 704(2). In some instances, the first camera/IR sensor 702(1) may be oriented (e.g., angled, tilted, etc.) for capturing images of the broccoli plants within the first row 704(1) and the second camera/IR sensor 702(2) may be oriented (e.g., angled, tilted, etc.) for capturing images of the broccoli plants within the second row 704(2). In some instances, the first camera/IR sensor 702(1) and/or the first camera/IR sensor 702(2) may include an RGB camera and/or an IR sensor.

The imaging system 700 may be located in front of, relative to the direction of travel (Y-direction), the robotic arms 126 that harvest the edible crowns. The hood 120 may include a leading or a front edge 706 and a trailing or a back edge 708. Additionally, discussed above in relation to FIG. 4, the hood 120 may include the first end 402 and the second end 404 (not shown), located opposite the first end 402. In some instances, the imaging system 700 may be centered between the front edge 706 and the back edge 708.

The first camera/IR sensor 702(1) and/or the second camera/IR sensor 702(2) may capture images of one or more edible crowns, within the first row 704(1) and the second row 704(2), respectively, for use determining whether the one or more edible crowns are ready for harvesting. Additionally, or alternatively, in some instances, the imaging system 700 may take multiple images using the first camera/IR sensor 702(1), the second camera/IR sensor 702(2), and/or one or more additional camera(s) and may combine the images (e.g., stitching) for analyzing the edible crowns. In such instances, image(s) from multiple camera(s) may be used for determining whether to harvest a particular edible crown. Additionally, or alternatively, in some instances, the first camera/IR sensor 702(1) and the second camera/IR sensor 702(2) may capture image(s) of a single edible crown within the first row 704(1) and the second row 704(2), respectively for determining whether the edible crowns 124 are ready for harvesting. For example, as the broccoli plants pass underneath the hood 120 and come within a field of view of the imaging system 700, image(s) of the broccoli plants 104 may be captured.

In some instances, the imaging system 700 may image the broccoli plants at a predetermined offset from the front edge 706. For example, the imaging system 700 may wait to image the broccoli plants 104 until the edible crowns 124 are directly underneath (X and Y-directions) the first camera/IR sensor 702(1) and the second camera/IR sensor 702(2), respectively, or are aligned with the first camera/IR sensor 702(1) and the second camera/IR sensor 702(2) (Y-direction). Alternatively, in some instances, the first camera/IR sensor 702(1) and the second camera/IR sensor 702(2) may image the broccoli plants at a predetermined offset from the first camera/IR sensor 702(1) and the second camera/IR sensor 702(2), respectively.

In some instances, the field of view of the imaging system 700 may be adjusted, and accordingly, a point or position at which the first camera/IR sensor 702(1) and/or the second camera/IR sensor 702(2) images the broccoli plants may be adjusted. The adjustment may account for lighting conditions, environmental conditions, and/or characteristics of the broccoli plants within the rows. For example, waiting until the broccoli plants 104 are completely underneath the hood 120 may reduce an impact on external weather (e.g., sun, rain, wind) affecting the image(s) (or quality of the image(s)) captured. Furthermore, spacing in between the broccoli plants 104 within the same row may be different, and the first camera/IR sensor 702(1) and/or the second camera/IR sensor 702(2) may have to be adjusted to accommodate image capturing of the broccoli plants 104.

To account for the adjustments of image capturing, the imaging system 700 may be coupled to actuators or motors that adjust the field of views. In some instances, the imaging system 700 may adjust along multiple axes (X, Y, and Z) and/or in multiple degrees of freedom (e.g., pan, tilt, yaw, etc.). In some instances, each of the first camera/IR sensor 702(1) and the second camera/IR sensor 702(2) may be independently actuatable for controlling or adjusting the field of view of each of the first camera/IR sensor 702(1) and the second camera/IR sensor 702(2), respectively. For example, mounts, brackets, gears, slides, tracks, motors, wheels, pulleys, pneumatics, hydraulic cylinders, cables, screw drives, turntables, or other actuators may position, move, or orient the imaging system 700.

In some instances, the imaging system 700 may include lighting element(s) (e.g., the lighting element(s) 552) for illuminating the edible crowns or a portion of the edible crowns imaged by the imaging system 700. In some instances, the lighting element(s) may comprise white light LEDs or may include colored LEDs. Additionally, portions of the hood 120 above the edible crowns (e.g., on the bottom 400) may include blowers for removing debris, moisture, or other foliage for visibly capturing image(s) of the broccoli plants.

As discussed above, after capturing images of the edible crowns within the first row 704(1) and the second row 704(2), the computing system 500 may analyze the image(s). That is, after being imaged and while the harvester 100 moves, the edible crowns 124 pass through from underneath the hood 120, past the back edge 708 of the hood 120, and if ready for harvesting, may be harvested by the robotic arms 126.

Although FIG. 7 only illustrates one imaging system 700, the harvester 100 (or the hood 120) may include a corresponding number of imaging systems 516 for imaging broccoli plants. For example, a second imaging system may include a third camera/IR sensor for imaging edible crowns within a third row and/or a fourth camera/IR sensor for imaging edible crowns within a fourth row. This second imaging system may be spaced apart from the imaging system 700 in a direction towards the second end 404. Additionally, the imaging system(s) may be spaced apart by a known distance interposed between rows of broccoli plants. However, noted above, the imaging system(s) may be configured to move along multiple axes to reposition and image the edible crowns.

Figure 8B:
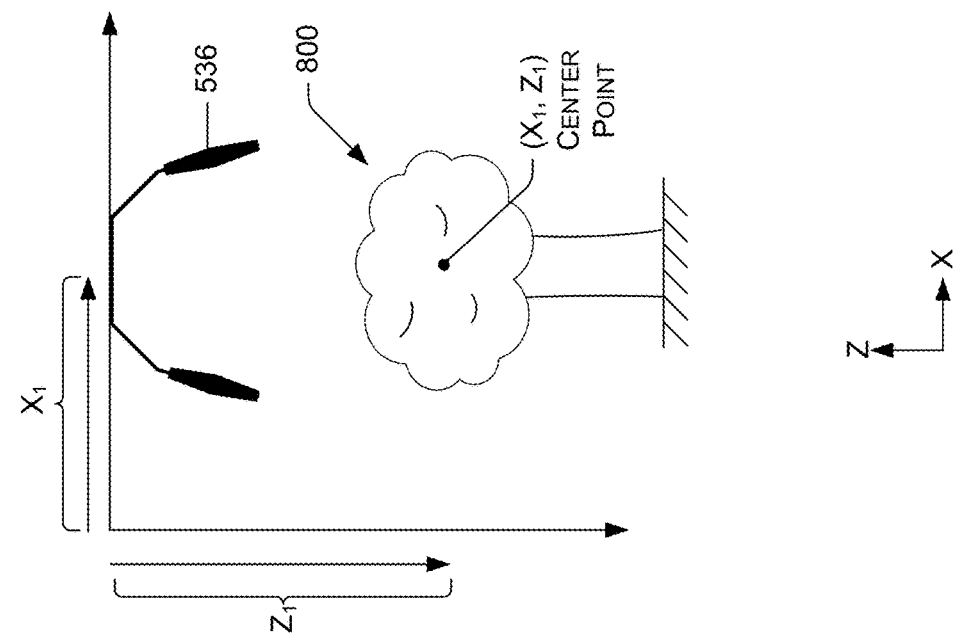
FIG. 8B illustrates a diagram for aligning example harvesting components of the harvester of FIG. 1 to harvest edible crowns, according to an embodiment of the present disclosure. The diagram of FIG. 8B illustrates aligning the harvesting components in a third direction with the edible crown, or along a third axis/plane.
Figure 8A:
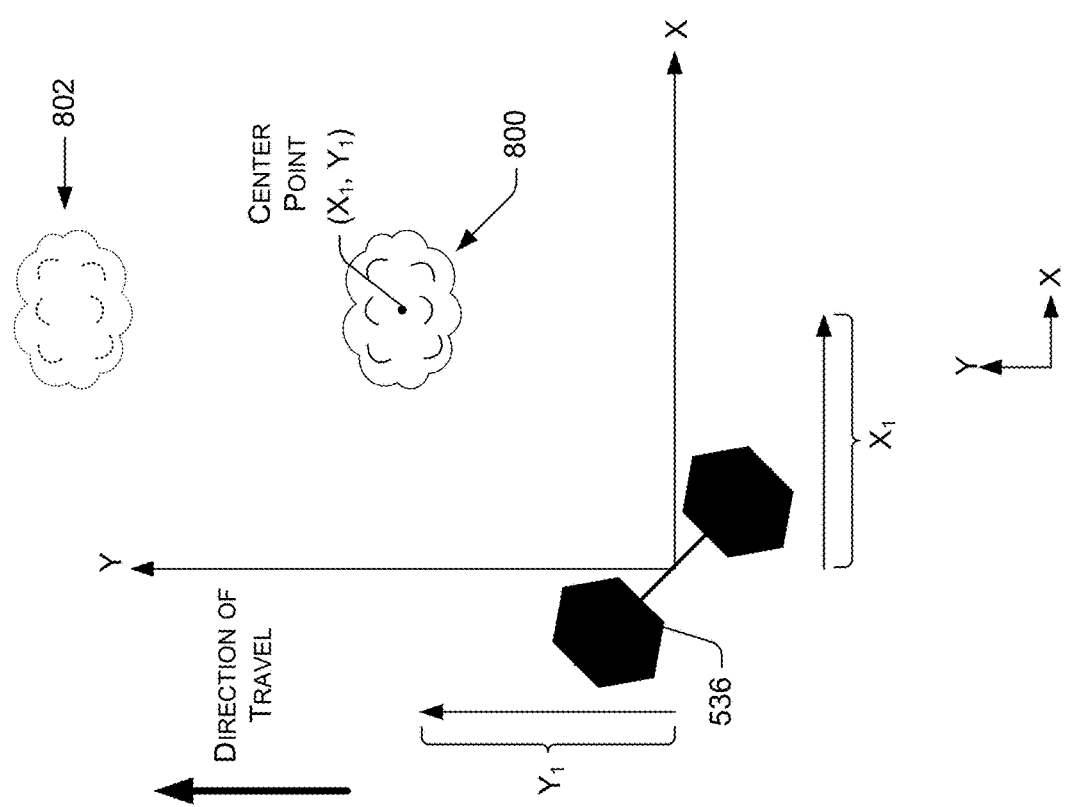
FIG. 8A illustrates a diagram for aligning example harvesting components of the harvester of FIG. 1 to harvest edible crowns, according to an embodiment of the present disclosure. The diagram of FIG. 8A illustrates aligning the harvesting components with the edible crown in a first direction and a second direction, or along a first axis/plane and a second axis/plane, respectively.

FIGS. 8A and 8B illustrate a diagram for aligning an end effector 536 relative to an edible crown 800 ready for harvesting. Initially, after determining that the edible crown 800 is ready for harvesting, the computing system 500 (or another component of the harvester 100) may determine a location associated with harvesting the edible crown 800. The end effector 536 may then position to the location (e.g., via a robotic arm, positioning system, etc.) to harvest the edible crown 800.

In some instances, the location of the edible crown 800 may be determined based at least in part on analyzing the image data 522, encoder data 546, and/or location data 548. For example, the computing system 500 may analyze the image data 522 for determining a location of the edible crown 800. The image data 522 may correspond to colored image data and/or a depth map, for determining a relative distance between the imaging system 516 and the edible crown 800 being imaged. This distance may be usable for determining a location of the edible crown 800 relative to the robotic arm 126, the end effector 536, or other portions of the harvester 100.

Additionally, or alternatively, the computing system 500 may analyze GPS coordinates of the navigational system 508 for determining a location of the harvester 100. This location may, in some instances, be relative to the end effector 536. In other instances, the location may be associated with a location of the edible crown 800. As such, the location of the edible crown 800 may be determined relative to the end effector 536 or relative to the harvester 100 for instructing or causing the end effector 536 to maneuver to the location for harvesting the edible crown 800.

The end effector 536 is shown positioned at an origin or resting position. In some instances, the origin may correspond to (0, 0, 0) in the (X, Y, Z) coordinate space. The end effector 536 may be configured to move from the origin to a location associated with the edible crown 800. For example, discussed above, the end effector 536 may operably couple to the robotic arm 126 and/or positioning system 538 that functions to move the end effector 536. As shown, the edible crown 800 may have a center point $(X_1, Y_1, Z_1)$ in coordinate space. In some instance, the center point may correspond to a center of mass and/or center of volume of the edible crown 800.

After determining the center point, the end effector 536 may effectuate to move to the center point. For example, if the origin is (0, 0, 0) in the (X, Y, Z) coordinate space, as shown in FIG. 8A, the end effector 536 may be moved by a distance $X_1$ in the X-direction and a distance $Y_1$ in the Y-direction. After moving by these distances in the X-direction and the Y-direction, respectively, the end effector 536 may be substantially centered above the edible crown 800 (e.g., disposed vertically above the edible crown 800). In some instances, the end effector 536 may first be moved in the X-direction and then in the Y-direction, or may first be moved in the Y-direction and then in the X-direction.

After being disposed vertically above the edible crown 800, the end effector 536 may descend downward upon the edible crown 800 in the Z-direction, by a distance $Z_1$. As shown in FIG. 8B the position $Z_1$ may correspond to a center of mass or center point of the edible crown 800. In some instances, the end effector 536 may not actually extend to the point $Z_1$. For example, extending to the point $Z_1$ may cause the end effector 536 to hit the edible crown 800, causing damage. Rather, the end effector 536 may include a center point for aligning with the center point of the edible crown 800. Therein, when these center points are aligned, the edible crown 800 may be positioned within the end effector 536, or within a center of the end effector 536.

In some instances, the distance $Z_1$ may correspond to a distance such that when the end effector 536 encloses around the edible crown 800, the end effector 536 engages with a stalk of the broccoli plant just below the edible crown 800. However, this distance may be varied to cut varying lengths of the stalk. Once the end effector 536 descends by the distance $Z_1$, the cutting mechanism 540 may sever the edible crown 800 from a remaining portion of the broccoli plant. Therein, the end effector 536 may travel to a collection point for transferring the edible crown 800.

The end effector 536 may then travel to a new location associated with harvesting a different edible crown, such as a subsequent edible crown 802 within the same row as the edible crown 800. For example, based on analyzing image data 522 of the subsequent edible crown 802, the encoder data 546, the location data 548, and/or GPS coordinates, a center point $(X_2, Y_2, Y_2)$ of the subsequent edible crown 802 may be determined. In some instances, the end effector 536 may return to the origin (0, 0, 0) after transferring the edible crown 800 at the collection point, and before traveling to the center point of the subsequent edible crown 802. In other instances, the end effector 536 may be configured to travel straight from the collection point to the center point of the subsequent edible crown 802. As such, the end effector 536 may be controlled in a three-dimensional coordinate space for harvesting edible crowns on a continuous basis.

Although the above discussion relates to positioning a single end effector 536, it is to be understood that the computing system 500 may respectively control a plurality of end effectors for harvesting a plurality of edible crowns across a plurality of rows. Furthermore, although the end effector 536 is shown including two fingers for grasping the edible crown 800, the end effector 536 may include more than or less than two fingers. As shown, the fingers of the end effector 536 may be shaped and/or profiled for cradling the edible crown 800 once cut. Additionally, the fingers may be oriented differently than shown.

Figure 9:
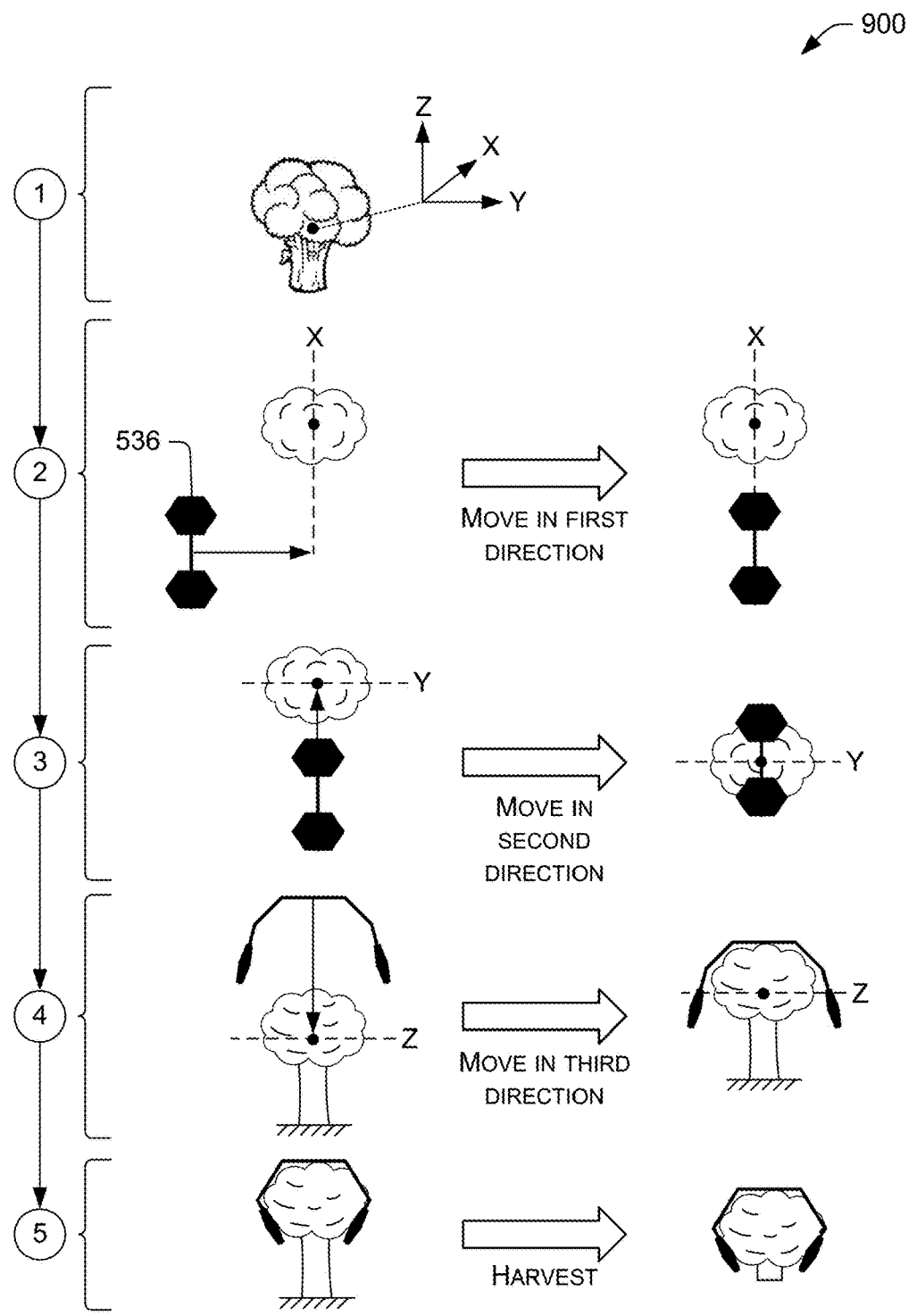
FIG. 9 illustrates an example diagram for aligning harvesting components of the harvester of FIG. 1 to harvest edible crowns, according to an embodiment of the present disclosure.

FIG. 9 illustrates a diagram 900 of successive steps for harvesting an edible crown. In some instances, steps illustrated in the diagram 9000 may be performed once the edible crown is determined to be harvested.

In some instances, at "1" the first step in harvesting the edible crown may include determining coordinates (e.g., X, Y, Z) associated with the edible crown. The coordinates, in some instances, may include a (X, Y, Z) center point of the edible crown. For example, after determining that the edible crown is ready for harvesting, the coordinates associated with harvesting the edible crown may be determined. As discussed above, the coordinates may be determined utilizing the image data 522, the location data 548 (e.g., GPS coordinates), and/or the encoder data 546. However, other methods may be used for determining the coordinates for instructing components of the harvester 100 to harvest the edible crown.

At "2" the second step in harvesting the edible crown may include positioning the end effector along a first axis (or plane) to align with the edible crown. For example, as shown, the end effector 536 may move in a first direction (e.g., in the X-direction) to align with the edible crown in a first direction, or align the with an X-plane extending through the center point. In some instances, aligning the end effector 536 with the edible crown in the first direction may include actuating the robotic arm 126 and/or the positioning system 538. For example, the computing system 500 may cause the end effector 536 to align with the edible crown in the first direction by instructing or actuating the robotic arm 126 and/or the positioning system 538.

At "3" the third step in harvesting the edible crown may include positioning the end effector 536 along a second axis (or plane) to align with the edible crown. For example, as shown, the end effector 536 may move in a second direction (e.g., in the Y-direction) to align with the edible crown in a second direction, or align with a Y-plane extending through the center point. In some instances, aligning the end effector 536 with the edible crown in the second direction may include actuating the robotic arm 126 and/or the positioning system 538. For example, the computing system 500 may cause the end effector 536 to align with the edible crown in the second direction by instructing or actuating the robotic arm 126 and/or the positioning system 538. In some instances, the steps "2" and "3" may be performed in reverse order, simultaneously, and/or substantially simultaneously.

In some instances, at "3" the end effector 536 may move in the second direction along the first axis (e.g., the X-axis). That is, the end effector 536 may maintain the alignment with the X-coordinate position of the center point while the end effector 536 moves in the second direction. As such, after moving in the second direction, the end effector 536 may be centered (or substantially centered) above the edible crown, in the first direction (or along the first axis/plane) and the second direction (or along the second axis/plane).

At "4" the fourth step in harvesting the edible crown may include descending the end effector 536 to align the end effector 536 along a third axis (or plane) associated with the edible crown. For example, as shown, the end effector 536 may descend in a third direction (e.g., in the Z-direction) to align with the edible crown in a third direction, or align with a Z-plane extending through the center point. In some instances, aligning the end effector 536 with the edible crown in the third direction may include actuating the robotic arm 126 and/or the positioning system 538. For example, the computing system 500 may cause the end effector 536 to align with the edible crown in the third direction by instructing or actuating the robotic arm 126 and/or the positioning system 538.

At "4" the end effector 536 may move in the third direction along the first axis (e.g., the X-axis/plane) and the second axis (e.g., the Y-axis/plane). That is, the end effector 536 may maintain the alignment with the X-coordinate position and the Y-coordinate position of the center point while the end effector 536 moves in the third direction. As such, after moving in the third direction, the end effector 536 may be centered (or substantially centered) on the edible crown, in the first direction, the second direction, and the third direction. Here, the end effector 536 may be disposed around, or substantially enclose, the edible crown. As shown, the end effector 536 at "4" may be in the open position and the fingers of the end effector 536 may be sized and spaced apart to allow the end effector 536 (and the fingers) to descend upon the edible crown.

At "5" the fifth step in harvesting the edible crown may include enclosing the end effector 536 on the edible crown and severing the edible crown from the stalk. For example, after disposed over the edible crown, actuators may actuate components of the end effector 536 to enclose around the edible crown. Thereafter, the cutting mechanism 540 may cut the stalk to separate the edible crown.

Although the end effector 536 is shown including two fingers for grasping the edible crown, the end effector 536 may include more than or less than two fingers, such as four fingers.

Figure 10:
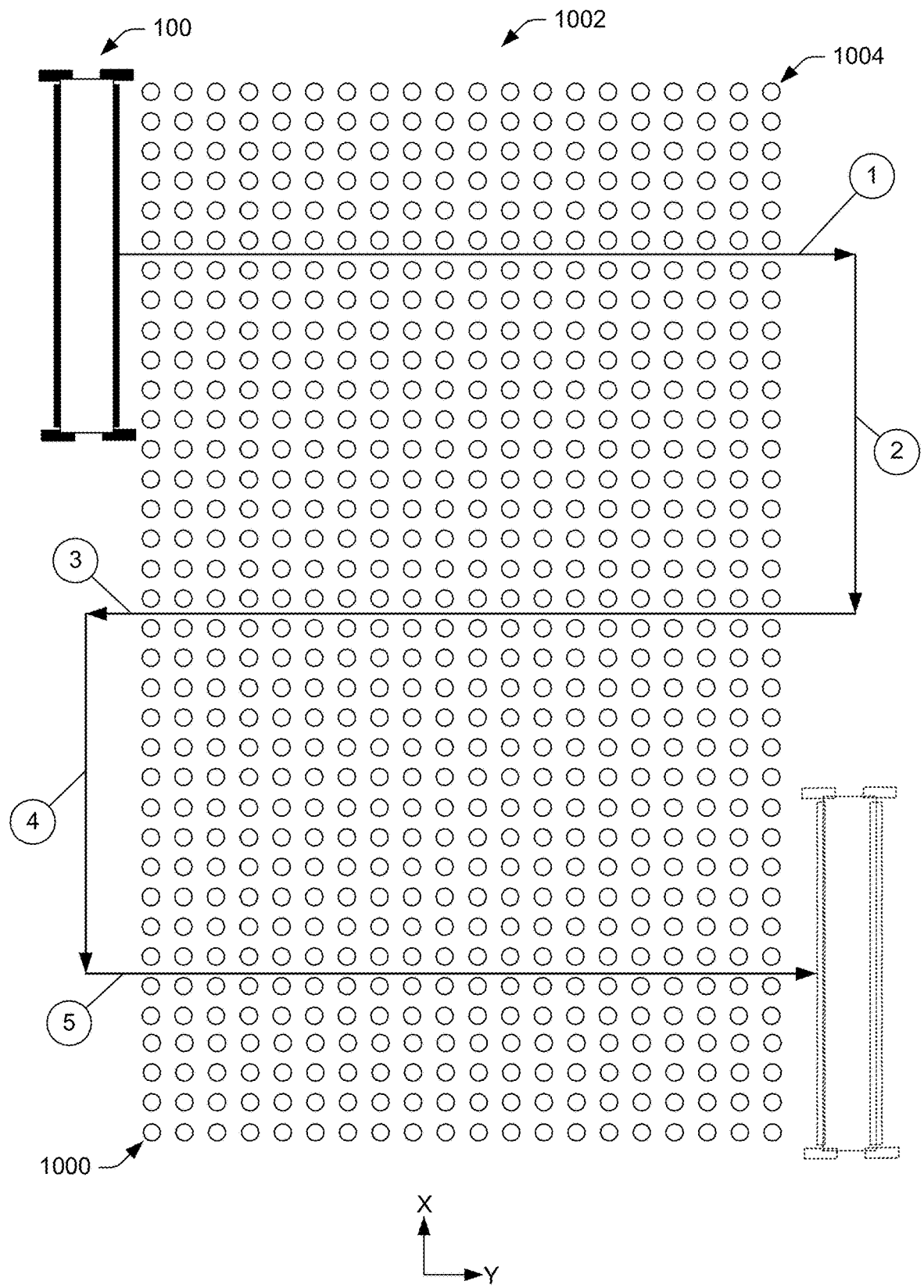
FIG. 10 illustrates a diagram showing an example route of the harvester of FIG. 1 for harvesting edible crowns, according to an embodiment of the present disclosure.

FIG. 10 illustrates an example diagram showing a route of the harvester 100 across rows of broccoli plants, or within a field 1002 of broccoli plants. As shown, initially, the harvester 100 may be aligned on a first side 1000 of the field 1002. In some instances, the harvester 100 may be configured to harvest multiple rows of broccoli plants at the same time. For example, as shown in FIG. 10, the harvester 100 may be configured to simultaneously harvest twelve rows of broccoli plants.

The harvester 100 is configured to harvest the broccoli plants by moving through the field 1002, from the first side to a second side 1004. For example, at "1" the harvester 100 may travel from the first side 1000 to the second side 1004 (Y-direction). Traveling at "1" may be substantially in a first direction, such as the Y-direction.

Once on the second side 1004, at "2" the harvester 100 may travel in a second direction, such as the X-direction. Traveling at "2" may center the harvester 100 for harvesting another twelve rows of broccoli plants, as the harvester 100 travels from the second side 1004 to the first side 100.

In some instances, after harvesting the first twelve rows at "1" the harvester 100 may pivot the wheels 90 degrees, for example, and travel in the X-direction. In this sense, the harvester 100 may avoid turning around, performing a "U-turn", and so forth. Rather, the wheels 108 of the harvester 100 may be independently steerable to reduce a turning radius of the harvester 100. As such, after harvesting rows of broccoli plants, the harvester 100 may simply turn the wheels 108 (e.g., 90 degrees clockwise), travel to other rows for harvesting, and the turn the wheels 108 back (e.g., 90 degrees counterclockwise).

Stated alternatively, because the harvester 100 may include multiple hoods (e.g., the hood 120 and the additional hood 200), the harvester 100 may not include a designated "front" and "back" or a particular direction of travel. That is, because the harvester 100 may include two hoods with imaging systems 516, the harvester 100 may not have a single direction of travel.

For example, at "3" the harvester 100 may travel from the second side 1004 to the first side 1000 to harvest an additional twelve rows of broccoli. At "3" the harvester may utilize different components for harvesting the broccoli plants. That is, because the harvester 100 is moving in a different direction of travel at "3" as compared to "1", different components may be used for imaging and/or harvesting the broccoli plants. For example, for harvesting the broccoli plants at "1" the harvester 100 may utilize imaging systems 516 on the hood 120 (e.g., a first hood), and harvesting the broccoli plants at "3" may utilize imaging systems 516 on the additional hood 200 (e.g., a second hood).

Therein, at "4" the harvester 100 may turn the wheels for aligning with another twelve rows of broccoli, and at "5," may harvest the broccoli plant. At "5" the harvester 100 may be traveling in a substantially similar direction of travel as "1" and therefore, may utilize the same imaging system 516 at "5" used to image the edible crowns at "1".

Therefore, from "1" to "5" the harvester 100 may harvest the broccoli plants without performing wide turns in between harvesting rows of broccoli plants. Instead, the wheels 108 may reposition after harvesting the rows of broccoli plants to limit an amount of time the harvester 100 takes before harvesting addition rows of broccoli plants.

Figure 11A:
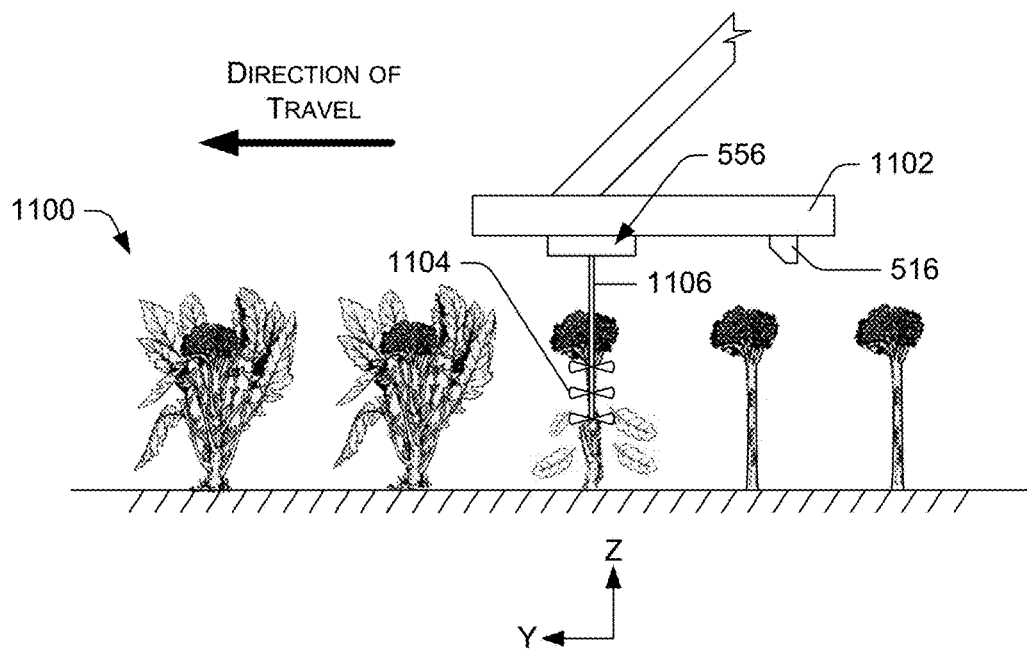
FIG. 11A illustrates an example de-leafing component of the harvester of FIG. 1 for removing leaves on the broccoli plant, according to an embodiment of the present disclosure.
Figure 11B:
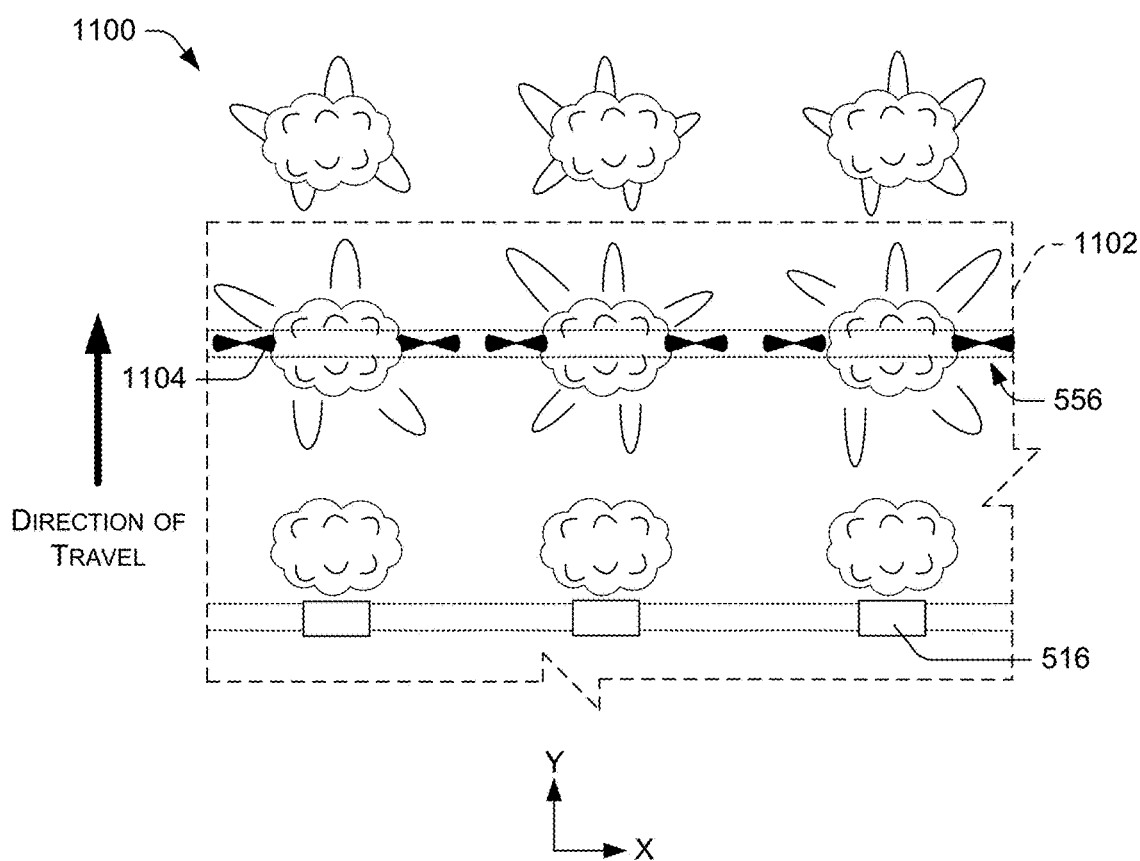
FIG. 11B illustrates the de-leafing component of FIG. 11A, according to an embodiment of the present disclosure.

FIGS. 11A and 11B illustrate the de-leafing component 556 for de-leafing broccoli plants or removing leaves from the broccoli plants. As discussed above, broccoli plants have an edible flower formed at the tip of the broccoli stalk.

However, healthy broccoli plants often have an abundance of leaves growing off the stalk that reside beneath, alongside of, and even above the edible crown. These leaves may obstruct the edible crown, which may impact the ability to accurately determine whether the edible crown is ready for harvesting.

For example, in some instances, the leaves may block or hinder the imaging system 516 being able to obtain a clear image of the edible crown. The subsequently obtained image(s) may fail to clearly indicate whether the edible crown is ready for harvesting. In turn, the computing system 500 may inaccurately determine that the edible crown is ready for harvesting or not ready for harvesting. Therefore, obtaining clear image(s) of the edible crown is important when analyzing whether the edible crown is ready for harvesting. The de-leafing component 556 may therefore remove leaves around the edible crown for obtaining clear and unobstructed image(s).

As shown in FIG. 11A, which represents a side view of the harvester 100, broccoli plants 1100 may pass underneath a hood 1102. The hood 1102 may be similar to and/or include similar components as the hood 120. As shown by the direction of travel, the broccoli plants 1100 may enter the hood 1102 having leaves disposed on the broccoli stalk and/or around the edible crown of the broccoli plants 1100. As the broccoli plants 1100 enter underneath the hood 120 the de-leafing component 556 may remove unwanted leaves. The de-leafing component 556 is shown extending from the hood 1102 in a direction towards the broccoli plants 1100 (e.g., towards the ground).

The de-leafing component 556 may include rotating blades 1104. In some instances, the rotating blades 1104 may resemble rotary knives or swinging flail knives. In some instances, the rotating blades 1104 may be spaced apart by a distance such that the rotating blades 1104 pass along a row of the broccoli plants 1100 to cut away the outer leaves of the broccoli plant 1100, leaving the broccoli plant 1100 unharmed and revealing the edible crown.

The rotating blades 1104 may be located on a shaft 1106 of the de-leafing component 556 that may be configured to rotate when powered. As shown in FIG. 11A, in some instances, each de-leafing component 556 may include a series of rotating blades 1104 that are disposed apart from one another along a length of the shaft 1106. For example, in some instances, the de-leafing component 556 may include three rotating blades 1104 that are spaced apart along the length of the shaft 1106 (Z-direction). In some instances, some of or all of the blades 1104 may be rotating blades, while some of or all of the blades may be stationary and/or fixed on the shaft 1106. In some instances, spacing the rotating blades 1104 in this manner may serve to remove leaves that extend upward towards the edible crown, and/or at different portions along the length of the stalk.

In some instances, the de-leafing component 556 may not remove all of the leaves from the stalk, but those leaves that extend close to the edible crown, or which are located near the top of the broccoli plant 1100. For example, the de-leafing component 556 may not remove leaves from the stalk that are located near the base of the broccoli plants 1100 (e.g., near the ground). Additionally, or alternatively, the de-leafing component 556 may be configured to remove outer leaves, such that when removed, no longer occlude the edible crown.

After the de-leafing component 556 removes the leaves, as shown in FIG. 11A, the leaves may be removed from the stalk. Therein, the imaging system 516 may image the edible crown as the edible crown pass or come within a field of view of the imaging system 516. Therein, as discussed above, the computing system 500 may determine whether to harvest the edible crown, and if so, the computing system 500 may instruct the robotic arm 126 to harvest the edible crown (via the end effector 536 and the cutting mechanism 540). As such, the de-leafing component 556 may be located in front of the imaging system 516 for removing the leaves to isolate the edible crown and prior to imaging.

FIG. 11B illustrates a top view of the hood 1102 and illustrates components of the hood 1102 in dashed lines to indicate the broccoli plants 1100 disposed therebeneath (Z-direction). In some instances, the harvester 100 may include de-leafing components 556 for individual rows of the broccoli plants 1100 being harvested. For example, the harvester 100 may include one or more de-leafing components 556 for each of the rows of broccoli plants 1100 being harvested. In some instances, the harvester 100 may include two de-leafing components for each row of broccoli plants 1100 being harvested. In such instances, a first de-leafing component 556 may be located on a first side of the broccoli plant 1100, or a first side of the row, while a second de-leafing component 556 may be located on a second side of the broccoli plant 1100, or a second side of the row. As the harvester 100 moves in the direction of travel the broccoli plants 1100 pass underneath the hood 120 whereby the de-leafing component(s) 556 may remove the leaves. After the leaves are removed, the imaging systems 516 may image the edible crowns.

In some instances, the de-leafing components 556 may be stationary (e.g., fixed position) or may be configured to move in one or more directions to trim or cut the leaves from multiple side(s) of the broccoli plants 1100. For example, information about the spacing of the broccoli plants 1100 within the rows (e.g., spacing between individual rows, spacing across rows, etc.) may be used to pre-position the de-leafing components 556 for oncoming broccoli plants 1100. Moreover, information about a height of the broccoli plants 1100 or a thickness of the stalk may be used to position the de-leafing components 556. In some instances, the de-leafing components 556 may not sever the leaves at a position where the leaves extend from the stalk (e.g., the leaves may not be cut off flush with the stalk). Rather, in some instances, the leaves may be cut off at positions that are halfway, two-thirds, etc. along the length of leaves. However, the de-leafing components 556 may effectuate to remove the portion of the leaves extending upward towards the edible crown, or which obstruct the edible crown. Therefore, removing the entire leaf from the stalk may be unnecessary.

In some instances, the de-leafing components 556 may be continuously powered given the continuous movement of the harvester 100. The harvester 100 may also include blowers or other fans for removing remints of the leaves once cut. For example, after the leaves are cut, remints may be located on the edible crown and may impact a quality of image(s) obtained. The blowers may remove unwanted leaves (or portions thereof) from the edible crown or area(s) in proximity to the edible crown.

In some instances, the de-leafing components 556 may also, in some instances, increase harvesting times. For example, as the de-leafing components 556 remove leaves, once harvested, the edible crowns may not have to be trimmed (either manually or with a separate machine) to remove unwanted leaves from the edible crown.

Although FIGS. 11A and 11B illustrate certain components or embodiments of the de-leafing components 556, the de-leafing components 556 may include other components and/or may be embodied differently. For example, rather than including the rotating blades 1104, the de-leafing components 556 may use stationary blades for removing the leaves. In some instances, the de-leafing components 556 may only remove leaves from one side, or multiple sides of the broccoli plants 1100. For example, it may be difficult to trim leaves on a leading or trailing side of the broccoli plants 1100, relative to the direction of travel. However, in some instances, the de-leafing components 556 may be coupled to, or include, actuators that move the de-leafing components 556 around the broccoli plants 1100 (e.g., to a front of the broccoli plants 1100). Additionally, or alternatively, in some instances, the harvester 100 may include more than or less than two de-leafing component 556 per row of the broccoli plants 1100, or the de-leafing components 556 may remove leaves across one or more rows. For example, the de-leafing components 556 may remove leaves from a first broccoli plant located in a first row of the broccoli plants 1100 and remove leaves from a second broccoli plant located in a second row of the broccoli plants 1100.

Furthermore, the de-leafing components 556 may also be located elsewhere on, or under, the hood 1102 and/or on other portions of the harvester 100. In some instances, the de-leafing components 556 may be an external device, machine, or apparatus, and which may not be coupled to the hood 1102 and/or the harvester 100. In some instances, the harvester 100 may include components for imaging the broccoli plants 1100 for first determining whether the broccoli plants 1100 need to be trimmed, or whether the leaves obscure the edible crown. That is, if the leaves are not obstructing the edible crown (i.e., a clear image may be obtained), then the leaves may not be removed and/or the de-leafing components 556 may not be actuated. If, however, the leaves are obstructing the edible crown, the de-leafing components 556 may be actuated to remove the leaves.

The blades of the de-leafing components 556 may also be different than as shown in FIGS. 11A and 11B (e.g., size, shape, angles, etc.). For example, individual de-leafing components 556 may include a first rotary (or stationary) blade arranged substantially horizontally relative to the shaft 1106, a second rotary blade arranged substantially vertically relative to the shaft 1106, and/or a third rotary blade disposed at another angle relative to the shaft 1106. In some instances, the blades 1104 may rotate about the shaft 1106, or may rotate at various angles relative to the shaft 1104 (e.g., perpendicular). These arrangements may serve to cut the leaves from the stalk to accommodate for the different growing characteristics of the leaves.

Figure 12A:
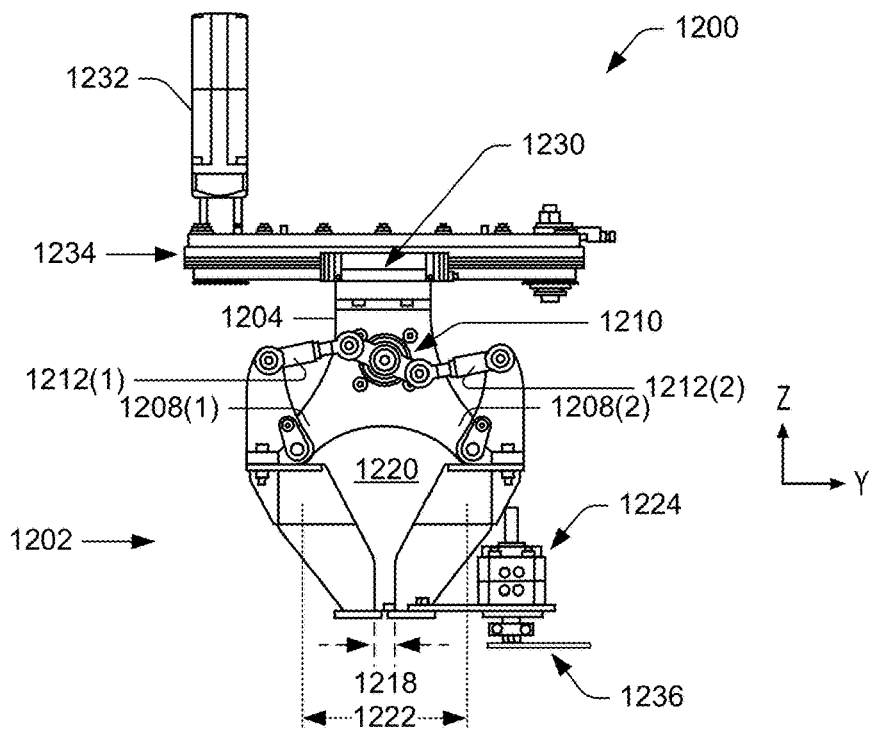
FIG. 12A illustrates a first view of example harvesting components of the harvester of FIG. 1, according to an embodiment of the present disclosure. In some instances, the harvesting components may include a robotic arm and/or an end effector for grasping the edible crown and a cutting mechanism for severing the edible crown from the broccoli plant. The end effector may operably transition between an open state and a closed state for grasping the edible crown and releasing the edible crown at a collection point.
Figure 12B:
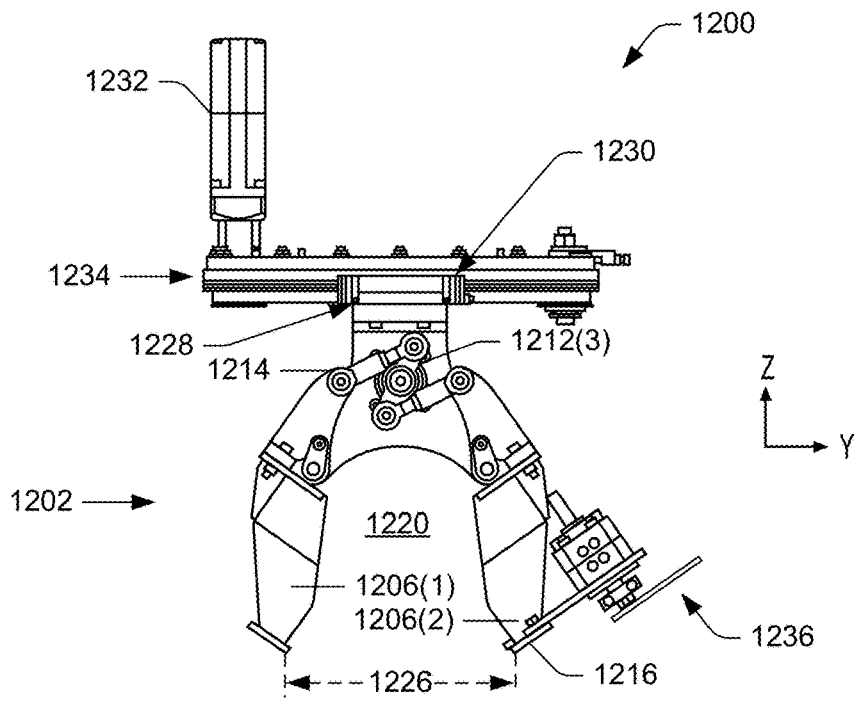
FIG. 12B illustrates a second view of the harvesting components of FIG. 12A, according to an embodiment of the present disclosure.

FIGS. 12A and 12B illustrate a detailed view of a robotic arm 1200 of the harvester 100. In some instances, the robotic arm 1200 may be similar to, represent, and/or include features as described above with regard to the robotic arm 126.

The robotic arm 1200 includes an end effector 1202. The end effector 1202 may be similar to, represent, and/or include features as described above with regard to the end effector 536. The end effector 1202 is configured to transition between an open position. FIG. 12A illustrates the end effector 1202 in the closed position and FIG. 12B illustrates the end effector 1202 in the open position.

Generally, and as discussed above with regard to the end effector 536, the end effector 1202 may represent a gripper that grasps edible crowns of broccoli plants ready for harvesting. In the open position, the end effector 1202 may descend unto or over edible crowns. In the closed position, the end effector 1202 may grasp onto edible crowns (or portions of the stalk) for retaining edible crowns within the end effector 1202.

In some instances, the end effector 1202 may include a body 1204 and fingers attached to the body 1204. The body 1204 may include one or more arms or wings that extend outward for receiving or coupling to the fingers 1206. In some instances, the end effector 1202 may include two fingers as shown in FIGS. 12A and 12B, such as a first finger 1206(1) and a second finger 1206(2) (collectively, referred to herein as "the fingers 1206"). However, in some instances, the end effector 1202 may include more than two fingers, such as three fingers, four fingers, and/or any other number of fingers.

The fingers 1206 may be equidistantly spaced apart from one another on the body 1204. In such instances, depending on the number of the fingers 1206, the body 1204 may include a corresponding number of wings for receiving the fingers 1206. For example, as shown, the body 1204 may include a first wing 1208(1) and a second wing 1208(2) (collectively referred to herein as "the wings 1208"), where the first finger 1206(1) couples to the body 1204 at the first wing 1208(1) and the second finger 1206(1) couples to the body 1204 at the second wing 1208(2). In such instances, the first wing 1208(1) and the second wing 1208(2) may be spaced 180 degrees apart from another. By way of another example, if the end effector 1202 includes three fingers, the three fingers may be radially spaced apart from one another by 120 degrees. In such instances, the body 1204 of the end effector 1202 may include three wings that are radially spaced apart from one another by 120 degrees.

The fingers 1206 may pivotably couple to the wings 1208 for allowing the fingers 1206 to transition between the open position and the closed position. For example, as shown in FIG. 12A, the fingers 1206 may be cinched or positioned close together. As shown in FIG. 12B, in the open position, the fingers 1206 may be separated or disposed apart from one another. The fingers 1206 may pivotably couple to the wings 1208, respectively, using bearings, bushings, and so forth. In some instances, the fingers 1206 may pivot about a rod, pin, or shaft disposed through the fingers 1206 and the wings 1208, respectively, and which function to adjoin the fingers 1206 to the body 1204.

The end effector 1202 (or the robotic arm 1200) may include an actuator 1210 for transitioning the end effector 1202 (or the fingers 1206) between the open position and the closed position. In some instances, the actuator 1210 may include a linear actuator or a rotary actuator. For example, FIGS. 12A and 12B illustrates that a rotatory actuator (rotating actuator) may be disposed on, through, or within the body 1204, and which couples to the fingers 1206 for moving the fingers 1206 between the open position and the closed position.

The actuator 1210 may couple to the fingers 1206 via linkages, connectors, bars, and so forth. For example, as shown and in some instances, the fingers 1206 may couple to the actuator 1210 via one or more linkages, such as a first linkage 1212(1), a second linkage 1212(2), and a third linkage 1212(3). In instances where the end effector 1202 includes more than two fingers, the end effector 1202 may include additional actuators and/or linkages.

The first linkage 1212(1) may couple to an end of the fingers 1206, such as a first end 1214 of the first finger 1206(1). As shown, the first linkage 1212(1) may couple at a location proximally or substantially located at the first end 1214 to increase a clamping force of the first finger 1206(1). The first linkage 1212(1) may pivotably couple to the first end 1214 of the first finger 1206(1) using pins and bearings, for example. Similarly, the second linkage 1212(2) may pivotably couple to the first end 1214 of the second finger 1206(2). The third linkage 1212(3) may couple to the actuator 1210 and include opposing ends that are coupled to the first linkage 1212(1) and the second linkage 1212(2), respectively. The connection between the third linkage 1212(3) with the first linkage 1212(1) and the second linkage 1212(2) may pivot to allow components of the end effector 1202 to move and swivel.

As the actuator 1210 rotates, for instance, the first linkage 1212(1), the second linkage 1212(2), and the third linkage 1212(3) collectively operate to transition the end effector 1202 between the open state and the closed state. For example, when the actuator 1210 is actuated, the third linkage 1212(3) may pull or push on the first linkage 1212(1) and the second linkage 1212(2), respectively, for moving the fingers 1206. Whether the third linkage 1212(3) pulls or pushes on the first linkage 1212(1) or the second linkage 1212(2) may depend on a direction of rotation of the actuator 1210. For example, shown in FIG. 12A, the third linkage 1212(3) may be substantially horizontal, and when rotated (clockwise or counterclockwise), the second linkage 1212(2) may be substantially vertical. Therein, actuating the actuator 1210 in an opposite direction (counterclockwise or clockwise) may transition the end effector 1202 back to the closed position. This movement of the third linkage 1212(3) therefore forces the first linkage 1212(1) and the second linkage 1212(2) to be disposed at respective positions.

The first linkage 1212(1), the second linkage 1212(2), and the third linkage 1212(3) may be hingedly or pivotably coupled to one another to allow the first linkage 1212(1), the second linkage 1212(2), and the third linkage 1212(3) to transition between the open position and the closed position. In some instances, the first linkage 1212(1), the second linkage 1212(2), and/or the third linkage 1212(3) may be adjustable in length to accommodate for varying sizes of edible crowns.

The fingers 1206 may include a second end 1216, opposite the first end 1214, that may engage with a stalk of the broccoli plants 104, below the edible crown of the broccoli plant when the end effector 1202 transitions to the closed position. In the closed position, in some instances, a distance 1218 may be interposed between the second ends 1216 of the fingers 1206 may be such that the second ends 1216 grip, or cinch, around the stalk. In other instances, the fingers 1206 may not grip or clasp onto the stalk such that the stalk may translate within the distance 1218 (X, Y, and/or Z-directions).

Additionally, in the closed position, the fingers 1206 may define an internal space 1220 occupied by the edible crown, or which the edible crown is configured to reside within while being harvested and/or after being harvested. The internal space 1220 may include a volume of sufficient size to prevent the fingers 1206 bruising or otherwise damaging the edible crown. In other words, the fingers 1206, in the closed position, may not pinch sides of the edible crown. For example, a distance 1222 may be interposed between internal sides of the fingers 1206, where the distance 1222 is of sufficient size to not pinch and damage the edible crown. Additionally, a vertical dimension of the internal space 1220 (Z-direction) may be of sufficient height to prevent a top of the edible crown bruising against the body 1204. The internal space 1220 of the end effector 1202 may be predetermined according to an average size of edible crowns that are ready for harvesting. In some instances, a size (e.g., volume) of the internal space 1220 may be adjusted via extending the first linkage 1212(1), the second linkage 1212(2), and/or the third linkage 1212(3).

The end effector 1202 is shown including a cutting mechanism 1224 for cutting the stalk of the broccoli plant to separate the edible crown from the rest of the broccoli plant. In some instances, the cutting mechanism 1224 may be similar to, represent, and/or include features as described above with regard to the cutting mechanism 540. The cutting mechanism 1224 may cut the stalk when the end effector 1202 is in the closed position, or as the end effector 1202 transitions, or is transitioning, to the closed position. In some instances, the second ends 1216 of the fingers 1206 may grip, or cinch, around the stalk to hold the stalk while the cutting mechanism 1224 cuts the stalk.

The cutting mechanism 1224 may include a blade 1236 that is configured to rotate, spin, or swivel for cutting through a thickness of the stalk. For example, the cutting mechanism 1224 may include an actuator configured to rotate the blade 1236 relative to the second finger 1206(2) for cutting through the stalk. In some instances, the actuator that powers the blade 1236 may be air actuated or electric. The blade 1236 may couple to the actuator of the cutting mechanism 1224 via a sprocket, for example. When powered or instructed, the actuator may cause the blade 1236 to rotationally cut through the stalk (e.g., about the Z-axis). In some instances, the blade 1236 may cut through the stalk in a direction (Y-direction) that is substantially perpendicular to a direction in which the broccoli plant grows (Z-direction). However, in some instances, the cutting mechanism 1224 may be disposed on the second finger 1206(2) (or other fingers) differently than shown, or may be orientated differently than shown for cutting through the stalk. For example, the cutting mechanism 1224 may include scissor-like or guillotine blades that converge upon one another for cutting the stalk. Additionally, or alternatively, the blade 1236 may include a saw/disc that rotates for cutting through the stalk.

As shown, the cutting mechanism 1224 may be disposed on one of the fingers 1206 (e.g., the second finger 1206(2)) for cutting the stalk below the edible crown, at a position proximate to the second end 1216 of the fingers 1206. For example, the cutting mechanism 1224 may cut the stalk of the broccoli plant at a position just below the edible crown. As such, because the second ends 1216 of the fingers 1206 are configured to engage the stalk at a position below the edible crown, the cutting mechanism 1224 may cut the stalk just below the edible crown. However, the amount of stalk that remains attached to the edible crown may be varied according to consumer preferences. Additionally, once cut, in some instances, the blade 1236 may remain in a cut position (e.g., not retracting) such that the stalk of the cut edible floret rests on the blade 1236. The blade 1236 in this position may prevent the stalk and/or the edible crown from falling out of the fingers 1206 and/or may otherwise secure the edible crown within the fingers 1206.

Between the first end 1214 and the second end 1216, the fingers 1206 hingedly couple to the wings 1208 of the body 1204. In some instances, the wings 1208 may pivotably couple to the fingers 1206 at a position more proximate to the first end 1214 of the fingers 1206 than the second end 1216 of the fingers 1206.

Meanwhile, in the open position, a distance 1226 is interposed between the second ends 1216 of the fingers 1206. The distance 1226 may be of sufficient size to allow the end effector 1202, or the fingers 1206, to fit over and around the edible crown. Once descended over the edible crown, the fingers 1206 of the end effector 1202 may close to secure the edible crown.

In some instances, the body 1204 may include a base end connected to the robotic arm 1200, as shown and discussed above. In some instances, the robotic arm 1200 and/or the body 1204 may couple to a positioning system (e.g., the positioning system 538) for maneuvering the end effector 1202. For example, FIGS. 12A and 12B illustrate a system for positioning the end effector 1202, which may be used in lieu of or in addition to the robotic arm 1200 for positioning the end effector 1202.

For example, the body 1204 is shown including a base 1228 connected to a carrier 1330. The carrier 1230 may be disposed on a track or rail system 1234 for translating the end effector 1202 along different axes and planes. For example, the rail system 1234 may include slides or rails that function to translate the end effector 1202 along the X-plane and the Y-plane. The carrier 1230 may couple within slots of the rail system 1234, or within rails of the rail system 1234. The carrier 1230 may include drivers or components for translating the end effector 1202 along the X-plane and the Y-plane. Such translation may allow the end effector 1202 to be centered over the edible crown, or otherwise positioning the end effector 1202 for harvesting the edible crown.

In some instances, the rail system 1234 may include mounts, brackets, gears, slides, tracks, motors, wheels, pulleys, pneumatics, hydraulic cylinders, cables, screw drives, turntables, or other actuators that position, move, or orient the end effector 1202. The components of the rail system 1234 may be electric or motorized and controlled by logic or other hardware of the harvester 100 (e.g., the computing system 500), according to the position of the edible crown.

The rail system 1234, in some instances, may be coupled to a support 1232 that functions to dispose the end effector 1202 at various heights. For example, the support 1232 may telescope or extend to various lengths to position the end effector 1202 at various positions. In some instances, the support 1232 may extend the end effector 1202 at varying heights on/along the Z-plane. Accordingly, the combination of the rail system 1234 and the support 1232 may position the end effector 1202 at various coordinate spaces for harvesting the edible crowns. Additionally, in some instances, the robotic arm 1200 may include additional motors that rotate or pan the end effector 1202 at varying degrees. This positioning may increase a grip of the end effector 1202 on the edible crown.

Although the robotic arm 1200 is described as coupling or including certain components for positioning the end effector 1202 relative to the edible crown, other components may be included. For example, other pneumatic systems, tracks, or slides may be used for positioning the end effector 1202 relative to the edible crown. In such instances, the end effector 1202 may be disposed on or coupled to a track or positioning system, or may couple to motors, drives, or other actuators that align the end effector 1202 relative to the edible crown (or a portion thereof). In some instances, however, the robotic arms 1200 may include actuators that maneuver the end effector 1202 in horizontal and/or vertical directions (e.g., three-dimensional space) relative to the edible crown. Additionally, in some instances, the actuators may also tilt or dispose the end effector 1202 at certain angles relative to the edible crown. Aligning the end effector 1202 in this manner may allow the end effector 1202 to securely grip the edible crown, and without damaging the grip.

In some instances, the rail system 1234 and/or the support 1232 may be configured to translate to account for the movement of the harvester 100. For example, as the end effector 1202 grasps the edible crown in the closed position the harvester 100 may still be moving in the direction of travel. To prevent the end effector 1202 pulling (e.g., tugging) on the edible crown and/or the stalk, the rail system 1234 and/or the robotic arm 126 may move in an opposite direction. This opposite direction may be opposite to the direction of travel of the harvester 100 to keep the end effector 1202 centered over the edible crown while the cutting mechanism 1224 cuts the stalk. Moving the end effector 1202 in a direction opposite to the direction of movement may prevent pulling of the edible crown, which in turn, may prevent damage to the edible crown. In some instance, the rail system 1234 may move the end effector 1202 in the opposite direction, at the same speed as the harvester 100 is traveling.

The fingers 1206 may include a single unitary body or may be assembled from multiple components. In some instances, the fingers 1206 may include a similar shape, contours, or features from the first end 1214 to the second end 1216, or may include certain features proximate to the second end 1216 for receiving the edible crown. For example, below a position at which the fingers 1206 couple to the wings 1208 (Z-direction), the fingers 1206 may include features for holding the edible crown within the end effector 1202. By way of example, the fingers 1206 may include troughs, channels, flanges, or other features that engage with a bottom or underneath side of the edible crown. Such engagement may cusp, cradle, and secure the edible crown within the internal space 1220 of the end effector 1202. In some instances, the cusping nature of the edible crown may substantially prevent the edible crown from rotating, rocking, or otherwise repositioning within the end effector 1202 while being transferred to the collection point(s). As such, once cut, the edible crown may rest on the fingers 1206 (or portions thereof), within the internal space 1220.

The computing system 500 may communicatively couple or control the robotic arm 1200 and components thereof, such as the actuator 1210, the cutting mechanism 1224, the carrier 1230, etc. For example, the computing system 500 may instruct the actuator 1210 to move between the open position and the closed position, and may instruct the cutting mechanism 1224 to cut the stalk once the edible crown is within the end effector 1202.

Additionally, while the above discussion relates to the linkages or the fingers 1206 being disposed at respective angles or positions, other embodiments are envisioned. Additionally, while FIGS. 12A and 12B illustrate a certain position of the fingers 1206 in the closed position and the open position, respectively, the fingers 1206 may be disposed farther apart in the open position and/or spaced closer together in the closed position, for example. The fingers 1206 may also include alternate contours as shown and described.

Figure 13A:
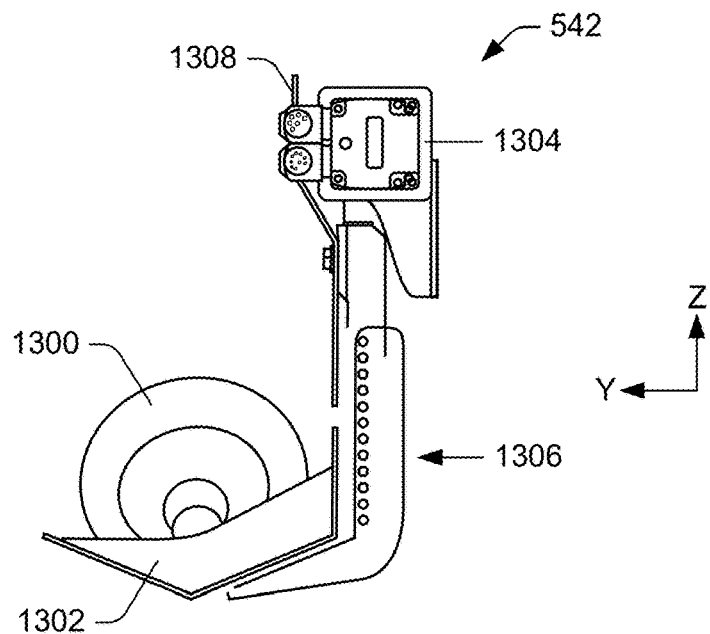
FIG. 13A illustrates an example transferring component of the harvester of FIG. 1 for receiving harvested edible crowns from harvesting components, and transferring the edible crown(s) to other portions of the harvester, such as a conveyor belt, according to an embodiment of the present disclosure. The transferring component may represent a flipper that operably transitions between different positions, such as a first position for receiving harvested edible crowns from the end effector, and a second position, for transferring the edible crowns.
Figure 13B:
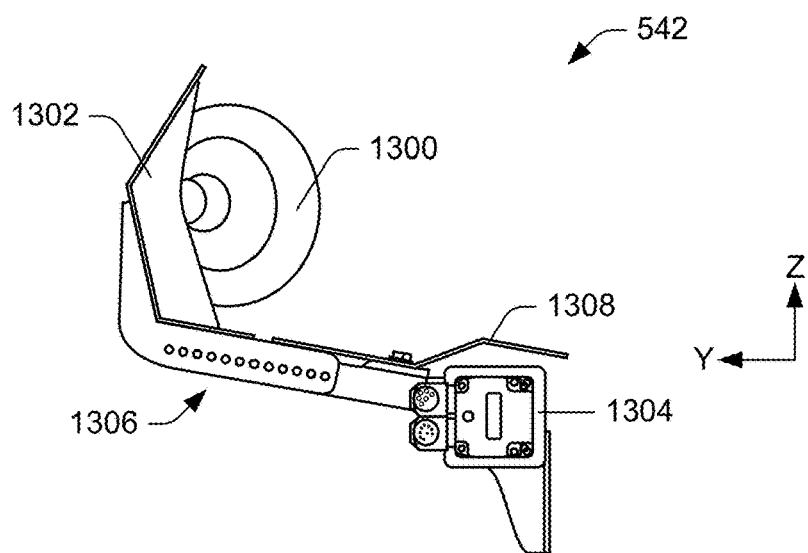
FIG. 13B illustrates the transferring component of FIG. 13A, according to an embodiment of the present disclosure.

FIGS. 13A and 13B illustrate the flipper 542 of the harvester 100 receiving edible crowns 1300 from the robotic arms 126 and transferring the edible crowns 1300 to other portions of the harvester 100, such as conveyor belts and/or collection points.

The flipper 542 is configured to transition or move between positions for receiving the edible crowns 1300 and transferring the edible crowns 1300. For example, FIG. 12A illustrates the flipper 542 in a first position or state for receiving the edible crowns 1300. In some instances, the first position may be considered a "down position" whereby the flipper 542 receives the edible crowns 1300 from the robotic arms 126. After receiving the edible crowns 1300, the flipper 542 may actuate and transition to a second position or state, as shown in FIG. 12B. The second position may be considered an "up position" whereby the flipper 542 transfers the edible crowns 1300 to a conveyor belt for further processing (e.g., trimming, cleaning, etc.).

The flipper 542 includes a cradle, container, bin, or basket 1302 for receiving the harvested edible crowns 1300. The basket 1302 may include sidewalls to secure the edible crowns 1300 within the basket 1302 and while transferring the edible crowns 1300. For example, as shown in FIG. 13A, the harvested edible crown 1300 may reside within the basket 1302 and secured therein by the sidewalls. This way the edible crown 1300 may not roll out of the basket 1302 and onto the ground.

The basket 1302 is shown disposed at one end, or a first end, of the flipper 542. At a second end, the flipper 542 may couple to, or include, an actuator 1304. The actuator 1304 may function to transition the flipper 542 between the first position and the second position for receiving the edible crowns 1300 and transferring the edible crowns 1300. For example, as shown in FIG. 13B, the actuator 1304 may actuate the flipper 542 upwards (Z-direction). As shown, the actuator 1304 may be rotatable about the X-axis between the first position and the second position.

In some instances, the actuator 1304 may act with such speed and movement such that at the second position, the edible crown 1300 is ejected from the basket 1302. That is, from the first position, the flipper 542 may move into the second position at a sufficient speed such that the edible crown 1300 may be ejected from the basket 1302 and onto the conveyor belt, for example. However, the ejection and/or speed at which the edible crown 1300 is ejected may be controlled and/or limited to avoid bruising to the edible crown 1300. Furthermore, in some instances, rather than "ejecting" the edible crown 1300, the basket 1302 may be rotated over-center whereby the edible crown 1300 may fall out, roll out, or slide out of the basket 1302 and onto the conveyor belt, for example.

The transfer of the edible crown 1300 from the basket 1302 may therefore be controlled or performed in a multitude of manners. After the basket 1302 no longer contains the edible crown 1300, the actuator 1304 may transition the flipper 542 back to the first position from receiving another edible crown.

The basket 1302, or the flipper 542, in some instances may include sensors for determining when an edible crown is placed within the basket 1302. These sensors may detect when the edible crown 1300 is within the basket 1302 for actuating the flipper 542 and transferring the edible crown 1300. For example, a weight sensor or image sensor may detect that the edible crown 1300 is in the basket 1302, and in response, the actuator 1304 may be actuated for transition flipper 542 to the second position.

Additionally, or alternatively, in some instances, the actuator 1304 may be actuated according to a schedule or predetermined interval of time. For example, the flipper 542 may receive edible crowns every three seconds or in some other interval of time. The flipper 542 may therefore be actuated every three seconds, regardless of whether an edible crown is within the basket 1302. The three second interval may allow enough time for the flipper 542 to receive an edible crown, transfer the edible crown, and return back to the second position for receiving an additional edible crown. In some instances, the flipper 542 and/or the basket 1302 may receive more than one edible crown at an instance, and accordingly, in the second position, may transfer more than one edible crown.

In some instances, the flipper 542 may further include an adjustment mechanism 1306 that adjusts a height, or length, of the basket 1302 for accommodating different sizes of edible crowns. A guard 1308 is further provided to prevent damage or debris collecting on the actuator 1304.

FIGS. 14-20 illustrate various processes related to harvesting edible crowns. The processes described herein are illustrated as collections of blocks in logical flow diagrams, which represent a sequence of operations, some or all of which may be implemented in hardware, software, or a combination thereof. In the context of software, the blocks may represent computer-executable instructions stored on one or more computer-readable media that, when executed by one or more processors, program the processors to perform the recited operations. Generally, computer-executable instructions include routines, programs, objects, components, data structures and the like that perform particular functions or implement particular data types. The order in which the blocks are described should not be construed as a limitation, unless specifically noted. Any number of the described blocks may be combined in any order and/or in parallel to implement the process, or alternative processes, and not all of the blocks need be executed. For discussion purposes, the processes are described with reference to the environments, devices, architectures, diagrams, and systems described in the examples herein, such as, for example those described with respect to FIGS. 1-13, although the processes may be implemented in a wide variety of other environments, architectures, and systems.

Figure 14:
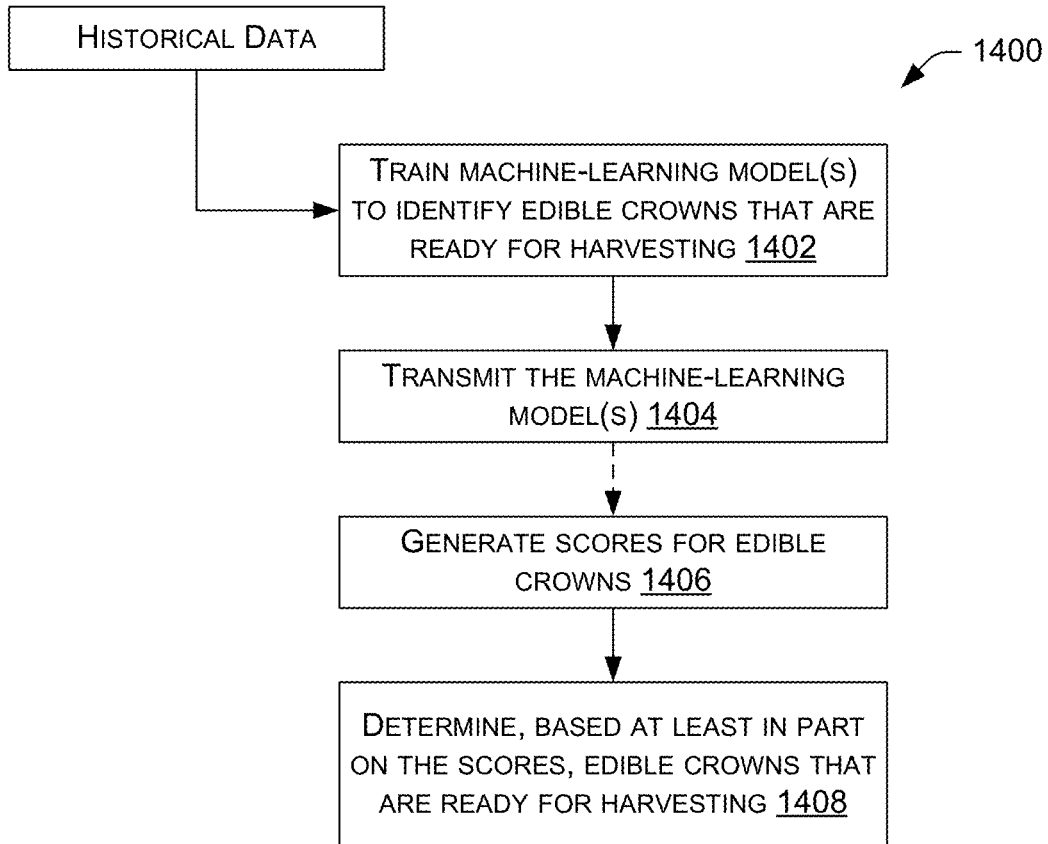
FIG. 14 illustrates an example process for training one or more machine-learning model(s) for use in determining whether an edible crown is ready for harvesting, according to an embodiment of the present disclosure.

FIG. 14 illustrates an example process 1400 for training ML model(s), such as the ML model(s) 524. In some instances, the process 1400 may be performed by the computing system 500 and/or the remote computing resource(s) 530, or components thereof. The ML model(s) 524 may be trained to determine trust scores related to determining whether edible crowns are ready for harvesting.

As discussed above, the harvester 100 may include components that collect and store data associated with the edible crowns. This data may be made available to the remote computing resource(s) 530 for training the ML model(s) 524. Additionally, or alternatively, the remote computing resource(s) 530 may store and/or maintain a database associated with the edible crowns. Regardless of where the data is stored, this data may be organized within a datastore in any suitable manner to associate individual edible crowns with relevant portions of the data.

At 1402, the process 1400 may train one or more machine-learning model(s) to identify edible crowns that are ready for harvesting. For example, the remote computing resource(s) 530 may include a training component that trains the ML model(s) 524 using historical data. In some instances, the remote computing resource(s) 530 may access a portion of the historical data associated with a sampled set of harvested edible crowns and use the sampled data to train the ML model(s) 524. Additionally, or alternatively, the historical data may include unharvested edible crowns for training the ML model(s) 524 to identify and label the edible crowns that are not ready for harvesting.

In some instances, the portion of the data used as training data may be represented by a set of characteristics that is labeled with a label indicating whether the characteristic is representative of an edible crown ready for harvesting. For example, if an edible crown has a particular size, this "size" may be used as one of multiple labels for a particular edible crown. In this manner, a supervised learning approach may be taken to train the machine learning model(s) to predict edible crowns that are ready for harvesting.

In some instances, the remote computing resource(s) 530 may include a training component configured to train ML model(s) 524 using a portion of the image data (and/or historical data) in the datastore that is associated with a sampled set of edible crowns as training data to obtain the trained ML model(s) 524. Discussed herein, the trained ML model(s) 524 is/are usable by the scoring component 526 to determine scores 528 (e.g., trust scores) for a plurality of edible crowns.

Additionally, in some instances, at least some of the historical data may have been generated from edible crowns that were previously harvested. For example, the historical data accessed may represent edible crowns that were previously harvested and ready for harvesting, based on the edible crown exhibiting certain characteristic(s) (e.g., size, shape, color, etc.). As part of training the ML model(s) 524, the remote computing resource(s) 530, via the training component, may label each characteristic of the sampled set of edible crowns with a label that indicates whether the characteristic is associated with an edible crown that is ready for harvesting or a characteristic that is associated with an edible crown not being ready for harvesting. Examples of labels are described herein, such as whether a size of the edible crown is indicative of the edible crown being ready for harvesting, whether a color of the edible crown is indicative of the edible crown being ready for harvesting, whether a shape of the edible crown is indicative of the edible crown being ready for harvesting, whether an amount of buds within the edible crown is indicative of the edible crown being ready for harvesting, and so forth. However, the labels may correspond to other types of characteristics.

In some instances, training the ML model(s) 524 at 1402 may include applying or setting weights for machine learning. These weights may apply to a set of features derived from the historical data. In some embodiments, the weights may apply to parameters that are internal to the ML model(s) 524 (e.g., weights for neurons in a hidden-layer of a neural network). These internal parameters of the ML model(s) 524 may or may not map one-to-one with individual input features of the set of features. It is to be understood that the ML model(s) 524 may be retrained using updated historical data (e.g., the image data 522) to obtain a newly trained ML model(s) 524 that is adapted to recently harvested edible crowns and/or unharvested edible crowns. This allows the ML model(s) 524 to adapt, over time, to changing characteristics.

At 1404, the process 1400 may transmit the machine-learning model(s). For example, the remote computing resource(s) 530 may transmit, via the network(s) 532, the ML model(s) 524 to the harvester 100. For example, given that the remote computing resource(s) 530 may have a computational capacity that exceeds that of the harvester 100, in some instances, the remote computing resource(s) 530 may train the ML model(s) 524 and then provide the ML model(s) 524 to the harvester 100 for use while harvesting the edible crowns.

At 1406, the process 1400 may generate scores for the edible crown(s). For example, the scoring component 526 of the computing system 500 may score a plurality of edible crowns that are being imaged by the imaging system 516 using the ML model(s) 524. For example, the scoring component 526 may access, from the computer-readable media 504 and/or receive in real-time, the image data 522 associated with the imaged edible crowns, provide the image data 522 as input to the ML model(s) 524, and generate, as output from the ML model(s) 524, the scores 528 associated with the plurality of edible crowns. These scores 528 relate to the probabilities of edible crowns being ready for harvesting, or not ready for harvesting. For example, in the case of the edible crown not being ready for harvesting a "low" score may relate to the probability of the edible crown not being ready for harvesting. In the case of the edible crown being ready for harvesting a "high" score may relate to the probability of the edible crown being ready for harvesting. Different classifiers, or identifiers, may be used or associated with those edible crowns that are ready for harvesting and those edible crowns that are not ready for harvesting.

At 1408, the process 1400 may determine which edible crowns are ready for harvesting, based at least in part on the scores. For example, with the scores 528 determined for a plurality of edible crowns, the computing system 500 may be configured to determine whether the edible crowns are ready for harvesting. In some instances, the computing system 500 may receive the scores 528 and compare these scores 528 to a threshold, or certain predetermined level. If the scores 528 are greater than the threshold, or satisfy the threshold, the edible crown may be flagged for harvesting. If the scores 528 are less than the threshold, or do not satisfy the threshold, the edible crown may be not be flagged for harvesting. In some instances, the edible crown may be flagged for not harvesting (e.g., an indication to not harvest the flagged edible crown).

In some instances, rather than outputting a score, the ML model(s) 524 may output indications or labels indicating whether the edible crowns are ready for harvesting and/or not ready for harvesting. For example, the indications or labels may indicate whether the edible crowns are "ready" or "not ready." In some instances, the edible crowns not be associated with a color, size, density, or maturity per se for comparison with reference characteristic(s), but rather, a label indicating whether the edible crown is ready or not ready for harvesting. As part of this process, the ML model(s) 524 may be trained via data associated with mature edible crowns and/or immature edible crowns to know how to recognize edible crowns that are ready and not ready for harvesting.

Figure 15:
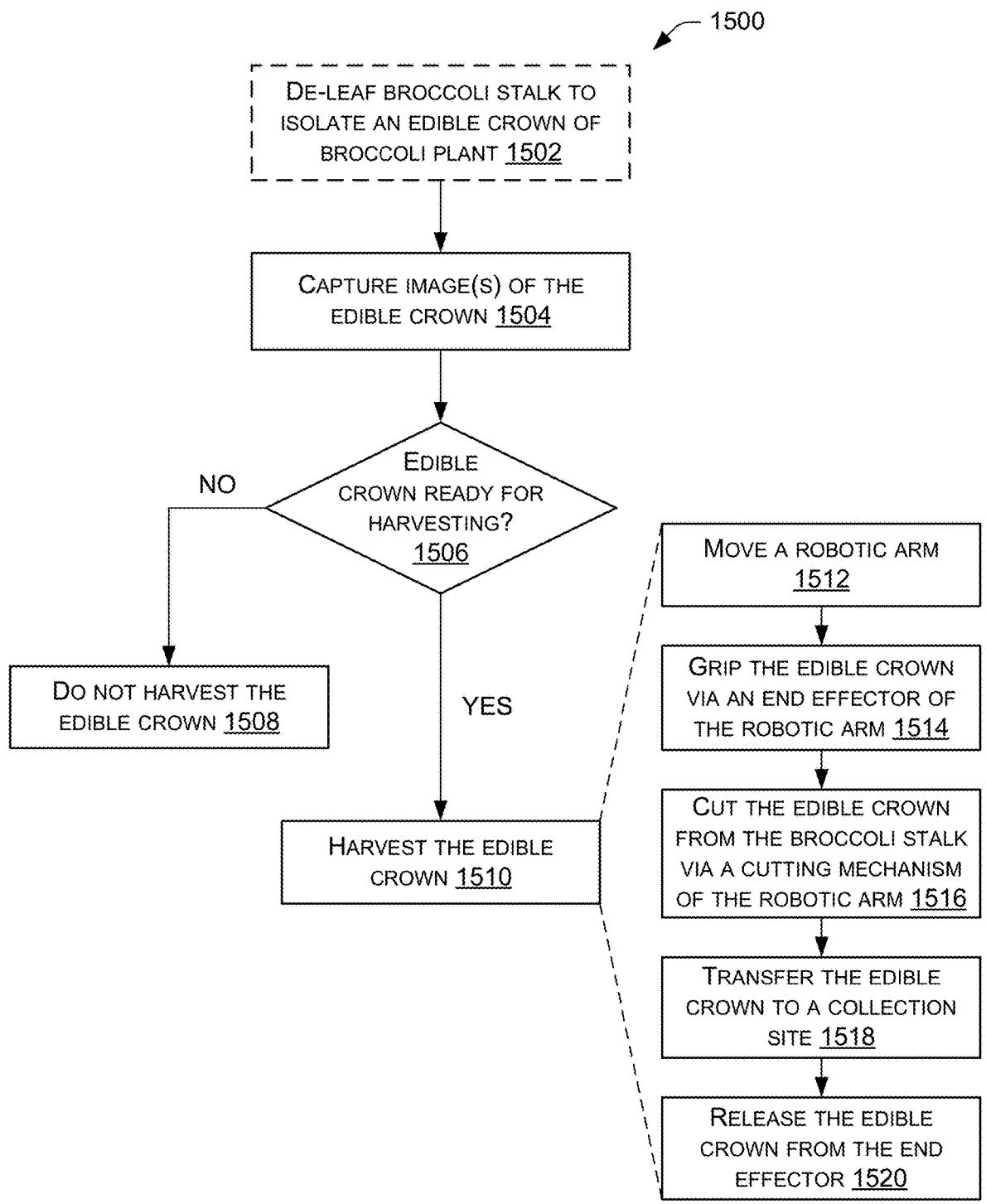
FIG. 15 illustrates an example process for determining whether an edible crown is ready for harvesting, according to an embodiment of the present disclosure.

FIG. 15 illustrates an example process 1500 for determining whether an edible crown is ready for harvesting, and if the edible crown is ready for harvesting, causing the edible crown to be harvested. In some instances, the process 1500 may be carried out or performed by the harvester 100 and/or components thereof, such as the computing system 500.

Initially, in some instances, the process 1500 may begin at 1502 with de-leafing the broccoli stalk to remove leaves and isolate the edible crown. For example, as discussed above, removing leaves around or proximate to the edible crown may increase the imaging system 516 capturing clear image(s) of the edible crown.

At 1504, the process 1500 may capture image(s) of the edible crown. For example, the imaging system 516 may capture one or more image(s) of the edible crown. The image(s) may be used by the harvester 100, such as the computing system 500, for determining whether to harvest the edible crown.

At 1506, the process 1500 may determine whether the edible crown is ready for harvesting. For example, the computing system 500 may analyze the image(s) captured by the imaging system 516 to determine whether the edible crown is ready for harvesting (e.g., mature). For example, the ML model(s) 524 may be utilized to determine whether the edible crowns are ready for harvesting. Additional details of determining whether the edible crown is ready for harvesting are discussed herein with regards to the process 1600, as shown and discussed in relation to FIG. 16. At 1506, if the process 1500 determines that the edible crown is not ready for harvesting, the process 1500 may follow the "NO" route and proceed to 1508. For example, the process 1500 may determine that the edible crown is not mature for harvesting (e.g., not of sufficient size, color, height, etc.).

At 1508, the process 1500 may determine to not harvest the edible crown. For example, as a result of determining that the edible crown is not ready for harvesting, the harvester 100 may bypass harvesting the edible crown to allow the broccoli plant further time to grow and mature. Determining to not harvest the edible crown may involve the robotic arm 126 refraining from actuating the end effector 536 to harvest the edible crown.

In some instances, the process 1500, as a result of not harvesting the edible crown, may record a location of the edible crown for use at a later instance when traveling back to the edible crown. For example, the computing system 500 may store information associated with the unharvested edible crowns. In instances where the edible crown is not ready for harvesting, the computing system 500 may record information as to a location of the edible crown, and/or characteristic(s) of the unharvested edible crown (e.g., size, shape, color, etc.). These characteristic(s) may be used for determining when the edible crown is projected to be ready for harvesting. For example, the characteristic(s) may indicate that the unharvested edible crown will be ready for harvesting in one week. After one week, the edible crown may then be harvested during another harvesting cycle. Furthermore, recording a location of the unharvested edible crown may allow the harvester 100 (or an operator thereof) to precisely locate the unharvested edible crown within the field 102.

Alternatively, if at 1506 the process 1500 determines that the edible crown is ready for harvesting, the process 1500 may follow the "YES" route and proceed to 1510.

At 1510, the harvester 100 may harvest the edible crown. For example, upon determining that the edible crown is ready for harvesting, the computing system 500 may cause the harvester 100 (or components thereof) to actuate and harvest the edible crown.

As shown, harvesting the edible crown at 1510 may include various sub-operations 1512-1520. For example, at 1512, harvesting the edible crown may include instructing the robotic arm 126 to move to a position associated with harvesting the edible crown (e.g., X, Y, and Z coordinates). Once the robotic arm 126 is in position, at 1514, the robotic arm 126 may grip the edible crown via the end effector 536. For example, the end effector 536 may transition from the open state to the closed state to grip the broccoli plant (e.g., the stalk) and encapsulate the edible crown. Thereafter, at 1516, the cutting mechanism 540 of the robotic arm 126 may cut the stalk to separate the edible crown from the stalk. At 1518, the robotic arm 126 may then transfer the edible crown, which is retained within the end effector 536, to a collection site (e.g., flipper 542, conveyor belt 130, etc.). Once at the collection site, at 1520, the robotic arm 126 may release the edible crown from the end effector 536 to transfer the edible crown to the collection site.

However, although the process 1500 of harvesting the edible crown at 1510 is shown and discussed as including certain operations, the robotic arm 126 (or the harvester 100) may be configured to perform any number or series of operations for harvesting the edible crown. Furthermore, although the process 1500 is described as determining whether to harvest a single edible crown, the process 1500 may be performed for a plurality of edible crowns across multiple rows of broccoli plants, in parallel, for harvesting edible crowns within more than one row simultaneously.

Figure 16:
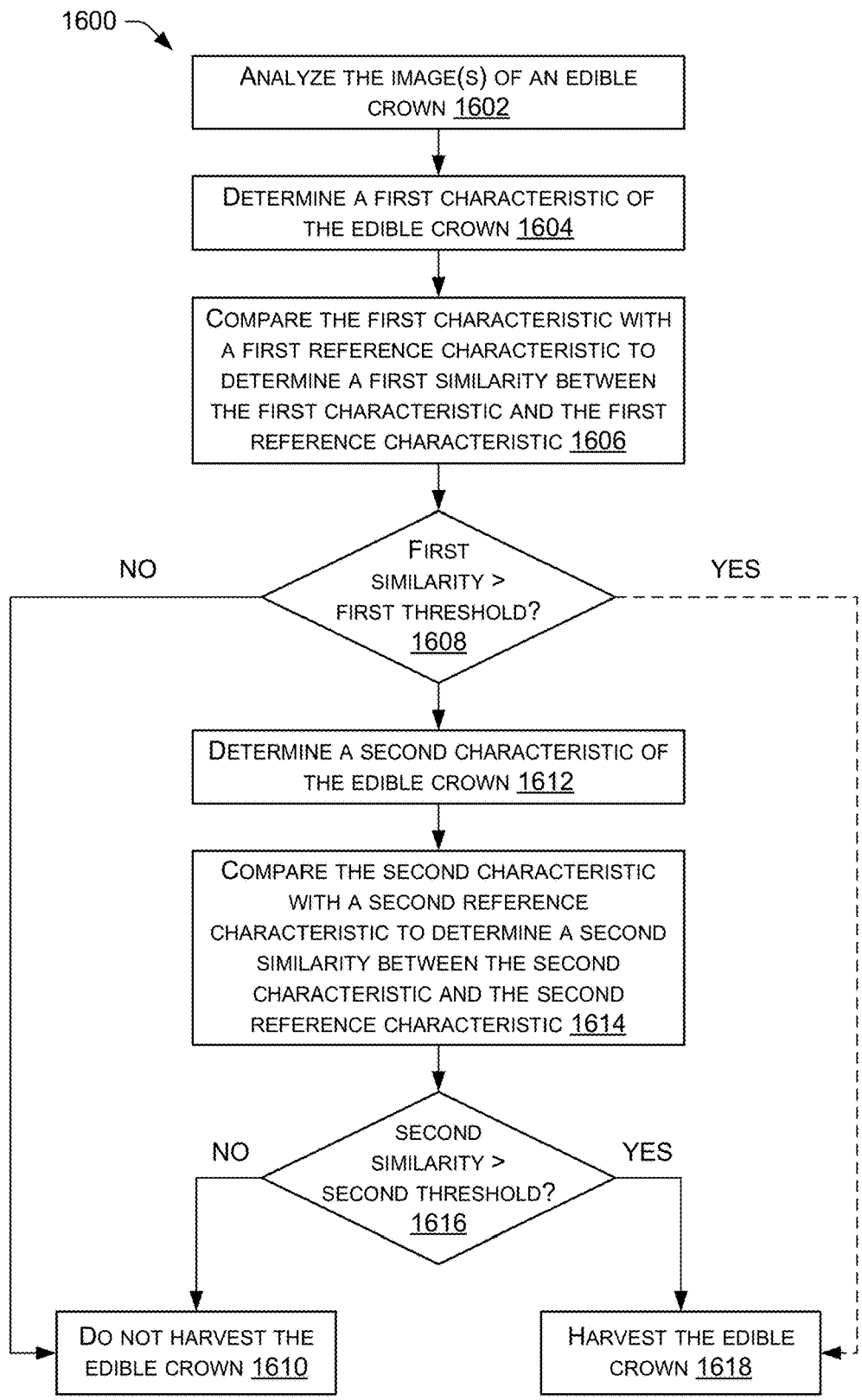
FIG. 16 illustrates an example process for determining whether to harvest an edible crown, according to an embodiment of the present disclosure.

FIG. 16 illustrates an example process 1600 for determining whether to harvest an edible crown, or whether an edible crown is ready for harvesting, based on determining one or more characteristic(s) of the edible crown. The process 1600 may be carried out or performed by the harvester 100 and/or components thereof, such as the computing system 500.

At 1602, the process 1600 may analyze image(s) of the edible crown. For example, after the imaging system 516 captures image(s) of the edible crown, the image(s) (color and/or depth) may be analyzed via the computing system 500. In some instances, the image(s) may be analyzed by the imaging system 516 (e.g., integrated processor(s)). Analyzing the image(s) may also include utilizing the ML model(s) 524 for determining certain objects or characteristics within the image(s). For example, the ML model(s) 524 may analyze the image(s) to determine objects of interest or known objects.

At 1604, the process 1600 may determine a first characteristic of the edible crown. For example, after analyzing the image(s), the computing system 500 may determine a first characteristic of the edible crown. In some instances, the first characteristic may include a size of the edible crown, a color of the edible crown, a density of the edible crown, a number of buds within the edible crown, and so forth. These characteristics may assist in determining whether the edible crown is ready for harvesting and/or is otherwise mature for harvesting. Noted above, the first characteristic (and other characteristics of the edible crown) may be determined using the ML model(s) 524 that are trained to analyze the image(s) and identify the characteristics (e.g., as discussed above with regard to FIG. 14 and the process 1400) of edible crowns that are ready for harvesting and/or of edible crowns that are not ready for harvesting.

At 1606, the process 1600 may compare the first characteristic with a first reference characteristic to determine a first similarity between the first characteristic and the first reference characteristic. For example, as part of identifying or determining the first characteristic, the process 1600 may compare the first characteristic with a reference characteristic for use in determining whether the edible crown is ready for harvesting. The reference characteristic may correspond to, or be associated with, the first characteristic for use in comparison and determining whether the edible crown is ready for harvesting.

For example, if the first characteristic is a color of the edible crown, the first reference characteristic may be a reference color. The color of the edible crown may be compared against the reference color to determine a similarity therebetween. That is, at 1606, the process 1600 may determine a similarity between the color of the edible crown to a reference color that is indicative of the edible crown being ready for harvesting (e.g., green). The ML model(s) 524 may determine the first similarity.

In some instances, the reference color may be represented as a range of colors. In this sense, the reference characteristics may be associated with a range of values (e.g., colors, size, buds, etc.) for comparison with the characteristics of the edible crown. For example, the range of colors may span between light green and dark green, where edible crowns having a color within this range are ready for harvesting. These "colors" within the range may be associated with certain hues, tints, shades, contrast, and/or other features for comparing the color of the edible crown. Accordingly, the color of the edible crown may not require an "exact match"

to a certain color, but rather, may fall within a range of colors that are indicative of the edible crown being ready for harvesting.

As such by comparing the first characteristic with the first reference characteristic, the process 1600 may determine a similarity therebetween. This similarity, as alluded to above, may indicate a closeness of the first characteristic with the first reference characteristic, where the closeness is used to determine whether the edible crown is ready for harvesting. In some instances, as part of determining the first similarity, the process 1600 may determine a confidence of the first similarity. That is, the confidence of the first similarity may represent a confidence of the first characteristic being similar to, or not similar to, the first reference characteristic. In some instances, the similarity may be represented as a score.

At 1608, the process 1600 may determine whether the first similarity is greater than a first threshold. For example, as part of comparing the first characteristic to the first reference characteristic, the process 1600 may determine a relatedness (i.e., how close of a match between the first characteristic and the first reference characteristic). If the first similarity is greater than the first threshold (e.g., satisfies the threshold), this may indicate that the first characteristic is closely related (e.g., similar) to the first reference characteristic (and that the edible crown may be ready for harvesting). Alternatively, if the first similarity is less than first threshold (e.g., does not satisfy the threshold), this may indicate that the first characteristic is not closely related to the first reference characteristic (and that the edible crown may not be ready for harvesting).

If at 1608, the process 1600 determines that the first similarity is less than the first threshold, the process 1600 may follow the "NO" route and proceed to 1610. For example, if the color of the edible crown is yellow, or a yellowish green, the process 1600 may determine that edible crown is not ready for harvesting because the edible crown does not include a color representative being ready for harvesting (e.g., light green to dark green). Noted above, as part of this determination, the process 1600 may compare hues, tints, or shades of the color of the edible crown to determine that the edible crown is not ready for harvesting. In some instances, the process 1600 may determine an average color of the edible crown and/or a color within a center of the edible crown.

At 1610, the process 1600 may determine to not harvest the edible crown. For example, as a result of determining that the first similarity is not greater than the first threshold, the process 1600 may determine to not harvest the edible crown. As a result of determining that the edible crown is not ready for harvesting, the harvester 100 may bypass harvesting the edible crown to allow the edible crown (or the broccoli plant) further time to grow and mature. Determining to not harvest the edible crown may involve the robotic arm 126 refraining from actuating the robotic arm 126 and the cutting mechanism 540 to harvest the edible crown.

Alternatively, if at 1608, the process 1600 determines that the first similarity is greater than the first threshold, the process 1600 may follow the "YES" route and proceed to 1612. For example, if the color of the edible crown is green, the process 1600 may determine that the edible crown may be ready for harvesting because the edible crown has a color that is representative of the edible crown being ready for harvesting (e.g., including a color between light green and dark green).

At 1612, the process 1600 may determine a second characteristic of the edible crown. For example, the computing system 500 may determine a second characteristic of the edible crown, such as color, size, shape, a number of buds, etc. The second characteristic may be another of the characteristics of the edible crown, different than the first characteristic at 1604. By way of example, the second characteristic may be a size of the broccoli (e.g., area, largest cross-sectional dimension, diameter, height, etc.).

At 1614, the process 1600 may compare the second characteristic with a second reference characteristic to determine a second similarity between the second characteristic and the second reference characteristic. For example, as part of identifying or determining the second characteristic, the process 1600 may compare the second characteristic with a reference characteristic for use in determining whether the edible crown is ready for harvesting. The reference characteristic may correspond to, or be associated with, the second characteristic for determining whether the edible crown is ready for harvesting. For example, the second reference characteristic may be a reference size (e.g., reference area, reference cross-sectional dimension, reference diameter, reference height, etc.).

The size of the edible crown may be compared against the reference size to determine a similarity therebetween. That is, at 1614, the process 1600 may determine a similarity between the size of the edible crown to a reference size that is indicative of the edible crown being ready for harvesting. In some instances, the similarity may be represented as a score.

In some instances, the reference size may be represented as a range of sizes. For example, the range of sizes may span between 4.0 inches and 5.75 inches, where edible crowns having a size within this range may be ready for harvesting. In some instances, however, the reference size may be associated with a single value, such that if edible crowns are greater than 4.0 inches, the edible crowns may be deemed ready for harvesting. As such by comparing the second characteristic with the second reference characteristic, the process 1600 may determine a similarity therebetween, where this similarity may indicate a closeness of the second characteristic with the second reference characteristic.

In some instances, as part of determining the second similarity, the process 1600 may determine a confidence of the second similarity. That is, the confidence of the second similarity may represent a confidence of the second characteristic being similar to, or not similar to, the second reference characteristic.

At 1616, the process 1600 may determine whether the second similarity is greater than a second threshold. For example, as part of comparing the second characteristic to the second reference characteristic, the process 1600 may determine a relatedness (i.e., how close of a match between the second characteristic and the second reference characteristic). If the second similarity is greater than the second threshold (e.g., satisfies the threshold), this may indicate that the second characteristic is closely related (e.g., similar) to the second reference characteristic. Alternatively, if the second similarity is less than second threshold (e.g., does not satisfy the threshold), this may indicate that the second characteristic is not closely related to the second reference characteristic.

If at 1616, the process 1600 determines that the second similarity is less than the second threshold, the process 1600 may follow the "NO" route and proceed to 1610. For example, if the size of the edible crown is less than 4.0 inches, the process 1600 may determine that edible crown is not ready for harvesting because the edible crown is not of sufficient size for harvesting.

Alternatively, if at 1616, the process 1600 determines that the second similarity is greater than the second threshold, the process 1600 may follow the "YES" route and proceed to 1618. For example, if the size of the edible crown is 5.25, the process may determine that the edible crown may be ready for harvesting because the edible crown has a size that is representative of an edible crown being ready for harvesting.

At 1618, the process 1600 may harvest the edible crown. For example, the computing system 500 may instruct components of the harvester 100 (e.g., robotic arm 126) to harvest the edible crown. In some instances, by comparing two characteristics of the edible crown against reference characteristics, before harvesting the edible crown, the process 1600 may be confidence that the edible crown is mature or ready for harvesting. That is, by comparing multiple characteristics of the edible crowns with characteristics representative of edible crowns ready for harvesting, the process 1600 may be sure, or confident, (e.g., the thresholds) that the edible crowns are ready for harvesting.

However, as shown, in some instances, the process 1600 may proceed to 1618 from 1608 after determining that the first characteristic is greater than the first threshold similarity. For example, in some instances, only one characteristic may be used to determine that the edible crown is ready for harvesting. For example, if the process 1600 has a certain confidence that the edible crown is ready for harvesting, after analyzing the first characteristic, the process 1600 may determine to harvest the edible crown. For example, in some instances, the process 1600 may proceed to 1618 from 1608 if the process 1600 is confident of the first similarity above a threshold confident level. The process 1600 may therefore be confident of the color of the edible crown, and that the edible crown is therefore ready for harvesting. As a result, the process 1600 may cause the edible crown to be harvested.

In some instances, the process 1600, from 1608 may proceed to 1612 if the process 1600 has a confidence that is less than the certain confidence level. For example, if at 1608 the process 1600 determines that the color of the edible crown is green, but is not that confident in the decision (e.g., below a threshold confidence level), the process 1600 may proceed to 1612 for analyzing the second characteristic of the edible crown to determine whether to harvest the edible crown.

In some instances, the process 1600 may dynamically determine the first characteristic and/or the second characteristic for the edible crowns. For example, in analyzing the image(s), the computing system 500 may identify which characteristics of the edible crowns are most identifiable, or which characteristics the computing system 500 has the highest confidence. In this sense, in some instances, the computing system 500 may identify a first characteristic of a first edible crown and a second characteristic of the first edible crown, which may be different than a first characteristic of a second edible crown and a second characteristic of the second edible crown. For example, the computing system 500 may analyze color and size for the first edible crown to determine whether the first edible crown is ready for harvesting, and may analyze color and the number of buds for the second edible crown to determine whether the second edible crown is ready for harvesting. In some instances, however, the first characteristic and the second characteristic may be same across the edible crowns. For example, the first characteristic may be color and the second characteristic may be size. Here, the process 1600 may determine the color and the size of the edible crown to determine whether the edible crown is ready for harvesting.

Furthermore, while the FIG. 16 and the process 1600 are illustrated and described as comparing two characteristics for determining whether the edible crown is ready for harvesting, more than or less than two characteristics may be used. For example, noted above, the process 1600 may only use a single characteristic, such as size or color, to determine whether the edible crown is ready for harvesting by comparing the size or color to reference values. The size or the color of the edible crown, alone, in some instances, may be dispositive (or above a certain confidence threshold) that the edible crown is ready for harvesting. Using a single characteristic, as opposed to multiple, may increase a harvesting rate of the harvester.

Alternatively, the process 1600 may compare three, four, five, etc. characteristics for determining whether the edible crown is ready for harvesting. In some instances, the process 1600 may analyze additional characteristics of the edible crown in instances where the process 1600 has a confidence less than a certain threshold. For example, if the process 1600 is confident less than a certain threshold that the color of the edible crown is representative of an edible crown ready for harvesting, the process 1600 may analyze an additional characteristic of the edible crown for determining whether the edible crown is ready for harvesting.

Although the process 1600 is discussed herein as determining characteristics of the edible crown, in some instances, the process 1600 may determine characteristics of other portions of the broccoli plant of ruse in determining whether the edible crown (or the broccoli plant) is ready for harvesting. For example, the process 1600 may analyze the image(s) to determine a thickness of the stalk, a height of the broccoli plant, and/or a size of the leaves for use in determining whether the edible crown is mature and ready for harvesting. Although the process 1600 is described as determining whether to harvest a single edible crown, the process 1600 may be performed for a plurality of edible crowns across multiple rows of broccoli, in parallel, for harvesting edible crowns within more than one row simultaneously.

Figure 17:
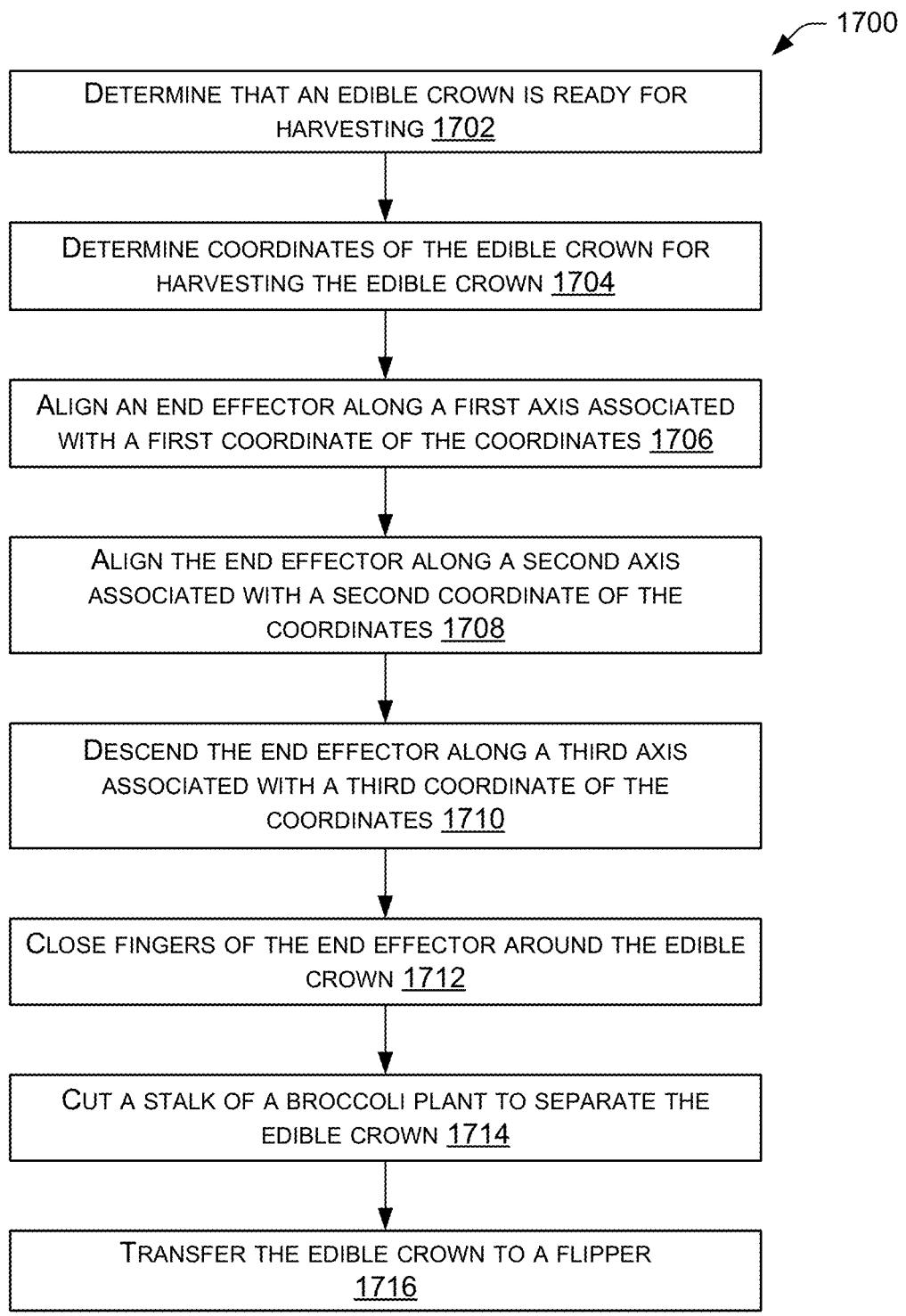
FIG. 17 illustrates an example process for harvesting edible crowns, including aligning harvesting components with an edible crown ready for harvesting, according to an embodiment of the present disclosure.

FIG. 17 illustrates an example process 1700 for aligning the end effector with an edible crown and harvesting the broccoli edible crown.

At 1702, the process 1700 may determine that an edible crown is ready for harvesting. For example, based at least in part on analyzing image data associated with the edible crown, the computing system 500 may determine that the edible crown is ready for harvesting.

At 1704, the process 1700 may determine coordinates of the edible crown for harvesting the edible crown. For example, after determining to harvest the edible crown, the computing system 500 may determine coordinates that are associated with harvesting the edible crown. To determine the coordinates, in some instances, the computing system 500 may analyze the image data 522, the location data 548, and/or the encoder data 546. In some instances, the coordinates may represent a center point of the edible crown (e.g., X, Y, and Z positions), and/or may be relative to components of the harvester 100 that function to harvest the edible crown (e.g., the end effector 536).

At 1706, the process 1700 may align the end effector along a first axis associated with a first coordinate of the coordinates. For example, the robotic arm (e.g., the robotic arm 126 or the robotic arm 1200) and/or the positioning system (e.g., the positioning system 538 and/or the rail system 1234) may move to align the end effector along an X-axis/plane that is associated with an X-coordinate position of the edible crown.

At 1708, the process 1700 may align the end effector along a second axis associated with a second coordinate of the coordinates. For example, the robotic arm and/or the positioning system may move to align the end effector along a Y-axis/plane that is associated with a Y-coordinate position of the edible crown. In some instances, the steps 1706 and 1708 may be performed substantially simultaneously and/or in reverse order. After 1706 and 1708, the end effector 536 may be substantially centered above (e.g., disposed vertically above) the edible crown. In some instances, a center of the end effector may be centered with a center of the edible crown in multiple directions, or along multiple planes (e.g., X and Y planes).

At 1710, the process 1700 may descend the end effector along a third axis associated with a third coordinate of the coordinates. For example, the robotic arm and/or a support (e.g., the support 1232) may move to align the end effector along a Z-axis/plane that is associated with a Z-coordinate position of the edible crown. For example, after being centered above the edible crown, and aligned with the X and Y coordinate positions of the edible crown, the end effector 536 may descend upon the edible crown to align within a Z-plane extending through the center point of the edible crown.

At 1712 the process 1700 may close fingers of the end effector around the edible crown. For example, once the end effector 536 is centered on the edible crown, the fingers (e.g., the fingers 1206) may be actuated via an actuator (e.g., the actuator 1210) for enclosing the fingers around the edible crown. After closing the fingers, the edible crown may be cradled and/or supported within an interior (e.g., the interior space 1220) of the end effector 536. In some instances, the computing system 500 may cause the fingers 1206 to close and/or instruct the actuator to actuate and enclose the edible crown.

At 1714, the process 1700 may cut the stalk to separate the edible crown. For example, after the edible crown is enclosed within the end effector, a cutting mechanism (e.g., the cutting mechanism 540 and/or the cutting mechanism 1224) may actuate to cut the stalk and separate the edible crown from a remaining portion of the stalk. After being cut, the edible crown may remain encased in the end effector, within the fingers.

At 1716, the process 1700 may transfer the edible crown to a flipper. For example, after being harvested, the robotic arm and/or the positioning system may move to transfer the edible crown to the flipper (e.g., the flipper 542). At the flipper 542, the end effector 536 may transition to the open position to transfer the edible crown to the flipper 542. Therein, the edible crown may be transferred to other locations on the harvester 100 to be cleaned and/or further processed.

Figure 18:
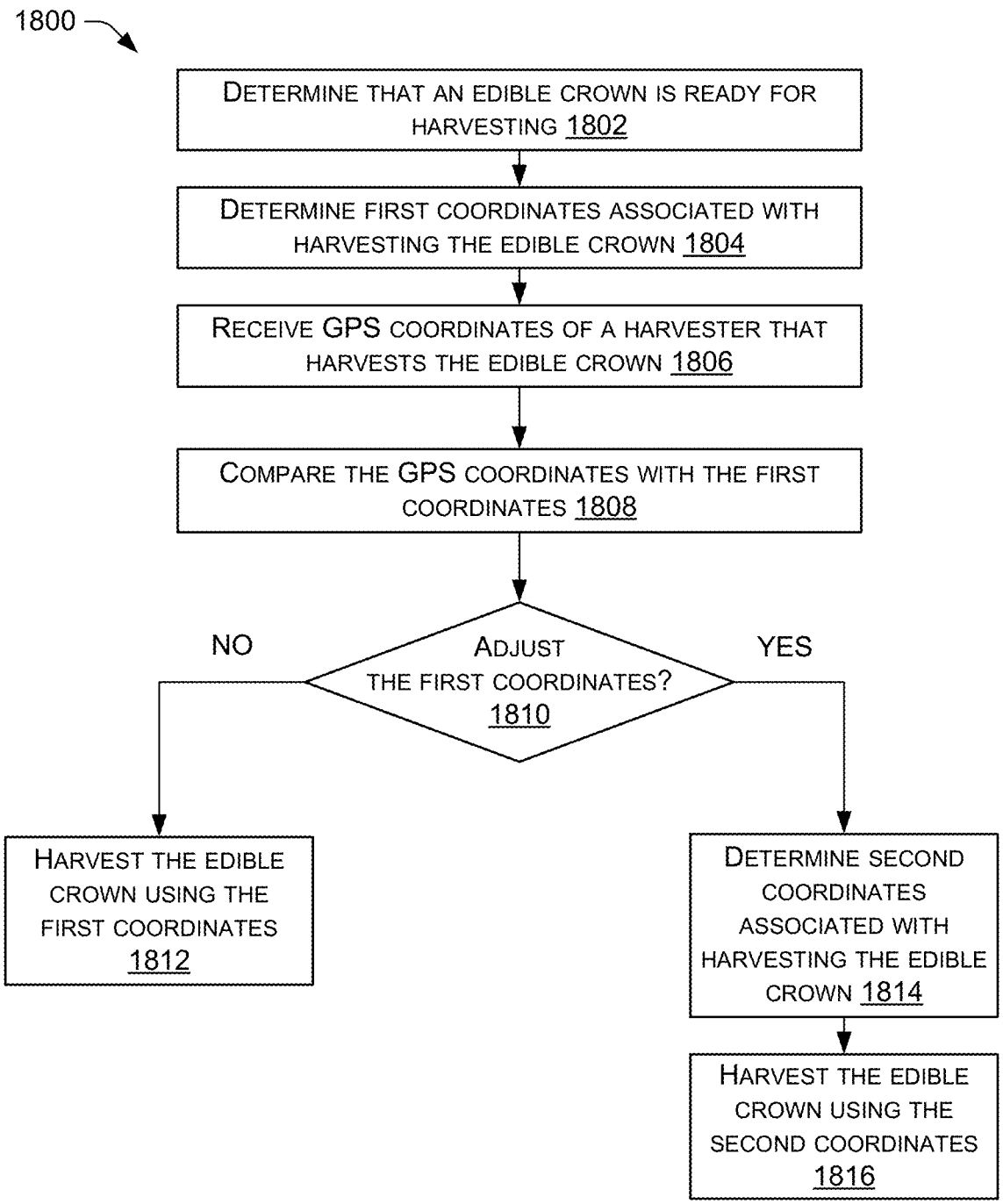
FIG. 18 illustrates an example process for determining a position or coordinates of an edible crown ready for harvesting, according to an embodiment of the present disclosure.

FIG. 18 illustrates an example process 1800 for adjusting harvesting coordinates of an edible crown that is ready for harvesting. Initially, as noted above, at 1802, the process 1800 may determine or receive an indication that an edible crown is ready for harvesting (e.g., based on processing the image data 522).

At 1804, the process 1800 may determine first coordinates associated with harvesting the edible crown. For example, in some instances, the first coordinates may be determined based at least in part on analyzing the encoder data 546 as received from the encoder 544 and/or the image data 522 as generated by the imaging system(s) 516. In some instances, the encoder data 546 may be used to determine a distance traveled by the harvester 100 within the field, and correspondingly, may be used to determine a location (e.g., the first coordinates) of the edible crown. Additionally, or alternatively, the image data 522 (e.g., generated by the IR sensor(s) 520) may be used to determine a location of the edible crown ready for harvesting.

At 1806, the process 1800 may receive GPS coordinates of a harvester that harvests the edible crowns. For example, the navigational system 508 of the harvester 100 may include a GPS component for determining GPS coordinates of the harvester 100. Such GPS coordinates may indicate a position of the harvester 100 within the field, while the first coordinates represent a position of the edible crown within the field. However, knowing the location of the harvester 100 within the field (via the GPS coordinates) allows for a position of the edible crown to be determined. For example, knowing the relative position of the imaging system 516 on the harvester 100 allows for the conversion of the GPS coordinates of the harvester 100 to GPS coordinates of the edible crown.

In some instances, the encoder data 546 used for determining a distance traveled by the harvester 100, which is used to determine the first coordinates, may be subject to inaccuracies. For example, debris may accumulate on the wheels 108 of the harvester 100 and the wheels 108 may occasionally slip (e.g., lose traction). Furthermore, the accumulation of debris may impact a radius of the wheel 108, which may in turn impact a determined distance traveled by the harvester 100 (using the encoder data 546). As such, discussed herein, the first coordinates associated with harvesting the edible crown may be adjusted to account for inaccuracies.

For example, at 1810, the process 1800 may compare the GPS coordinates with the first coordinates. In some instances, comparing the GPS coordinates with the first coordinates may be used to determine an error in the encoder data 546, and the error can be used to determine an adjustment to be applied when determining the coordinates of the edible crown. In this sense, determining whether there is an error may involve comparing the GPS coordinates and the first coordinates in order to compensate for the error in the encoder output.

At 1810, the process 1800 may determine whether to adjust the first coordinates. For example, the computing system 500 may compare the first coordinates with the GPS coordinates to determine whether the first coordinates are different than or similar to the GPS coordinates. In some instances, the difference and/or similarity may be represented at a threshold, or predetermined amount. If the difference, for example, is greater than a threshold then the first coordinates may not be adjusted. If, however, the difference is less than a threshold (e.g., the first coordinates and the GPS coordinates are substantially similar), then the first coordinates may not be adjusted. For example, if the difference is less than a threshold, the process 1800 may determine to not adjust the first coordinates and the process 1800 may follow the "NO" route and proceed to 1812.

At 1812, the process 1800 may harvest the edible crown using the first coordinates. For example, the computing system may transmit instructions to the robotic arm, the positioning system, and/or other components to harvest the edible crown based on the first coordinates.

Alternatively, if at 1810 the process 1800 determines to adjust the first coordinates (e.g., the difference is greater than a threshold), the process 1800 may follow the "YES" route and proceed to 1814.

At 1814, the process 1800 may determine second coordinates associated with harvesting the edible crowns. For example, in some instances, the second coordinates may be based on the GPS coordinates to account for an adjustment in the encoder data (e.g., as mud builds up on the wheels 108 of the harvester). Here, the second coordinates may represent an adjustment applied to the first coordinates when determining the final position coordinates of the edible crown to compensate for the error in the encoder output.

As another example, the image data 522 from the imaging system 516 may be processed using an object detection algorithm to track objects (e.g., rocks, edible crowns, etc.). This object detection may be used to determine a distance traveled by the harvester 100 over a series of images. This image-based distance determination may additionally, or alternatively, be used to determine an error in the encoder data 546, and to determine an adjustment (or offset) to be applied when determining the position coordinates of the edible crowns.

At 1816, the process 1800 may harvest the edible crown using the second coordinates.

Although the process 1800 illustrates determining the coordinates for harvesting the edible crown using the encoder data, and determining whether to adjust the coordinates using the image data and/or the GPS coordinates, in some instances, the coordinates for harvesting the edible crown may be determining using one or more of the image data, the encoder data, an/or the GPS coordinates. For example, the position for harvesting the edible crown may be determined solely from the GPS coordinates and/or solely from the image data. In these instances, the process 1800 may track a position of the harvester 100 and/or distance traveled by the harvester 100 in a forward direction of travel, which may then be used for determining coordinates of unharvested edible crowns (and which are ready for harvesting). Therein, the coordinates are used to control the end effectors.

Figure 19:
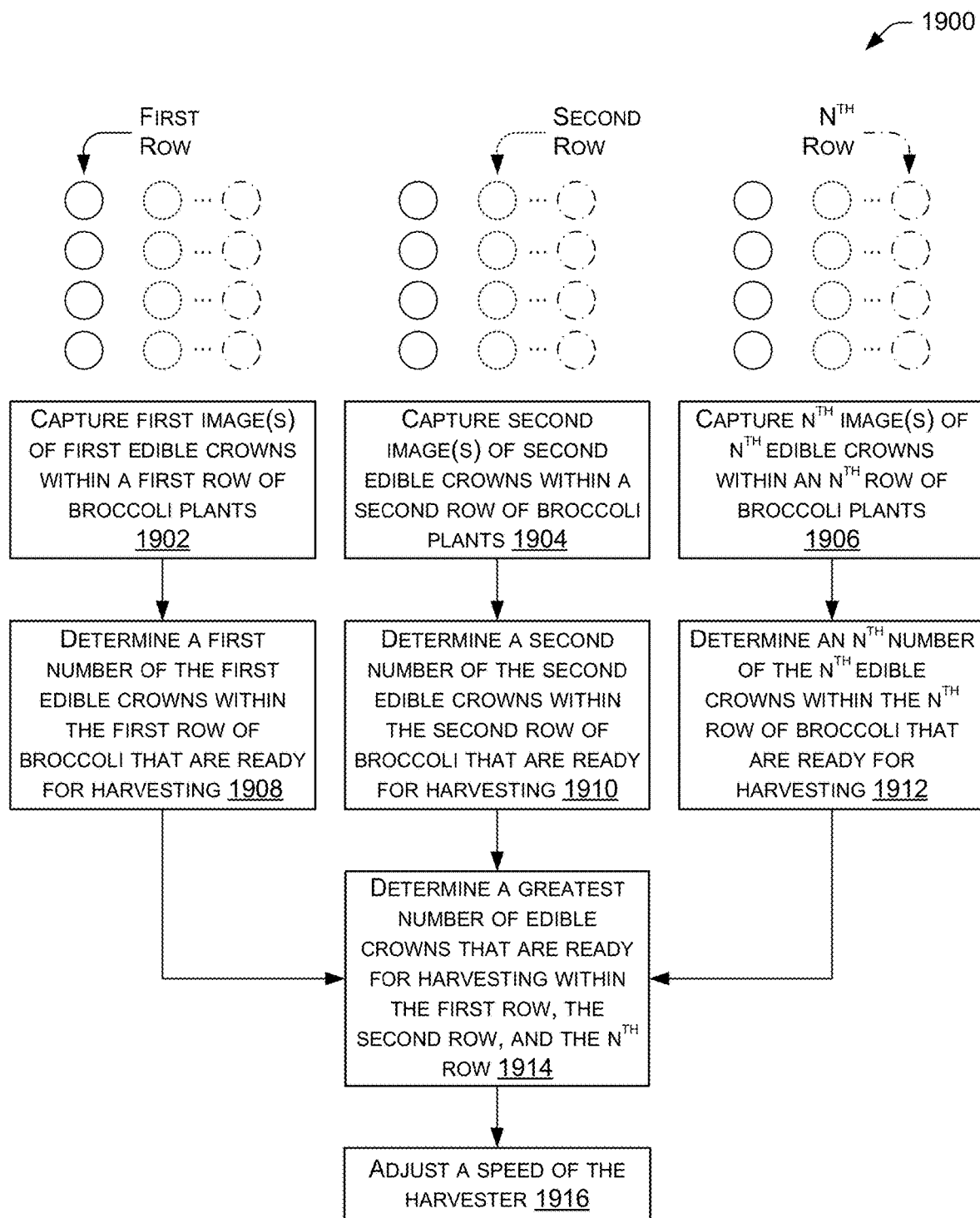
FIG. 19 illustrates an example process for adjusting a speed of a harvester based on a number of harvestable edible crowns across rows of broccoli plants within a field, according to an embodiment of the present disclosure.

FIG. 19 illustrates an example process 1900 for adjusting a speed of the harvester 100 based on a number or ratio of harvestable edible crowns across multiple rows. In some instances, the harvester 100 may adjust in speed based on the number of harvestable and/or unharvestable edible crowns across all rows of broccoli plants that are being harvested by the harvester 100. In this sense, as discussed herein, the harvester 100 may travel as fast as the "slowest" row, or the row having the greatest number of harvestable edible crowns.

Initially, the harvester 100, via the imaging system 516 may image edible crowns of broccoli plants being harvested across the multiple rows. For example, at 1902, the process 1900 may capture first image(s) of first edible crowns within a first row of broccoli plants. At 1904, the process 1900 may capture second image(s) of second edible crowns within a second row of broccoli plants. At 1906, the process 1900 may capture $n^{th}$ image(s) of $n^{th}$ edible crowns within a $n^{th}$ row of broccoli plants. In some instances, the operations 1902, 1904, and 1906 may be performed at the same time as the harvester 100 moves about a field while the harvester 100 is harvesting edible crowns.

After capturing the image(s), the process 1900 may determine a number of harvestable edible crowns within each row of the broccoli plants. For example, at 1908, the process 1900 may determine a first number of edible crowns within the first row of broccoli plants that are ready for harvesting. As discussed in detail hereinabove, the process 1900 may determine the first number of edible crowns to be harvested based on analyzing the first image(s) of the individual broccoli plants within the first row and determining the number of edible crowns within the first row that are ready for harvesting. For example, the process 1900, at 1908, may determine that three edible crowns within the first row are ready for harvesting.

At 1910, the process 1900 may determine a second number of edible crowns within the second row of broccoli plants that are ready for harvesting. The process 1900 may determine the second number of edible crowns to be harvested based on analyzing the second image(s) of the individual broccoli plants and therein, determining the number of edible crowns within the second row that are ready for harvesting. For example, the process 1900, at 1910, may determine that two edible crowns within the second row are ready for harvesting.

At 1912, the process 1900 may determine an $n^{th}$ number of edible crowns within the $n^{th}$ row of broccoli plants that are ready for harvesting. The process 1900 may determine the $n^{th}$ number of edible crowns to be harvested based on analyzing the $n^{th}$ image(s) of the individual broccoli plants and then determining the number of edible crowns within the $n^{th}$ row that are ready for harvesting. For example, the process 1900, at 1912, may determine that zero edible crowns within the second row are ready for harvesting.

After the number of harvestable edible crowns are determined within each row, at 1914, the process 1900 may determine the greatest number of edible crowns within the first row, the second row, and the $n^{th}$ row. For example, the process 1900 may compare the harvestable edible crowns within the first row, the second row, and the $n^{th}$ row (e.g., the first number, the second number, the $n^{th}$ number). Determining which row of the broccoli plants contains the greatest number of harvestable edible crowns may therefore be used for adjusting the speed of the harvester to account for harvester 100 harvesting all of the harvestable edible crowns. For example, continuing with the above example, as the first row has three harvestable edible crowns, the second row has two harvestable edible crowns, and the $n^{th}$ row has zero harvestable edible crowns, the process 1900 may determine that the greatest number of edible crowns ready for harvesting is three.

From 1914, the process 1900 may proceed to 1916 whereby the harvester 100 may adjust in speed to accommodate for the greatest number of harvestable edible crowns. For example, the harvester 100 may slow down in speed to allow the robotic arm(s) 126 of the first row to harvest all of the harvestable edible crowns within the first row. At this same time though, the edible crowns within the second row and the $n^{th}$ row may be harvested by respective robotic arm(s) 126. However, the fastest the harvester 100 may travel is a speed that allows enough time for the robotic arm(s) 126 of the first row to harvest every edible crown within the first row. This means that the harvester 100 may travel at a speed that accommodates the robotic arms 126 in the first row to pick every harvestable edible crown, even if the other robotic arms 126 for the other rows remain relatively idle at times, as there may be relatively fewer harvestable edible crowns in the other rows.

Therefore, in some instances, if there is at least one row of broccoli plants with mostly harvestable edible crowns, the speed of the harvester 100 may be decreased to travel slower over to ensure that the robotic arms 126 for the row with mostly harvestable edible crowns is afforded enough time to harvest all of the edible crowns. Traveling at a higher speed, for example, may not afford enough time for the robotic arms 126 to harvest all of the edible crowns that are ready for harvesting, and as a result, the harvester 100 may pass over certain edible crowns that are ready for harvesting.

By way of another example, if there are relatively few edible crowns that are ready for harvesting across all rows, the speed of the harvester 100 may be increased to travel faster.

In some instances, the harvester 100 may determine the number of harvestable edible crowns across all rows that are being harvested, may determine ratios of harvestable to unharvestable edible crowns, and/or, may determine a number of consecutive harvestable/unharvestable edible crowns in a given row for use in adjusting the travel speed of the harvester 100.

It should be understood that the process 1900 may continuously, and dynamically, determine the number of harvestable edible crowns within each row as the harvester 100 moves about the field. That is, as the harvester 100 moves, broccoli plants within each row will come into a field of view of the imaging systems 516 associated with each row of broccoli. Therein, the imaging systems 516 image the edible crowns, and determine, in real-time, the number of edible crowns to be harvested (or which are ready for harvesting). As suggested, the harvester 100 may determine the number of harvestable edible crowns, per row, and across any number of $n^{th}$ rows (e.g., six, ten, eight, twelve, etc.). The process 1900 continuously determines whether to adjust the speed of the harvester 100, in real-time, based on the number of harvestable edible crowns across the rows of broccoli plants.

As such, because broccoli plants mature at different rates, on a given day, some edible crowns in the field may be ready to harvest, while other edible crowns in the field may not be ready to harvest. The process 1900 may therefore provide efficiency gains by enabling the harvester 100 to travel faster at times when the robotic arms 126 would otherwise remain relatively idle (when there are a few number of edible crowns to be harvested), and slower at times when there are a greater number of edible crowns to be harvested.

Figure 20:
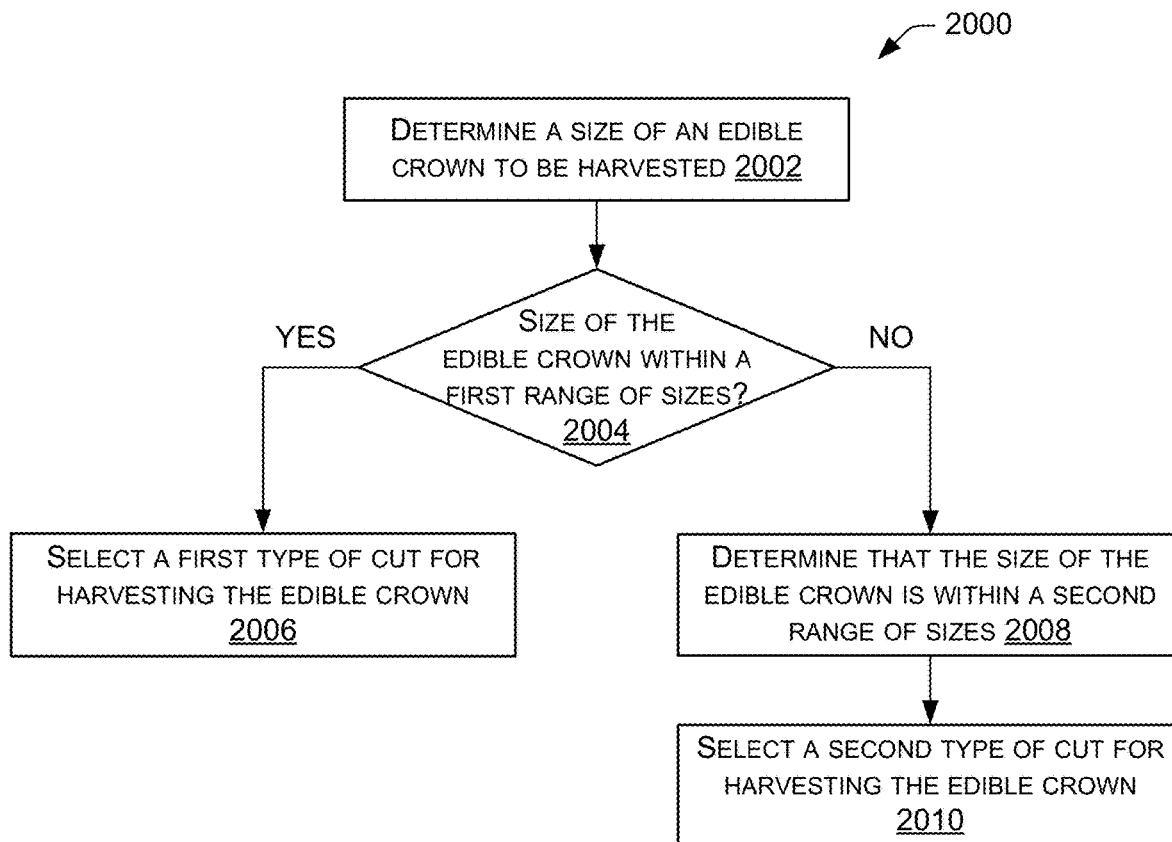
FIG. 20 illustrates an example process for determining a type of cut for edible crowns ready for harvesting, according to an embodiment of the present disclosure.

FIG. 20 illustrates an example process 2000 for determining a type of cut for harvesting edible crowns. In some instances, depending on characteristic(s) of the edible crown to be harvested, the harvester 100 may harvest the edible crown in different ways. In this sense, the harvester 100 may determine a type of cut, or operations for performing types of cuts, depending on the characteristic(s) of the edible crown to be harvested.

At 2002, the process 2000 may determine a size of an edible crown to be harvested. For example, after determining that an edible crown is ready for harvesting, the computing system 500 may determine a size of the edible crown. The size of the edible crown may correspond to a largest cross-sectional dimension, an average cross-sectional dimension, a diameter, an area, volume, and so forth.

In some instances, determining the size of the edible crown may involve analyzing image(s) captured by the imaging system 516 for determining dimensions of the edible crown, such as width (X-direction), length (Y-direction), and/or height (Z-direction). In some instances, in analyzing the image(s) the computing system 500 may determine such dimensions of the edible crown. For example, the computing system 500 may determine that the edible crown is five inches wide. In some instances, the width (or other dimensions) may be an average width or a greatest cross-sectional dimension. For example, edible crowns often grow irregular and are not symmetrical. The edible crown may therefore be ovular, egg-shaped, hexagonal, circular, and/or any combination thereof. In determining the size of the edible crown, the computing system 500 may determine a greatest cross-sectional dimension among a plurality of cross-sectional dimension (e.g., random sampling of cross-sectional dimensions). The computing system 500 then determine the greatest cross-sectional dimension for determining the size of the edible crown. In some instances, the computing system 500 may determine an average cross-sectional dimension for use in determining the size of the edible crown.

At 2004, the process 2000 may determine whether the size of the edible crown is within a first range of sizes. For example, the computing system 500 may compare the size of the edible crown with the first range of sizes, or bounds thereof, for determining whether the size of the edible crown is within the first range of sizes. By way of example, the first range of sizes may be from 4.0 and 4.75 inches. Accordingly, if the size of the edible crown is 5 inches, the computing system 500 may determine that the size of the edible crown is not within the first range of sizes.

In instances where the size of the edible crown is within the first range of sizes, the process 2000 may follow the "YES" route and proceed to 2006.

At 2006, in response to determining that the size of the edible crown is within the first range of sizes, the process 2000 may select a first type of cut for harvesting the edible crown. For example, as noted above, depending on the size of the edible crown, the harvester 100 may perform different types of cuts, or different operations for harvesting the edible crown. In some instances, the first type of cut may include grasping the edible crown and cutting the stalk with the cutting mechanism 540. Therein, the edible crown may be harvested and transferred to other components of the harvester 100.

Alternatively, if at 2004, the process 2000 determines that the size of the edible crown is not within the first range of sizes, the process 2000 may follow the "NO" route and proceed to 2008.

At 2008, the process 2000 may determine that the size of the edible crown is within a second range of sizes. For example, as a result of not being within the first range of sizes, the process 2000 may determine that the size is within a second range of sizes, such as between 4.75 and 5.75 inches.

At 2010, the process 2000 may select a second type of cut for harvesting the edible crown. For example, the computing system 500 may determine to harvest the edible crown using a second type of cut that is different than the first type of cut. In some instances, the second type of cut may include stripping the leaves around the edible crown and then cutting the edible crown. For example, once the end effector 536 grasps around the edible crown (with the fingers 1206), the robotic arm 126 (or other actuators) may advance the end effector downward towards the ground to strip or peel back leaves that may be adjacent to the edible crown. Stripping back the leaves in this manner may reduce processing time at later operations to clean or remove leaves. After moving downward, the robotic arm 126 may pull the end effector back up to a position where the cutting mechanism 540 severs the stalk below the edible crown.

As such, the harvester 100 may perform different operations for harvesting the edible crown based on a size of the edible crown. Although the process 2000 is illustrated and described herein as including two types of cuts, the harvester 100 may be configured for performing more types of cuts, such as three or four. In some instances, these types of cuts may be dependent on the size of the edible crown (e.g., cross-sectional dimension), the shape of the edible crown, a height of the edible crown, or other characteristics. As the size of the edible crown may equate to leaves or other foliage being around the edible crown, these types of cuts may serve to reduce post-processing of the edible crown (e.g., removing leaves, cleaning, etc.). In some instances, the type of cut performed may be dependent upon a length of stalk desired to be attached (or remaining attached) to the edible crown.

FIGS. 21A-21E illustrate detailed views of a robotic arm 2100 of the harvester 100. In some instances, the robotic arm 2100 may be similar to and/or include features as described above with regard to the robotic arm 126 and/or the robotic arm 2100. Additionally, the robotic arm 2100 may be usable with the processes described above. The robotic arm 2100 includes an end effector 2102. In some instances, the end effector 2102 may be similar to and/or include features as described above with regard to the end effector 536 and/or the end effector 2102. The end effector 2102 is configured to transition between an open position.

As similarly discussed above with regard to the end effector 536 and/or the end effector 2102, the end effector 2102 may represent a gripper that grasps edible crowns of broccoli plants ready for harvesting. In the open position, the end effector 2102 may descend unto or over edible crowns. In the closed position, the end effector 2102 may grasp onto edible crowns (or portions of the stalk) for retaining edible crowns within the end effector 2102.

As shown, and similar to the end effector 2102, the end effector 2102 may include a body 2104 and fingers 2106 attached to the body 2104. In some instances, the end effector 2102 may include two fingers 2106. However, in some instances, the end effector 2102 may include more than two fingers, such as three fingers, four fingers, and/or any other number of fingers. The fingers 2106 may pivotably couple to the body 2104 for allowing the fingers 2106 to transition between the open position and the closed position. Additionally, the end effector 2102 (or the robotic arm 2100) may include an actuator for transitioning the end effector 2102 (or the fingers 2106) between the open position and the closed position. In some instances, the actuator may include a linear actuator or a rotary actuator. The actuator may couple to the fingers 2106 via linkages, connectors, bars, and so forth. For example, as shown and in some instances, the fingers 2106 may couple to the actuator via one or more linkages.

The fingers 2106 may engage with a stalk of the broccoli plants, below the edible crown of the broccoli plant when the end effector 2102 transitions to the closed position. In the closed position, the fingers 2106 may define an internal space occupied by the edible crown, or which the edible crown is configured to reside within while being harvested and/or after being harvested.

The end effector 2102 is shown including a cutting mechanism 2108 for cutting the stalk of the broccoli plant to separate the edible crown from the rest of the broccoli plant. In some instances, the cutting mechanism 2108 may be similar to and/or include features as described above with regard to the cutting mechanism 540. However, as shown, the cutting mechanism 2108 may be different than the cutting mechanism 1224 as discussed above with regard to the end effector 2102.

Figure 21A:
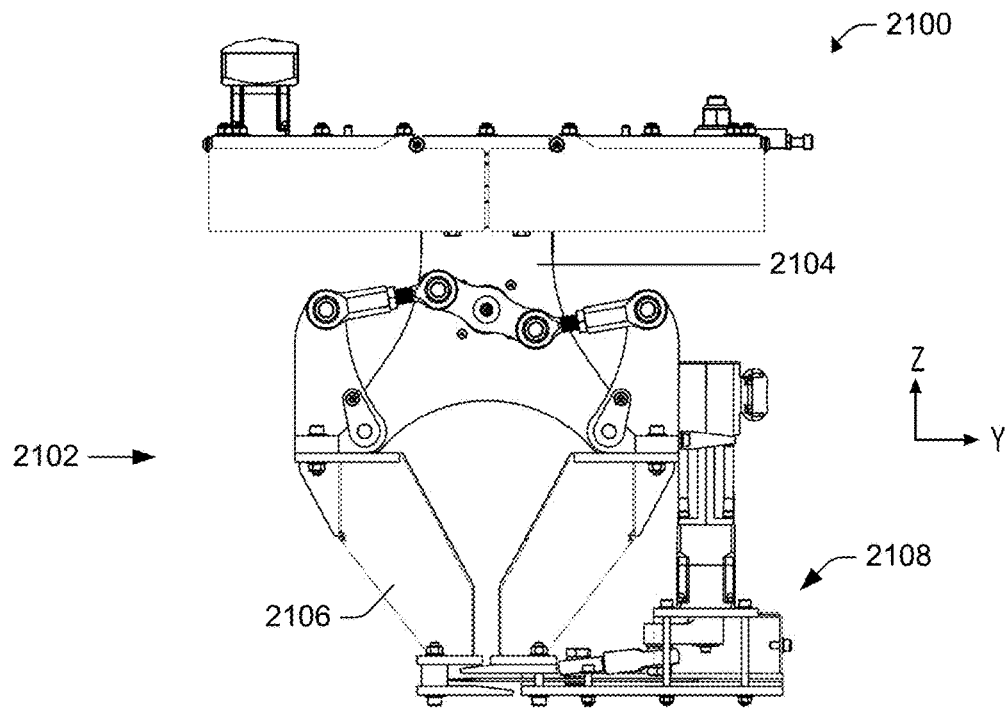
FIG. 21A illustrates a side view of example harvesting components of the harvester of FIG. 1, according to an embodiment of the present disclosure. In some instances, the harvesting components may include a robotic arm and/or an end effector for grasping the edible crown and a cutting mechanism for severing the edible crown from the broccoli plant. The end effector may operably transition between an open state and a closed state for grasping the edible crown and releasing the edible crown at a collection point.
Figure 21B:
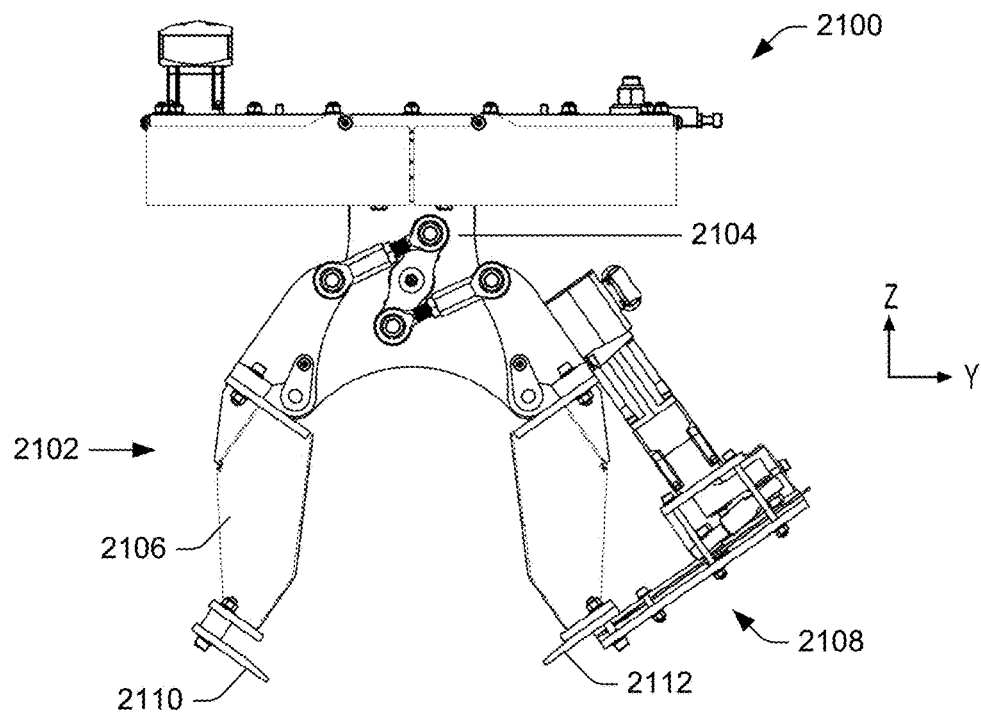
FIG. 21B illustrates a side view of the harvesting components of FIG. 21A, according to an embodiment of the present disclosure.
Figure 21C:
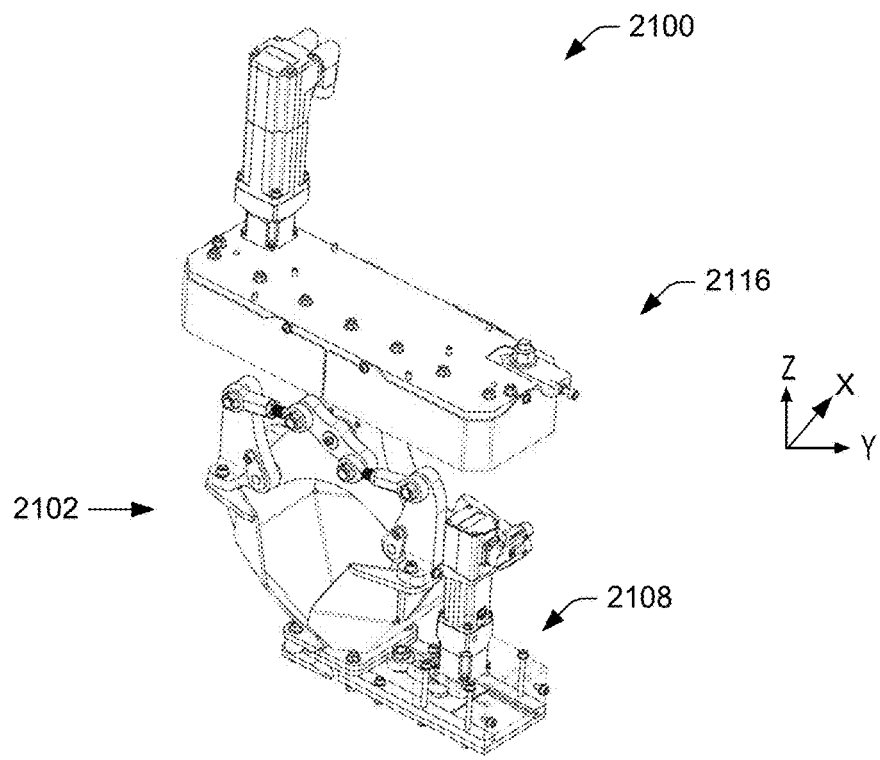
FIG. 21C illustrates a perspective view of the harvesting components of FIG. 21A, according to an embodiment of the present disclosure.
Figure 21D:
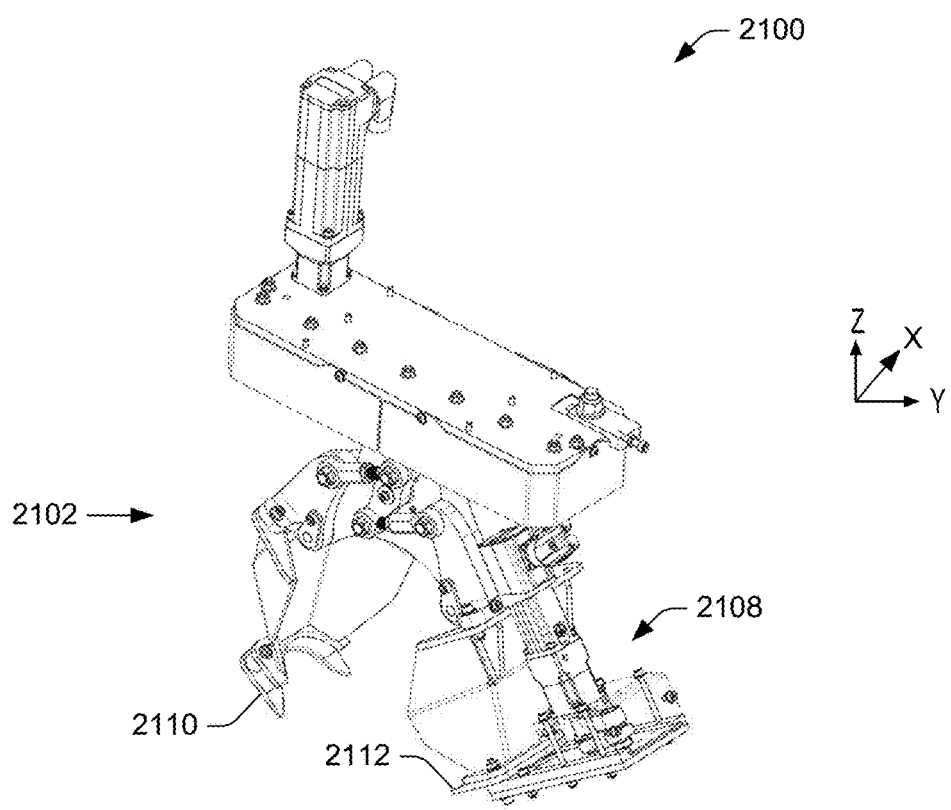
FIG. 21D illustrates a perspective view of the harvesting components of FIG. 21A, according to an embodiment of the present disclosure.
Figure 21E:
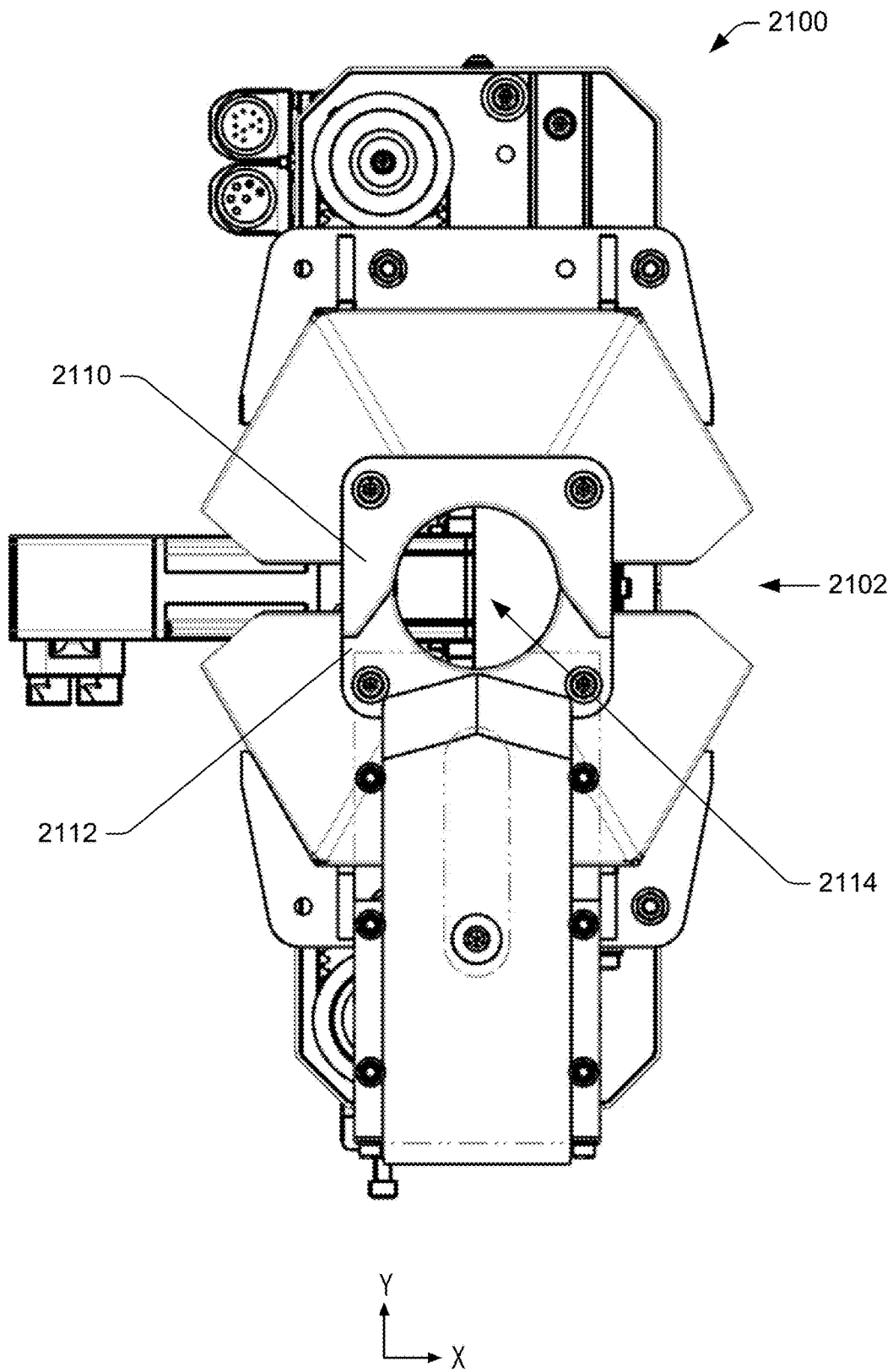
FIG. 21E illustrates an end view of the harvesting components of FIG. 21A, according to an embodiment of the present disclosure.

In some instances, the cutting mechanism 2108 may include a first blade 2110 disposed on an end of a first of the fingers 2106 and a second blade 2112 disposed on a second of the fingers 2106. In some instances, the first blade 2110 and the second blade 2112 may represent a double guillotine blade-like cutter that, when the end effector 2102 encloses the edible crown, the second blade 2112 actuates to cut the stalk. In some instances, the cutting mechanism 2108 may include an air actuator or an electric motor that extends the second blade 2112 towards the first blade 2110 to cut through the stalk. For example, referring to FIG. 21E, when the end effector 2102 is in the closed state, an opening 2114 may be defined at least partially between the first blade 2112 and the second blade 2112. As the end effector 2102 closes, the stalk of the broccoli plant may be positioned within the opening, while the edible crown may be disposed within an interior of the fingers 2106. Therein, the actuator of the cutting mechanism 2108 may actuate the second blade 2112 in the Y-direction, towards the first blade 2110. This actuation may sever the edible crown from the stalk. As such, the first blade 2110 and the second blade 2112 may function as a guillotine-style cutter for severing the edible crown. In some instances, the actuator may linearly actuate the second blade 2112 towards the first blade 2110. As shown in FIGS. 21D and 21E, for example, the first blade 2110 and/or the second blade 2112 may be semi-circular in shape to be disposed around a perimeter of the stalk when the end effector 2102 closes.

In some instances, after cutting the stalk, the second blade 2112 may remain in a cut position such that the second blade 2112 is disposed within the opening 2114, with the stalk resting on a surface of the second blade 2112. The stalk may rest on the second blade 2112 to prevent the edible crown repositioning within the end effector 2102.

In some instances, the body 2104 may include a base end connected to the robotic arm 2100. In some instances, the robotic arm 2100 and/or the body 2104 may couple to a positioning system 2116 (e.g., the positioning system 538) for maneuvering the end effector 2102. In some instances, the positioning system 2116 may include mounts, brackets, gears, slides, tracks, motors, wheels, pulleys, pneumatics, hydraulic cylinders, cables, screw drives, turntables, or other actuators that position, move, or orient the end effector 2102. The positioning system 2116, in some instances, may also extend to various lengths to position the end effector 2102 at various positions. Although the robotic arm 2100 is described as coupling or including certain components for positioning the end effector 2102 relative to the edible crown, other components may be included.

The fingers 2106 may include a single unitary body or may be assembled from multiple components. Additionally, the fingers 2106 may include troughs, channels, flanges, or other features that engage with a bottom or underneath side of the edible crown. Such engagement may cusp, cradle, and secure the edible crown within an internal space of the end effector 2102. Moreover, the computing system 500 may communicatively couple or control the robotic arm 2100 and components thereof, such as the actuator, the cutting mechanism 2108, etc.

While various examples and embodiments are described individually herein, the examples and embodiments may be combined, rearranged, and modified to arrive at other variations within the scope of this disclosure.

Although the subject matter has been described in language specific to structural features and/or methodological acts, it is to be understood that the subject matter defined in the appended claims is not necessarily limited to the specific features or acts described. Rather, the specific features and acts are disclosed as illustrative forms of implementing the claims.

What is claimed is:

1. A machine, comprising:
   a sensor;
   a robotic arm;
   one or more processors; and
   one or more computer-readable media storing instructions that, when executed, cause the one or more processors to perform operations comprising:
      determining criteria associated with harvesting edible crowns;
      receiving, from the sensor, sensor data associated with an edible crown,
      determining, based at least in part on the sensor data, a first characteristic of the edible crown and a second characteristic of the edible crown;
      determining that the first characteristic and the second characteristic satisfy the criteria;
      determining, based at least in part on the first characteristic and the second characteristic satisfying the criteria, to harvest the edible crown; and
      causing the robotic arm to harvest the edible crown.

2. The machine of claim 1, wherein:
   the criteria comprises at least a threshold size of the edible crowns and a predetermined color of the edible crowns;
   the first characteristic comprises a size of the edible crown;
   the second characteristic comprises a color of the edible crown; and
   determining that the first characteristic and the second characteristic satisfy the criteria comprises:
      determining that the size of the edible crown satisfies the threshold size, and
      determining that the color of the edible crown satisfies the predetermining color.

3. The machine of claim 1, the operations further comprising:
   receiving, from the sensor, second sensor data associated with a second edible crown;
   determining, based at least in part on the second sensor data, at least one of a third characteristic of the second edible crown or a fourth characteristic of the second edible crown;
   determining that the at least one of the third characteristic or the fourth characteristic fail to satisfy the criteria; and
   determining, based at least in part on the at least one of the third characteristic or the fourth characteristic failing to satisfy the criteria, to refrain from harvesting the edible crown.

4. The machine of claim 3, the operations further comprising determining a future instance in time associated with harvesting the second edible crown, and wherein the future instance in time is based at least in part on at least one of:
   the criteria;
   the third characteristic of the second edible crown; or
   the fourth characteristic of the second edible crown.

5. The machine of claim 1, the operations further comprising:
   providing the sensor data as an input to a trained machine-learning model;
   receiving, as first output from the trained machine-learning model, a first indication associated with the first characteristic being indicative of whether the edible crown is ready for harvesting; and
   receiving, as second output from the trained machine-learning model, a second indication associated with the second characteristic being indicative of whether the edible crown is ready for harvesting,
   wherein determining that the first characteristic and the second characteristic satisfy the criteria is based at least in part on the first indication and the second indication.

6. The machine of claim 1, wherein causing the robotic arm to harvest the edible crown comprises:
   causing the robotic arm to move to a first position associated with severing the edible crown from a stalk; and
   causing the robotic arm to move to a second position associated with releasing the edible crown from the robotic arm.

7. The machine of claim 6, wherein an end effector couples to the robotic arm, the end effector being configured to:
   transition from a first state to a second state to grasp the edible crown; and
   transition from the second state to the first state to release the edible crown.

8. A method, comprising:
   determining criteria associated with harvesting edible crowns;
   receiving first sensor data associated with an edible portion of a first plant,
   determining, based at least in part on the first sensor data, a first characteristic of the edible portion of the first plant;
   determining that the first characteristic satisfies the criteria;
   determining, based at least in part on the first characteristic satisfying the criteria, to harvest the edible portion of the first plant;
   receiving second sensor data associated with an edible portion of a second plant,
   determining, based at least in part on the second sensor data, a second characteristic of the edible portion of the second plant;
   determining that the second characteristic fails to satisfy the criteria; and
   determining, based at least in part on the second characteristic failing to satisfy the criteria, to refrain from harvesting the edible portion of the second plant.

9. The method of claim 8, further comprising:
   determining, based at least in part on the first sensor data, a third characteristic of the edible portion of the first plant;
   determining that the third characteristic satisfies the criteria;
   determining, based at least in part on the second sensor data, a fourth characteristic of the edible portion of the second plant; and
   determining that the fourth characteristic fails to satisfy the criteria, wherein:
      determining to harvest the edible portion of the first plant is further based at least in part on the third characteristic satisfying the criteria, and
      determining to refrain from harvesting the edible portion of the second plant is further based at least in part on the fourth characteristic failing to satisfy the criteria.

10. The method of claim 8, further comprising determining, based at least in part on the second characteristic, an instance in time associated with the edible portion of the second plant being ready for harvesting.

11. The method of claim 10, further comprising:
  determining a location of the second plant within a field; and
  storing a first indication of the instance in time and a second indication of the location in association with the second plant.

12. The method of claim 8, wherein:
  the criteria includes at least one of:
    a color of edible portions being ready for harvesting,
    a size of the edible portions being ready for harvesting,
    a shape of the edible portions being ready for harvesting, or
    a density of the edible portion being ready for harvesting;
  the first characteristic comprises one of:
    a first color of the edible portion of the first plant,
    a first size of the edible portion of the first plant,
    a first shape of the edible portion of the first plant, or
    a first density of the edible portion of the first plant; and
  the second characteristic comprises one of:
    a second color of the edible portion of the second plant,
    a second size of the edible portion of the second plant,
    a second shape of the edible portion of the second plant, or
    a second density of the edible portion of the second plant.

13. The method of claim 8, further comprising causing at least one of a robotic arm or an end effector to harvest the edible portion of the first plant.

14. A machine, comprising:
  a harvesting component;
  one or more sensors;
  one or more processors; and
  one or more computer-readable media storing instructions that, when executed, cause the one or more processors to perform operations comprising:
    determining criteria associated with harvesting edible portions of plants within a field,
    receiving, from the one or more sensors, sensor data associated with an edible portion of a plant,
    determining, based at least in part on the sensor data, one or more characteristics of the edible portion of the plant,
    determining that the one or more characteristics satisfy the criteria,
    determining, based at least in part on the one or more characteristics satisfying the criteria, to harvest the edible portion of the plant, and
    causing the harvesting component to harvest the edible portion of the plant.

15. The machine of claim 14, the operations further comprising determining a position of the edible portion of the plant, and wherein causing the harvesting component to harvest the edible portion of the plant comprises causing the harvesting component to at least move to the position.

16. The machine of claim 14, the operations further comprising:
  receiving second sensor data associated with an edible portion of a second plant;
  determining, based at least in part on the second sensor data, one or more second characteristics of the edible portion of the second plant;
  determining that the one or more second characteristics fail to satisfy the criteria; and
  determining, based at least in part on the one or more characteristics failing to satisfy the criteria, to refrain from harvesting the edible portion of the second plant.

17. The machine of claim 16, the operations further comprising determining, based at least in part on the one or more second characteristics, an instance in time associated with at least one of:
  harvesting the edible portion of the second plant, or
  the edible portion of the second plant being ready for harvesting.

18. The machine of claim 17, the operations further comprising:
  determining at least one of:
    a first location of the second plant within the field, or
    a second location of the machine within the field; and
  storing an indication associated with at least one of:
    the instance in time,
    the first location, or
    the second location.

19. The machine of claim 16, wherein:
  determining the one or more characteristics of the edible portion of the plant comprises providing the sensor data as an input to a trained machine-learning model; and
  the trained machine-learning model is configured to generate an output indicating whether the one or more characteristics are representative of the edible portion of the plant being ready for harvesting.

20. The machine of claim 16, wherein the one or more characteristics comprise a least one of:
  a color of the edible portion of the plant;
  a size of the edible portion of the plant;
  a shape of the edible portion of the plant; or
  a density of the edible portion of the plant.

* * * * *